US010175244B2

(12) United States Patent
Garrido et al.

(10) Patent No.: US 10,175,244 B2
(45) Date of Patent: Jan. 8, 2019

(54) DOMINANT NEGATIVE HSP110 MUTANT AND ITS USE IN PROGNOSING AND TREATING CANCERS

(71) Applicants: Carmen Garrido, Dijon (FR); Alex Duval, Paris (FR)

(72) Inventors: Carmen Garrido, Dijon (FR); Alex Duval, Paris (FR)

(73) Assignees: INSERM (INSTITUT NATIONAL DE LA SANTÉ ET DE LA RECHERCHE MÉDICALE), Paris (FR); UNIVERSITE DE BOURGOGNE, Dijon (FR)

( * ) Notice: Subject to any disclaimer, the term of this patent is extended or adjusted under 35 U.S.C. 154(b) by 332 days.

(21) Appl. No.: 14/852,664

(22) Filed: Sep. 14, 2015

(65) Prior Publication Data

US 2015/0377892 A1    Dec. 31, 2015

Related U.S. Application Data

(63) Continuation of application No. 14/006,501, filed as application No. PCT/EP2012/055339 on Mar. 26, 2012.

(30) Foreign Application Priority Data

Mar. 24, 2011    (EP) .................................... 11305330

(51) Int. Cl.
| G01N 33/50 | (2006.01) |
| G01N 33/68 | (2006.01) |
| C12Q 1/68 | (2018.01) |
| G01N 33/574 | (2006.01) |
| C07K 14/47 | (2006.01) |
| C12Q 1/6886 | (2018.01) |
| C07K 14/435 | (2006.01) |

(52) U.S. Cl.
CPC ..... *G01N 33/57496* (2013.01); *C07K 14/435* (2013.01); *C07K 14/47* (2013.01); *C12Q 1/6886* (2013.01); *G01N 33/57484* (2013.01); *C12Q 2600/118* (2013.01); *C12Q 2600/156* (2013.01); *G01N 2333/47* (2013.01); *G01N 2800/52* (2013.01)

(58) Field of Classification Search
None
See application file for complete search history.

(56) References Cited

U.S. PATENT DOCUMENTS

2006/0167065 A1    7/2006  Wilde et al.
2009/0041754 A1*   2/2009  Endoh ................ G01N 33/6803
                                                  424/130.1

FOREIGN PATENT DOCUMENTS

FR         2 912 745 A1    8/2008
WO    WO2014/154898    * 10/2014

OTHER PUBLICATIONS

Retsky (Breast Cancer Res Treat, vol. 134, p. 881-888, 2012) (Year: 2012).*
Horne (International Journal of Cancer, vol. 00, p. 1-10, 2014) (Year: 2014).*
Valent (Nature Reviews: Cancer, vol. 12, p. 767-775, 2012) (Year: 2012).*
Komenaka et Al., Clinics in Dermatology, 2004, vol. 22, p. 251-265 (Year: 2004).*
Evans et Al. (Q. J. Med 1999: 92: 299-307) (Year: 1999).*
Schiffman et Al., The New England Journal of Medicine, Vo. 353, No. 20, p. 2101-2104, 2005 (Year: 2005).*
Cuzick et Al. (The Lancet, vol. 361, p. 296-300, 2003) (Year: 2003).*
Hernandez-Ledesma (Peptides, vol. 30, p. 426-430, 2009) (Year: 2009).*
Ludwig et Al. (Nature Reviews: Cancer, vol. 5, p. 845-856, 2005) (Year: 2005).*
Pepe et Al. (Journal of the National Cancer Institute, vol. 93, No. 14, p. 1054-1061, 2001) (Year: 2001).*
Mettlin et Al. (Cancer, vol. 74, No. 5, p. 1615-1620, 1994) (Year: 1994).*
Brawer et Al. (Urology, vol. 52, No. 3, p. 372-378, 1998) (Year: 1998).*
Budman et Al. (CUAJ, vol. 2, Issue 3, p. 212-221, 2008) (Year: 2008).*
Horne (International Journal of Cancer, vol. 00, p. 1-10, 2014) (Year: 2014).*
Ribic (N. England J. Med., vol. 349, p. 247-257, 2003) (Year: 2003).*
Hyun et al., "The Chaperoning Activity of HSP110 Identification of Functional Domains by Use of Targeted Deletions", Journal of Biological Chemistry, May 28, 1999, pp. 15712-15718, vol. 274, No. 22, The American Society of Biological Chemists, Inc., US.
"SubName: Full=Heat shock protein 105", DATABASE UniProt, Jul. 5, 2004, Web.
Deschoolmeester et al., "Detection of microsatellite instability in colorectal cancer using an alternative multiplex assay of quasi-monomorphic mononucleotide markers", Journal of Molecular Diagnostics, Mar. 1, 2008, pp. 154-159, vol. 10, No. 2, American Society for Investigative Pathology, Bethesda, MD, US.
Iyare et al., "Improved Testing for Microsatellite Instability in Colorectal Cancer Using a Simplified 3-Marker Assay", Annals of Surgical Oncology, Aug. 12, 2010, pp. 3370-3378, vol. 17, No. 1, Springer-Verlag, NE.

(Continued)

*Primary Examiner* — Michael Allen
(74) *Attorney, Agent, or Firm* — W&C IP

(57) ABSTRACT

The present invention relates to a mutated heat-shock protein 110 (HSP110) lacking its substrate binding domain, which does not exhibit its chaperon activity and/or is not capable of binding to best-shock protein 70 (HSP70) and/or to beat-shock protein 27 (HSP27), but which is capable of binding to a wild-type HSP110. Such a mutated heat-shock protein 110 can be used (i) in methods for proposing survival and/or the response to a treatment of a patient suffering from a cancer, more particularly from a cancer liable to have a microsatellite instability (MSI) phenotype, such as colorectal cancer (CRC), and (ii) for treating cancers.

2 Claims, 17 Drawing Sheets

Specification includes a Sequence Listing.

(56) References Cited

OTHER PUBLICATIONS

Durand et al., "Inhibition of nonsense-mediated mRNA decay (NMD) by a new chemical molecule reveals the dynamic of NMD factors in P-bodies", The Journal of Cell Biology, Sep. 24, 2007, pp. 1145-1160, vol. 178, No. 7.

Slaby et al., "Significant overexpression of Hsp110 gene during colorectal cancer progression", Oncology Reports, May 1, 2009, pp. 1235-1241, vol. 21, No. 5.

Coralie et al., "Expression of a mutant HSP110 sensitizes colorectal cancer cells to chemotherapy and improves disease prognosis", Nature Medicine, Nov. 25, 2011, pp. 1283-1289, vol. 17, No. 10.

* cited by examiner

DOMINANT NEGATIVE HSP110 MUTANT AND ITS USE IN PROGNOSING AND TREATING CANCERS

CROSS-REFERENCE TO RELATED APPLICATIONS

This application is a continuation of U.S. Ser. No. 14/006,501 filed Oct. 17, 2013, which itself was a Rule 371 national stage filing of International Application PCT/EP2012/055339 filed Mar. 26, 2012 which claimed priority to European Application 11305330.0 filed Mar. 24, 2011.

The present invention relates to a mutated heat-shock protein 110 (HSP110) lacking its substrate binding domain, which does not exhibit its chaperone activity and/or is not capable of binding to heat-shock protein 70 (HSP70) and/or to heat-shock protein 27 (HSP27), but which is capable of binding to a wild-type HSP110. Such a mutated heat-shock protein 110 can be used (i) in methods for prognosing survival and/or the response to a treatment of a patient suffering from a cancer, more particularly from a cancer liable to have a microsatellite instability (MSI) phenotype, such as colorectal cancer (CRC), and (ii) for treating cancers.

HSP Proteins and HSP110

Heat shock proteins (HSP) are a class of functionally related proteins, called chaperone proteins, whose expression is increased when cells are exposed to elevated temperatures or other stress, such as infection, inflammation, exercise, exposure of the cell to toxins (ethanol, arsenic, trace metals and ultraviolet light, among many others), starvation, hypoxia (oxygen deprivation), nitrogen deficiency (in plants), or water deprivation. Consequently, the heat shock proteins are also referred to as stress proteins and their upregulation is sometimes described more generally as part of the stress response. The chaperone activity of HSP proteins is mediated by their ATP binding domain and is essential for protein folding, for protein complex formation, for transmembrane transport of proteins and for targeting some of them to lysosomal degradation. In Human, there are at least eight HSP proteins, including HSP70 and HSP110. Since the mid-1990s, it is known that HSP70 is abundantly expressed in cancer cells (both cell lines and tumors) in a pattern that correlates with poor differentiation, a high proliferative capacity in propensity for metastasis and resistance to various cytotoxic agents.

Like other stress inducible HSPs, HSP110, also named HSP105, protects the cell against adverse conditions. However, HSP110 also provides specific critical functions since hsp110 gene knockout in both yeast and *Drosophila* is lethal (Trott et al., *Genetics* 170 (3), 1009 (2005)). HSP110 not only acts as a nucleotide exchange factor for HSP70 (Andreasson et al., *Proceedings of the National Academy of Sciences of the United States of America* 105 (43), 16519 (2008)) but also possesses chaperone anti-aggregation activity. It is approximately four-fold more efficient at binding and stabilizing denatured protein substrates compared to HSC70 and HSP70 (Wang et al., *Cancer research* 63 (10), 2553 (2003)). Moreover, it is also known that HSP110 can act as an inducer of HSP70, thereby playing an important role in the protection of cells against deleterious stressor together with HSP70. Recently, it has been demonstrated that HSP110 accumulates abnormally in cancer cells and this is believed to enhance their survival (Yamagishi et al., *The FEBS journal* 275 (18), 4558 (2008); Hosaka et al., *Cancer science* 97 (7), 623 (2006); Yamagishi et al., *Experimental cell research* 312 (17), 3215 (2006); Siatskas et al., *Faseb J* 19 (12), 1752 (2005)). HSP110 is especially strongly expressed in colon cancer cells (Kai et al., *Oncology reports* 10 (6), 1777 (2003)), and gene expression profile analysis of microsatellite stable (MSS) primary colorectal cancer (CRC) has linked HSP110 expression with metastasis and poor prognosis (Slaby et al., *Oncology reports* 21 (5), 1235 (2009)).

Microsatelllte Instability Phenotype and Microsatellite Stable Phenotype

A subset of cancers is characterized by a Mismatch Repair (MMR) deficiency, notably because of inactivating alterations of the MMR genes MLH1, MSH2, MSH6 and PMS2. As a consequence, these tumors exhibit a particular phenotype called "Microsatellite Instability" or "MSI" characterized by a global instability phenomenon affecting microsatellite repetitive sequences. Tumors with MSI phenotype can occur in the context of rare inherited syndromes such as Lynch syndrome or Constitutional Mismatch-Repair Deficiency (CMMR-D) or can occur sporadically in as many as 10-15% of colorectal, gastric and endometrial cancers and to a lesser extent in many other tumors (Duval and Hamelin, *Annales de génétique* 45: 71-75 (2002)).

The Lynch syndrome is due to autosomal mutation in one of the 4 genes MLH1, MSH2, MSH6, PMS2 called "MMR genes" which are involved in the mismatch repair during DNA replication. Patients suffering from Lynch syndrome have a risk of 70% to develop, in their adult years, colon cancer and various cancer affecting endometrium, ovary, stomach, small intestine, liver, superior urinary system, brain and skin.

Besides, the CMMR-D/Lynch 3 syndrome is due to biallelic deleterious germline mutations in MMR genes (Ricciardone et al., *Cancer Res.* 59: 290-3 (1999); Wang et al., *Cancer Res.* 59: 294-7 (1999)) and is characterized by the development of childhood tumors and a huge clinical spectrum very different from one patient to another. The tumors are mainly lymphomas, leukemias, astrocyte-derived brain tumors and/or very early-onset colorectal tumors. Other signs, named call signs, such as atypical "café-au-lait" spots are frequently observed in CMMR-D patients, being however also present in healthy subjects from the general population. They allow recognizing, even if not specific, at-risk individuals for CMMR-D syndrome in the general population before the emergence of cancers.

In sporadic MSI cancers, such as colorectal, gastric or endometrial cancers, the MMR deficiency is due to epigenetic and bi-allelic silencing of MLH1 by de novo methylation of its promoter site in more than 90% of the cases, regardless of the primary site of tumor (Kane et al., *Cancer Research* 57: 808-811 (1997)). Sporadic MSI cancers are not restricted to colorectal, gastric or endometrial cancers but may comprise bladder cancer, urinary tract cancer, ovary cancer, prostate cancer, lymphomas, leukemias, glioblastoma, astrocytoma and neuroblastoma.

The normal function of the MMR system is to recognize and repair the erroneous insertions, deletions and misincorporation of bases that arise during DNA replication and recombination, as well as to repair some forms of DNA damage. It is now well established that MMR deficiency is not in itself a direct transforming event and that MSI tumours develop through a distinctive molecular pathway characterized by the genetic instability of numerous microsatellite repeat sequences throughout the genome (Duval and Hamelin, *Cancer research* 62 (9), 2447 (2002)). The large majority of published articles on the mechanisms underlying MSI carcinogenesis have involved the study of colorectal cancer (CRC). These revealed that MSI CRCs comprised a distinctive and alternative group to the major tumour type referred to as CIN (for 'Chromosomal Instability', also called MSS for 'Microsatellite Stable') (Walther et al., *Gut* 57 (7), 941 (2008)). In addition to the genetic instability in coding repeats, MSI tumour cells accumulate hundreds of alterations in non coding microsatellite repeats throughout the genome (Giannini et al., *Oncogene* 23 (15), 2640 (2004)), but the functional consequences of these mutations in carcinogenesis have yet to be thoroughly investigated.

The MSI status of a given tumor may be determined by looking at microsatellite instability in a panel of five genetic microsatellite markers: BAT25, BAT26, NR21, NR24 and NR27. Tumors with instability at two or more of these markers were defined as being MSI-High (MSI-H), whereas those with instability at one marker or showing no instability were respectively defined as MSI-Low (MSI-L) and Microsatellite Stable (MSS) tumors. MSI-H cancers have distinct clinicopathological features from MSI-L and MSS tumors, MSI-L and MSS tumors being considering to have the same clinical and molecular features, and the distinction between MSI-H and MSI-L/MSS tumors is important for their prognosis and treatment (Duval and Hamelin, *Annales de génétique* 45: 71-75 (2002)). For example, it is known that MSI status of colorectal cancers (that is, the classification of a tumor as MSI-H or MSI-L/MSS) is predictive of the benefit of adjuvant-based chemotherapy with fluorouracil in stage II and stage III colon cancers (Ribic et al., *N Engl J Med* 349:247 (2003)). Thus, the identification and classification of colorectal tumors into MSI status provides the medical practitioner with critical information as to patient diagnosis, prognosis, and optimal treatment regimen.

Although MSI cancers are now considered to represent a distinct tumour entity, there is still no specific therapeutic approach that takes into account the unique mode of cell transformation seen within these tumours. Moreover, MSI CRCs have been consistently reported to show a different prognosis and response to chemotherapeutic agents (Sargent et al., *J Clin Onco* 28 (20), 3219 (2010); Zaanan et al., *Ann Oncol* 21 (4), 772 (2010)), which still can not be assessed.

Thus, there is a need to identify markers for prognosing survival of patients affected by cancer, more particularly by cancer liable to have a MSI phenotype and for evaluating their response to the therapy. There is also a need to develop treatments specifically adapted to MSI and MSS cancers, taking their clinical and molecular specificity into account.

DESCRIPTION OF THE INVENTION

The inventors surprisingly identified a mutated form of HSP110 protein, generated from an aberrantly spliced mRNA lacking exon 9 and thus lacking amino acids 381 to 858 of wild-type HSP110, in MSI CRC cell lines and primary tumors or adenoma. The inventors also identified deletions affecting a microsatellite repeat of 17 thymidine nucleotides localized in the splicing acceptor site of intron 8 of the HSPH1 gene, i.e the gene coding the HSP110 protein. It has been found that the length of the deletion affecting the said microsatellite repeat correlates with the level of expression of the mutated HSP110 mRNA or protein, thus suggesting that deletion of the microsatellite repeat is the causative event leading to aberrant expression of the mutated HSP110. Moreover, it has been found that expression of the mutated HSP110 impaired both the normal cellular localization of HSP110 and its interaction with other HSPs, thus abrogating its chaperone activity and its anti-apoptotic function in a dominant negative manner.

It was surprisingly found that the mutated HSP110 has not only lost its anti-apoptotic properties but also associates with the wild-type HSP110, thus blocking the anti-apoptotic function of the wild-type HSP110, in a dose-dependent manner. That is to say, the mutated HSP110 protein is a dominant negative mutant.

Without being bound to any theory, the inventors believe that this pro-apoptotic effect of the mutated HSP110, especially observed when the expression level of the mutated HSP110 is similar or higher to the expression level of wild-type HSP110, is due to the fact that each molecule of mutated HSP110 forms a complex with one molecule of wild-type HSP110, thereby neutralizing wild-type HSP110's activity in a dominant negative manner. Consequently, cells expressing the mutated HSP110 are more sensitive to apoptosis, notably apoptosis induced by chemotherapeutic drugs.

As a consequence, the mutated HSP110 can be administered to a patient suffering from cancer, particularly to a cancer with MSI or MSS phenotype, and more particularly to a colorectal cancer, in order to increase sensitivity to apoptosis and/or to chemotherapeutic drugs.

In addition, it has been found that the expression profile of mutated HSP110 can be used as an early and reliable marker for prognosing the survival and the response to treatment. Indeed, high expression levels of the mutated HSP110 are correlated with a good prognosis and with a positive response to treatment.

DEFINITIONS

The term "wild-type HSP110" refers to the heat-shock 110 kDa protein. An amino acid sequence of wild-type HSP110 is shown as SEQ ID NO: 2 (Swiss-Prot accession number Q92598, update Mar. 8, 2011, version 119). The term "wild-type HSP110" encompasses the protein of SEQ ID NO: 2 (full-length and mature isoforms) as well as homologues in other species, variants obtained by proteolytic processing, splice variants and allelic variants thereof.

The term "cancer" refers to or describes the physiological condition in mammals that is typically characterized by unregulated cell growth. Said cancer may be a sporadic or an hereditary cancer. Said cancer may be an adenoma (i.e. a benign tumor, which may evolve and become malignant) or a malignant tumor (i.e. a primary tumor or a metastatic tumor). Examples of cancer include, but are not limited to, sarcomas, carcinomas, leukemias, lymphomas, germ cells tumors and blastomas.

In a preferred embodiment said cancer is a cancer liable to have a MSI phenotype". "A cancer liable to have a MSI phenotype" refers to a sporadic or hereditary cancer in which microsatellite instability may be present (MSI) or absent (MSS). Detecting whether microsatellite instability is present may for example be performed by genotyping microsatellite markers, such as BAT25, BAT26, NR21, NR24 and NR27, e.g. as described in Buhard et al., *J Clin Oncol* 24 (2), 241 (2006) and in European patent application No. EP 11 305 160.1. A cancer is defined as having a MSI phenotype if instability is detected in at least 2 microsatellite markers. To the contrary, if instability is detected in one or no microsatellite marker, then said cancer has a MSS phenotype.

Examples of cancers liable to have a MSI phenotype include adenoma or primary tumors, such as colorectal cancer (also called colon cancer or large bowel cancer), stomach cancer, endometrial cancer, bladder cancer, urinary tract cancer, ovary cancer, prostate cancer, lymphomas, leukemia, glioblastoma, astrocytoma and neuroblastoma. Preferably, the cancer is a colorectal cancer. Still preferably, the cancer is a stage II or stage III colorectal cancer.

A sporadic cancer liable to have a MSI phenotype may refer to a cancer due to somatic genetic alteration of one of the Mismatch Repair (MMR) genes MLH1, MSH2, MSH6 and PMS2. For example, a sporadic cancer liable to have a MSI phenotype can be a cancer due to de novo bi-allelic methylation of the promoter of MLH1 gene.

An hereditary cancer liable to have a MSI phenotype may refer to a cancer that occurs in the context of Lynch syndrome or Constitutional Mismatch-Repair Deficiency (CMMR-D).

A patient suffering from Lynch syndrome is defined as a patient with an autosomal mutation in one of the 4 genes MLH1, MSH2, MSH6, PMS2.

A patient suffering from CMMR-D is defined as a patient with a germline biallelic mutation in one of the 4 genes MLH1, MSH2, MSH6, PMS2.

By "stage II colorectal cancer", it is meant tumor with no lymph node spreading and no distant invasion (American Joint Comittee on Cancer" 2010, Chap. 14. p. 173-201).

By "stage III colorectal cancer", it is meant it is meant tumor with lymph node spreading (American Joint Comittee on Cancer" 2010, Chap. 14. p. 173-201).

As used herein, the patient is a human or a non-human mammal, in particular a rodent, a feline, a canine, a bovine or an ovine mammal. In a preferred embodiment, the patient is a human patient. More particularly, the patient is a child, an adult, a man or a woman.

By "treatment", it is meant, without limitation, a chemotherapeutic treatment and/or a radiotherapeutic treatment and/or a surgical treatment. As used herein, the term "treatment" encompasses therapeutic methods, e.g. aiming at curing, improving the condition of the patient and/or extending the lifespan of the patient suffering from the cancer. It also encompasses prophylactic methods such as methods aiming at preventing the appearance or the spreading of metastases, as well as methods aiming at preventing a relapse. The chemotherapeutic treatment may for example be performed with an alkylating agent, such as e.g. oxaliplatin. The chemotherapeutic treatment may also be an adjuvant chemotherapeutic treatment, e.g. a chemotherapeutic treatment using 5-fluorouracil agent. In some embodiments, said chemotherapeutic treatment may combine at least 2, 3, 4, 5, 6, 7, 8, 9, 10 or at most 10, 9, 8, 7, 6, 5, 4, 3, 2 agents, such as e.g. a combination of oxaliplatin, 5-fluorouracil and folinic acid, i.e. the FOLFOX treatment, or a combination of 5-fluorouracil and folinic acid, i.e. the FUFOL or LV5FU2 treatment.

As used herein, the term "microsatellite reoeat of 17 thvmidine nudeotides localized in the solicina acceetor site of intron 8 of the oene encodina heat-shock protein 110 (HSP110)" refers to the thymidine repetition comprised between position 73 and position 89 of the sequence of SEQ ID NO: 9: GAAAACCCTGTCCATCCATTGGAATT-GAGTTTTATATTAAAAGATGACTGGGAAGTGT TCATGTGCTCATGATTTTTTTTTTTTTTTAAGTGT-GCAATACTTTCCCCTTTCCCCGG CATTTAAAGTTA-GAGAATTTTCCGTCACAGATGCAGTTCCTTTTCC.

Mutated Heat-shock Protein 110

A first aspect of the invention is a mutated heat-shock protein 110 (HSP110), wherein said protein:

a) does not exhibit chaperone activity and/or is not capable of binding to heat-shock protein 70 (HSP70) and/or to heat-shock protein 27 (HSP27); and b) is capable of binding to a wild-type HSP110 protein of SEQ ID NO: 2.

In a preferred embodiment, the mutated HSP110 protein lacks the domain consisting of amino acids 381 to 858 of SEQ ID NO: 2. In another preferred embodiment, the mutated HSP110 protein is encoded by an mRNA lacking exon 9. Exon 9 of the gene coding for HSP110 is for example described between positions 1536 and 1642 in the NCBI Reference sequence NM_006644.2 (published version at Dec. 27, 2010).

In another preferred embodiment, the mutated HSP110 protein comprises or consists of an amino acid sequence at least 80% identical to SEQ ID NO: 1, preferably at least 80%, 85%, 90%, 95%, 96%, 97%, 98% or 99% to SEQ ID NO: 1. Most preferably, the mutated HSP110 protein comprises or consists of SEQ ID NO: 1.

By a protein having an amino acid sequence at least, for example, 95% "identical" to a query amino acid sequence of the present invention, it is intended that the amino acid sequence of the subject protein is identical to the query sequence except that the subject protein sequence may include up to five amino acid alterations per each 100 amino acids of the query amino acid sequence. In other words, to obtain a protein having an amino acid sequence at least 95% identical to a query amino acid sequence, up to 5% (5 of 100) of the amino acid residues in the subject sequence may be inserted, deleted, or substituted with another amino acid.

In the frame of the present application, the percentage of identity is calculated using a global alignment (i.e., the two sequences are compared over their entire length). Methods for comparing the identity and homology of two or more sequences are well known in the art. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Protein comprising or consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the substitution preferably corresponds to a conservative substitution as indicated in the table below. In a preferred embodiment, the protein comprising or consisting of an amino acid sequence at least 80%, 85%, 90%, 95%, 96%, 97%, 98% or 99% identical to a reference sequence only differs from the reference sequence by conservative substitutions. In another preferred embodiment, the protein comprising or consisting of an amino acid sequence at least 80%, 85%, 90%, 95%, 96%, 97%, 98% or 99% identical to a reference sequence corresponds to a naturally-occurring allelic variant of the reference sequence. In still another preferred embodiment, the protein comprising or consisting of an amino acid sequence at least 80%, 85%, 90%, 95%, 96%, 97%, 98% or 99% identical to a reference sequence corresponds to a homologous sequence derived from another non-human mammalian species than the reference sequence.

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

The mutated HSP110 proteins according to the invention do not exhibit chaperone activity and/or are not capable of binding to heat-shock protein 70 (HSP70) and/or to heat-shock protein 27 (HSP27), but they are capable of binding to a wild-type HSP110 protein of SEQ ID NO: 2.

By "chaperone activity", it is meant, without limitations, the ability to allow protein folding, protein complex formation, transmembrane transport of proteins and targeting some of them to lysosomal degradation. The skilled in the art can easily determine whether the mutated HSP110 possess a chaperone activity. For example, the chaperone activity may be determined using a protein thermolability assay, as described in the paragraph entitled "HSP110 chaperone activity" of the Example 1.

Throughout the present specification, the term "binding" has its usual meaning in the art. In particular, the term "binding" refers to a specific binding, as opposed to a non-specific binding. The skilled in the art can easily determine whether the mutated HSP110 is capable of binding to HSP70, HSP27 and/or wild-type HSP110. For example, capacity of mutated HSP110 to bind to HSP70, HSP27 and/or wild-type HSP110 may be determined by immunoprecipitation assays as described in the paragraph entitled "Immunoprecipitation and Western-blotting" of Example 1.

The invention further pertains to fragments of the mutated HSP110 protein comprising or consisting of an amino acid sequence at least 80% identical to SEQ ID NO: 1, preferably at least 80%, 85%, 90%, 95%, 96%, 97%, 98%, 99% or 100% identical to SEQ ID NO: 1, provided said fragments retain the same biological activity as the mutated HSP110 protein (i.e. they do not exhibit chaperone activity and/or are not capable of binding to HSP70 and/or HSP27, but they are capable of binding to a wild-type HSP110 protein of SEQ ID NO: 2). These fragments preferably comprise or consist of at least 5 contiguous (consecutive) amino acids of the mutated HSP110 protein described hereabove. Preferably, the fragment comprises or consists of at least 6, 8, 10, 12, 15, 18, 20, 25, 30, 50, 75, 100, 125, 150, 200, 250, 275, 300, 325, 350, 375 consecutive amino acids of mutated HSP110. Also preferably, the fragment is a peptide, i.e. it consists of at most 50 amino acids.

The invention also pertains to peptido-mimetics of the mutated HSP110 protein according to the invention, or of fragments. As used herein, the term <<peptido-mimetic>> refers to a compound containing non-peptidic structural elements that mimics the biological action of a mutated HSP110 protein according to the invention. Methods for designing and synthesizing peptidomimetics of a given protein are well-known in the art and include e.g. those described in Ripka and Rich, *Curr Opin Chem Biol* 2(4): 441-52 (1998) and in Patch and Barron, *Curr Opin Chem Biol*6(6):872-7 (2002).

The present invention is further directed to an isolated nucleic acid comprising or consisting of a sequence encoding the mutated HSP110 as described hereabove.

In a preferred embodiment, the isolated nucleic acid comprises or consists of nucleotidic sequence at least 80% identical to SEQ ID NO: 3, preferably at least 85%, 90%, 91%, 92%, 93%, 94%, 95%, 96%, 97%, 98%, 99% or 100% identical to SEQ ID NO: 3, and more preferably the isolated nucleic acid comprises or consists of SEQ ID NO: 3.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA round, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

Another aspect of the invention provides vectors, e.g., expression vectors, comprising a nucleic acid molecule of the invention. In another embodiment the invention provides a host cell (e.g. bacterial, yeast, fungal or mammal host cell) containing and/or expressing such a vector. The invention also provides methods for producing a recombinant mutated HSP110 protein according to the invention by culturing, in a suitable medium, such a host cell of the invention. Said method may further comprise the step of purifying the recombinant mutated HSP110 according to the invention, and optionally formulating it into a pharmaceutical composition.

Such nucleic acids are intended to be administered to a patient using an adenoviral vector, and/or in the frame of a gene therapy.

The invention also relates to an antibody that specifically recognizes a mutated HSP110 protein according to the invention.

In some embodiments, said antibody is able to recognize a mutated HSP110 protein according to the invention, but is not able to recognize a wild-type HSP110 protein, such as a wild-type HSP110 protein of sequence SEQ ID NO: 2.

Preferably, said antibody is able to recognize a mutated HSP110 protein of sequence SEQ ID NO: 1.

An antibody which "specifically binds" to a target protein binds to said target protein with greater affinity and/or avidity than to other proteins or epitopes, even closely related proteins or epitopes. Preferably, an antibody of the invention binds to a mutated HSP110 protein as described herein, such as a protein comprising or consisting of the sequence of SEQ ID NO: 1, with greater affinity and/or avidity than it binds to a wild-type HSP110 protein of sequence SEQ ID NO: 2. Typically, the antibody binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by surface plasmon resonance (SPR) technology in a BIAcore 3000 instrument using mutated HSP110 as the ligand and the antibody as the analyte. The antibody may bind to the target with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., wild-type HSP110, BSA, casein). The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The phrases "an antibody recognizing an antigen" and "an antibody specific for an antigen" are used interchangeably herein with the term "an antibody which binds specifically to an antigen".

The term "$k_d$" (sec$^{-1}$), as used herein, is intended to refer to the dissociation equilibrium rate constant of a particular antibody-antigen interaction. Said value is also referred to as the $k_{off}$ value.

The term "$k_a$" (M$^{-1}$×sec$^{-1}$), as used herein, is intended to refer to the association equilibrium rate constant of a particular antibody-antigen interaction.

The term "$K_D$" (M), as used herein, is intended to refer to the dissociation equilibrium constant of a particular antibody-antigen interaction.

The term "$K_A$" (M$^{-1}$), as used herein, is intended to refer to the association equilibrium constant of a particular antibody-antigen interaction and is obtained by dividing the $k_a$ by the $k_d$.

As used herein, "isotype" refers to the antibody class (for instance IgG1, gG2, IgG3, IgG4, IgD, IgA, IgE, or IgM) that is encoded by heavy chain constant region genes.

The term "antibody" refers to immunoglobulin molecules and immunologically active portions of immunoglobulin molecules, i.e., molecules that contain an antigen binding site which immunospecifically binds an antigen. As such, the term antibody encompasses not only whole antibody molecules, but also antibody fragments as well as variants of antibodies, including derivatives such as humanized antibodies. In natural antibodies, two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non hypervariable or framework regions (FR) influence the overall domain structure and hence the combining site. Complementarity determining regions (CDRs) refer to amino acid sequences which, together, define the binding affinity and specificity of the natural Fv region of a native immunoglobulin binding-site. The light and heavy chains of an immunoglobulin each have three CDRs, designated L-CDR1, L-CDR2, L-CDR3 and H-CDR1, H-CDR2, H-CDR3, respectively. Therefore, an antigen-binding site includes six CDRs, comprising the CDR set from each of a heavy and a light chain V region.

Framework Regions (FRs) refer to amino acid sequences interposed between CDRs, i.e. to those portions of immunoglobulin light and heavy chain variable regions that are relatively conserved among different immunoglobulins in a single species, as defined by Kabat, et al (Sequences of Proteins of Immunological Interest (National Institutes of Health, Bethesda, Md., 1991). As used herein, a "human framework region" is a framework region that is substantially identical (about 85%, or more, in particular 90%, 95%, or 100%) to the framework region of a naturally occurring human antibody.

The term "monoclonal antibody" or "mAb" as used herein refers to an antibody molecule of a single amino acid composition, that is directed against a specific antigen and which may be produced by a single clone of B cells or hybridoma. Monoclonal antibodies may also be recombinant, i.e. produced by protein engineering.

The term "chimeric antibody" refers to an engineered antibody which comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens.

The term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody".

"Antibody fragments" comprise a portion of an intact antibody, preferably the antigen binding or variable region of the intact antibody. Examples of antibody fragments include Fv, Fab, F(ab')2, Fab', dsFv, scFv, sc(Fv)2, diabodies and multispecific antibodies formed from antibody fragments.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab" refers to an antibody fragment having a molecular weight of about 50,000 and antigen binding activity, which is obtained by cutting a disulfide bond of the hinge region of the F(ab')$_2$.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques. "dsFv" is a VH::VL heterodimer stabilised by a disulphide bond. Divalent and multivalent antibody fragments can form either spontaneously by association of monovalent scFvs, or can be generated by coupling monovalent scFvs by a peptide linker, such as divalent sc(Fv)$_2$.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Prognostic Methods and Uses According to the Invention

It has been found that deletion of nucleotides in a microsatellite repeat of 17 thymidines localized in the splicing acceptor site of intron 8 of the gene encoding HSP110 and that a mutated HSP110 are present in MSI CRCs, and that the length of the deletion influences the expression of the mutated HSP110. More precisely, it has been found that a deletion of 3 thymidines correlated with a low expression of a mutated HSP110 mRNA and protein, and that a deletion of 8 thymidines correlates with a high expression of a mutated HSP110 mRNA and protein. It has also been found that the level of expression of the mutated HSP110 is correlated with the prognosis of survival and/or of response to treatment. Moreover, it has been found that the mutated HSP110 is able to form a complex with the wild-type HSP110 in a dominant negative manner, thus blocking its anti-apoptotic effect. More specifically, it has been found that the mutated HSP110 protein is able to form a complex with the wild-type HSP110 protein in a dominant negative manner, thus blocking its anti-apoptotic effect. Consequently, tumor cells expressing a high level of mutated HSP110, and which are usually tumors with a MSI phenotype, are more sensitive to apoptosis, notably to apoptosis induced by chemotherapeutic treatment.

It has also been found that the length of the microsatellite repeat of 17 thymidines localized in the splicing acceptor site of intron 8 of the gene encoding HSP110 is correlated with the prognosis of survival and/or of response to treatment. It has been found that patients suffering from stage III colorectal cancer with MSI phenotype and carrying large deletions have a good prognosis of survival. Moreover, it has been found that patients suffering from stage II or stage III colorectal cancer with MSI phenotype, treated with chemotherapy and carrying large deletions, i.e. deletion of at least 5 thymidines, in said microsatellite repeat, also have a good prognosis of survival and/or of response to the chemotherapy.

Naturally, the size of the deletion may be determined by determining the length of the thymidine repetition of the microsatellite repeat of 17 thymidines, i.e. the number of thymidines in the repetition.

As used herein, determining the length of the thymidines repetition of said microsatellite repeat of 17 thymidine nucleotides is equivalent to determining the length of the thymidines deletion within said microsatellite repeat of 17 thymidine nucleotides.

Therefore, an aspect of the invention is directed to the use of the microsatellite repeat of 17 thymidines localized in the splicing acceptor site of intron 8 of the gene encoding HSP110 and/or the mutated HSP110 (i.e. mRNA and/or protein) and/or fragments as described hereabove, as a biomarker for prognosing survival and/or the response to a treatment of a patient suffering from a cancer, in particular from a cancer liable to have MSI phenotype. Increased amount of mutated HSP110 (i.e. mRNA and/or protein) is indicative of a good prognosis of survival and/or of response to the treatment. Small thymidines deletions, i.e. 3 or 4 thymidines, is indicative of bad prognosis of survival and/or of response to the treatment, and large thymidines deletions, i.e. 5 to 8 thymidines, is indicative of good prognosis of survival and/or of response to the treatment.

In some embodiments, the invention is also directed to the use of the microsatellite repeat of 17 thymidines localized in the splicing acceptor site of intron 8 of the gene encoding HSP110 and/or the mutated HSP110 nucleic acid as described hereabove and/or the HSP110 protein and/or fragments thereof as described hereabove, as a biomarker for prognosing survival and/or the response to a treatment of a patient suffering from a cancer, in particular from a cancer liable to have MSI phenotype.

In some embodiments, small thymidines deletions equal or inferior to 4 deletions is indicative of bad prognosis of survival and/or of response to the treatment, and large thymidines deletions, i.e. equal or superior to 5 thymidines, is indicative of good prognosis of survival and/or of response to the treatment.

By "use as a biomarker" is meant an in vitro use, wherein mutated HSP110 may be detected e.g. using ligands, antibodies, probes and/or primers and wherein the length of the thymidines deletion may be detected by genotyping or sequencing. Therefore, the invention is also directed to the use of means for detecting the length of the thymidines deletion of the microsatellite repeat and/or mutated HSP110 in a biological sample of a patient suffering from a cancer.

The present invention is further directed to an in vitro method for prognosing survival and/or the response to a treatment of a patient suffering from a cancer, said method comprising the steps of:
  a) measuring the expression level of a mutated heat-shock protein 110 (HSP110) as described hereabove in a biological sample of said patient; and/or
  b) determining the length of thymidine repetition of a microsatellite repeat of 17 thymidine nucleotides localized in the splicing acceptor site of intron 8 of the gene encoding heat-shock protein 110 (HSP110) in a biological sample of said patient;
  c) and correlating the level of expression measured at step a) and/or the length of the thymidine repetition identified at step b) with the prognosis of said patient, thereby deducing the prognosis of said patient.

In some embodiments, the method for prognosing survival and/or response to a treatment of a patient suffering from a cancer comprises the steps of:
  a) measuring the expression of a mutated HSP110 protein according to the invention in a biological sample of said patient; and/or
  b) measuring the expression of a mutated HSP110 mRNA according to the invention in a biological sample of said patient; and/or
  c) determining the length of thymidine repetition of a microsatellite repeat of 17 thymidine nucleotides localized in the splicing acceptor site of intron 8 of the gene encoding heat-shock protein 110 (HSP110) in a biological sample of said patient;
  d) and correlating the level of expression measured at step a) and/or b) and/or the length of the thymidine repetition identified at step c) with the prognosis of said patient, thereby deducing the prognosis of said patient.

Indeed, as demonstrated in the examples, high expression level of mutated HSP110 is correlated with a good prognosis of survival and/or of response to a treatment.

In addition, as demonstrated in the examples, small thymidine deletions within the repetition (i.e. 3 or 4 thymidines, or fewer), is indicative of bad prognosis of survival and/or of response to the treatment, and large thymidine deletions within the repetition (i. e. 5 to 8 thymidines, or more), is indicative of good prognosis of survival and/or of response to the treatment. That is to say, the deletion of at least 5 thymidines within the repetition is indicative of a good prognosis of survival and/or of response to the treatment. In some embodiments, the deletion of at least 5 thymidines within the repetition indicates that the patient has a low risk of relapse after treatment in comparison to a patient with small thymidine deletions within the repetition, or that the patient will not relapse after treatment. In some embodiments, the deletion of 5 thymidines or more within the repetition indicates that the patient is more likely to respond to treatment in comparison to a patient with small thymidine deletions within the repetition.

In a specific embodiment, the method according to the invention comprises the steps of:
a) measuring the expression of a mutated HSP110 as described hereabove in a biological sample of said patient;
b) measuring the expression of a mutated HSP110 as described hereabove in a negative control sample;
wherein a significantly higher expression of mutated HSP110 measured at step a) in comparison to the expression measured at step b) is indicative of a good prognosis of survival and/or of response to the treatment.

The higher expression is considered to be statistically significant if the expression level of mutated HSP110 in the biological sample of the patient is increased 2, 3, 4, 5, 6, 7, 8, 9 or 10 fold, or by at least 30%, 40%, 50%, 60%, 70% or 75% compared with the level of mutated HSP110 in the negative control sample. In a preferred embodiment, the higher expression is considered to be statistically significant if the expression level of mutated HSP110 in the biological sample of the patient is increased of at least 75%.

In another specific embodiment, the method according to the invention comprises the steps of:
a) measuring the expression of a mutated HSP110 as described hereabove in a biological sample of said patient;
b) measuring the expression of a wild-type HSP110 in said biological sample;
c) comparing the expression measured at step (a) and (b), thereby deducing the prognosis of said patient.

Indeed, when mutated HSP110 is expressed at similar or higher levels than wild-type HSP110, the prognosis will be good. In particular, in the frame of this embodiment, an expression level of mutated HSP110 superior or equal to 50%, 60%, 70%, 75%, 80%, 90% or 100% of the expression level of wild-type HSP110 may for example be indicative of a good prognosis and/or that the patient is likely to respond to a treatment.

Comparing the expression measured at steps a) and b) may be performed by calculating an expression ratio, for example with the formula: Ratio=expression level of mutated HSP110/expression level of wild-type HSP110. An expression ratio superior or equal to 0.75 may for example be indicative of a good prognosis and/or that the patient is likely to respond to a treatment.

In still another specific embodiment, the method according to the invention comprises the steps of:

a) measuring the expression of mutated HSP110 and wild-type HSP110 as described hereabove in a biological sample of said patient;
b) analyzing expression obtained at step a) to generate an expression ratio;
c) measuring the expression of mutated HSP110 and wild-type HSP110 as described hereabove in a negative control sample;
d) analyzing expression obtained at step c) to generate an expression ratio;
wherein a significantly higher expression ratio generated at step b) in comparison to the expression ratio generated at step d) indicates that the patient has a good prognosis of survival and/or that the patient is likely to respond to the treatment.

The higher expression ratio is considered to be statistically significant if the ratio generated at step (b) is increased at least 2, 3, 4, 5, 6, 7, 8, 9 or 10 fold compared with the ratio generated at step (d). In a preferred embodiment, the ratio is considered to be statistically significant if the expression ratio in the biological sample of the patient is increased at least 7.5 fold.

Methods for measuring the expression level of mutated HSP110 and wild-type HSP110 are well-known in the art. The expression level may be measured either by quantifying mRNAs, or by quantifying proteins. Suitable methods include, e.g., immunochemistry, Elisa, Western blotting, flow cytometry, Northern blotting, PCR (e.g. RT-PCR and QRT-PCR), ligase chain reaction (LCR), transcription-mediated amplification (TMA), strand displacement amplification (SDA), nucleic acid sequence based amplification (NASBA), Amplification Refractory Mutation System (ARMS), and High Resolution Melting analysis (HRM PCR).

The amplification refractory mutation system (ARMS) is an amplification strategy in which a polymerase chain reaction (PCR) primer is designed in such a way that it is able to discriminate among templates that differ by a single nucleotide residue. ARMS has also been termed allele-specific PCR or PCR amplification of specific alleles (PASA). Thus, an ARMS primer can be designed to amplify a specific member of a multi-allelic system while remaining refractory to amplification of another allele that may doffer by as little as a single base from the former. The main advantage of ARMS is that the amplification step and the diagnostic steps are combined, in that the presence of an amplified product indicates the presence of a particular allele and vice versa. For routine diagnosis, this characteristic of ARMS means that it is a very time-efficient method.

High Resolution Melt (HRM) analysis is a powerful technique in molecular biology for the detection of mutations, polymorphisms and epigenetic differences in double-stranded DNA samples. HRM analysis is performed on double stranded DNA samples. Typically polymerase chain reaction (PCR) will be used prior to HRM analysis to amplify the DNA region in which the mutation of interest lies. Essentially the PCR process turns a tiny amount of the region of DNA of interest into a large amount, so the quantities are large enough for better analysis. In the tube there are now many of copies of the region of DNA of interest. This region that is amplified is known as the amplicon. After the PCR process the HRM analysis begins. The process is simply a precise warming of the amplicon DNA from around 50° C. up to around 95° C. At some point during this process, the melting temperature of the amplicon is reached and the two strands of DNA separate or "melt" apart. The secret of HRM is to monitor this process happening in real-time. This is achieved by using a fluorescent dye. The dyes that are used for HRM are known as intercalating dyes and have a unique property. They bind specifically to double-stranded DNA and when they are bound they fluoresce brightly. In the absence of double stranded DNA they have nothing to bind to and they only fluoresce at a low level. At the beginning of the HRM analysis there is a high level of fluorescence in the sample because of the billions of copies of the ampicon. But as the sample is heated up and the two strands of the DNA melt apart, presence of double stranded DNA decreases and thus fluorescence is reduced. The HRM machine has a camera that watches this process by measuring the fluorescence. The machine then simply plots this data as a graph known as a melt curve, showing the level of fluorescence vs the temperature. The melting temperature of the amplicon at which the two DNA strands come apart is entirely predictable. It is dependent on the sequence of the DNA bases. If you two samples from two different people are compared, they should give exactly the same shaped melt curve. However if one of the people has a mutation in the amplified DNA region, then this will alter the temperature at which the DNA strands melt apart. So now the two melt curves appear different. The difference may only be tiny, perhaps a fraction of a degree, but because the HRM machine has the ability to monitor this process in "high resolution", it is possible to accurately document these changes and therefore identify if a mutation is present or not.

The above methods allow predicting response to any treatment. In a specific embodiment, said treatment is a treatment with an alkylating agent such as e.g. oxaliplatin, or a treatment with 5-fluorouracil, or the FOLFOX treatment, or the FUFOL treatment.

In a preferred embodiment, measuring the expression level of mutated HSP110 is performed by QRT-PCR using a forward primer, a reverse primer and a probe, which can be used to detect the presence of the mutated HSP110. In particular, the forward primer may have the sequence 5'-GCTACACGAATTCCAGCTGTGA-3' (SEQ ID NO: 4), the reverse primer may have the sequence 5'-GAGCAGCATG-GTTTCGACTAAA-3' (SEQ ID NO: 5), and the fluorescent probe which specifically hybridizes to the mutated HSP110 may be the HSP110delE9 probe of sequence 5'-ATGTG-CATTACAGTGTTC-3' (SEQ ID NO: 6).

In another preferred embodiment, measuring the expression level of wild-type HSP110 is performed by QRT-PCR using a forward primer, a reverse primer and a probe, which can be used to detect the presence of the wild-type HSP110. In particular, the forward primer may have the sequence SEQ ID NO: 4, the reverse primer may have the sequence SEQ ID NO: 5, and the fluorescent probe which specifically hybridizes to the mutated HSP110 may be the HSP110wt probe of sequence 5'-TACAGTGTGCAATACTT-3' (SEQ ID NO: 7).

Preferably, the probes are labelled with at least one fluorescent label or dye. The fluorescent dye can be a wide variety of dyes known in the art.

More preferably, the probes are labelled with a reporter dye and a quencher dye. Still more preferably, the probes are labelled at their 5' end with the reporter dye and at their 3' end with the quencher dye. The reporter dye may be a fluorescent dye. The quencher dye may be a non-fluorescent dye or a fluorescent dye.

In a more preferred embodiment, the HSP110delE9 probe is labelled with the reporter dye VIC™ (fluorescent dye) at its 5' end and with the quencher dye at its 3' end, and the HSP110wt probe is labelled with the reporter dye 6-FAM™ (6-carboxyfluorescein) at its 5' end and with the quencher dye at its 3' end.

In a preferred embodiment, the QRT-PCR comprises an initial denaturation step followed by cycles of denaturation-annealing-elongation steps.

The initial denaturation step may be performed under heating conditions ranging from 90° C. to 105° C., during 15 sec to 15 min. Preferably, the heating conditions range from 92° C. to 102° C., more preferably from 95° C. to 100° C., still more preferably the heating conditions are at 95° C. Preferably, the initial denaturation step is performed during 1 min to 15 min, more preferably during 8 min to 12 min, still more preferably during 5 min to 10 min, and still more preferably the initial denaturation step is performed during 10 min.

In a preferred embodiment, the initial denaturation step is performed at 95° C. during 10 min.

Each cycle of denaturation-annealing-elongation step includes a denaturation phase under heating conditions, followed by an annealing phase performed under conditions which allow the hybridization of the primers and the probe to the sequence to be amplified, and an elongation phase performed under conditions which allow the polymerase to synthesize an extension product from each primer that is annealed to the sequence to be amplified.

The denaturation phase may be performed between 90° C. to 105° C., preferably 92° C. to 100° C., more preferably between 94° C. to 98° C., during 10 sec to 4 min, preferably during 10 sec to 2 min, more preferably during 15 sec to 1 min.

The annealing phase may be performed between 35° C. and 70° C., preferably between 40° C. to 65° C., more preferably between 45° C. to 60° C., still more preferably between 50° C. to 60° C., during 10 sec to 2 min, preferably during 20 sec to 1.5 min, more preferably during 30 sec to 1 min.

The elongation phase may be performed between 40° C. and 80° C., preferably between 50° C. to 75° C., more preferably between 55° C. to 65° C., still more preferably between 58° C. to 62° C., during 10 sec to 5 min, preferably during 20 sec to 3 min, more preferably during 30 sec to 1 min, still more preferably during 30 sec to 45 sec.

In a preferred embodiment, the denaturation phase is performed at 95° C. during 15 sec, the annealing phase and the elongation phase are combined and performed at 60° C. during 1 min. The denaturation-annealing-elongation step may be repeated during 30 to 60 cycles, preferably during 35 to 50 cycles, more preferably during 40 to 45 cycles. Still more preferably, the denaturation-annealing-elongation step is repeated during 40 cycles.

Alternatively, measuring the expression of mutated HSP110 can be performed by western blot or by immunohistochemistry.

As used herein, western blot refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies. Preferably, the antibody used for detecting either mutated HSP110 and wild-type HSP110 may recognize the N-terminal part of the proteins. For example, such an antibody may be the rabbit polyclonal antibody ab24503 from Abcam®. The wild-type HSP110 may also be recognized using the rabbit polyclonal antibody SPA-11101 from Stressgen®.

Preferably, measuring the expression level of mutated HSP110 and wild-type HSP110 in the methods according to the invention are performed using the same technique. For instance, if the measure of expression level of mutated HSP110 is performed by QRT-PCR, the measure of expression level of wild-type HSP110 is performed by QRT-PCR.

More preferably, measuring the expression level of mutated HSP110 and wild-type HSP110 is performed in a competitive manner, i.e. measuring the expression level of mutated HSP110 and wild-type HSP110 is performed simultaneously in the same biological sample. In particular, measuring the expression level of mutated HSP110 and wild-type HSP110 is performed by QRT-PCR in a competitive manner using forward and reverse primers as described above which are able to hybridize to mutated HSP110 and wild-type HSP110, and two probes, each of them being able to hybridize specifically to mutated HSP110 or to wild-type HSP110 as described above. In a preferred embodiment, the QRT-PCR comprises an initial denaturation step followed by cycles of denaturation-annealing-elongation steps as described above.

In another preferred embodiment, measuring the expression of mutated HSP110 and of wild-type HSP110 may be performed at the protein level.

The expression ratio may be calculated using any method well-known in the art. Preferably, the expression ratio is obtained as follows:
measuring the expression of mutated HSP110 as described above by QRT-PCR, in a biological sample of said patient, in order to obtain a Ct value;
measuring the expression of wild-type HSP110 as described above by QRT-PCR, in a biological sample of said patient, in order to obtain a Ct value;
calculating the expression ratio (E) using the formula
$E=2^{-(wild-typeHSP110Ct-mutesdHSP110Ct)}$.

As used herein, the biological sample may consist of a blood sample, a serum sample, a plasma sample, a feces sample or a biopsy of a cancer. Preferably the biological sample may consist of a biopsy of an adenoma or a primary cancer. Still more preferably the biological sample may consist of a biopsy of an adenoma or a primary cancer selected from the group consisting of colorectal cancer, stomach cancer, endometrial cancer, bladder cancer, urinary tract cancer, ovary cancer, prostate cancer, lymphomas, leukemias, glioblastoma, astrocytoma and neuroblastoma. Preferably, the biological sample is a biopsy of a colorectal cancer.

When a negative control sample is used, the negative control sample may e.g. correspond to a tissue sample from a healthy or MSS individual (preferably from the same tissue as the cancer cells), to a sample of healthy tissue from the patient (e.g. healthy tissue surrounding the cancerous tissue), or to a sample comprising an amount of mutated and/or wild-type HSP110 that is indicative of the expression level of mutated and/or wild-type HSP110 in a healthy or MSS individual. In a specific embodiment, the negative control sample is the same type of sample than the biological sample of the patient. For example, if the biological sample of the patient is blood, the negative control sample is blood. In another example, if the biological sample of the patient is a biopsy of a colorectal cancer, the negative control sample is a biopsy of a colorectal cancer with microsatellite stability (MSS) phenotype.

In some embodiments, the method according to the invention comprises the steps of determining the length of the thymidine repetition of a microsatellite repeat of 17 thymidine nucleotides localized in the splicing acceptor site of intron 8 of the gene encoding heat-shock protein 110 (HSP110) in a biological sample of said patient, wherein the identification of a deletion of 5 thymidines or more within the repetition is indicative of a good prognosis of survival and/or of response to the treatment.

Determining the length of said thymidine repetition by may be performed by methods known by the skilled in the art. For instance, it may be performed by genotyping. Genotyping the microsatellite repeat of 17 thymidine nucleotides may be performed by methods known by the skilled in the art. For instance, genotyping as described in paragraph "Mutation analysis" of Example 1 or as described in paragraph "Diagnostic method according to the invention" of the description. Genotyping the microsatellite repeat of 17 thymidine nucleotides may be performed by methods known by the skilled in the art. For instance, genotyping the microsatellite repeat of 17 thymidine nucleotides may be performed by amplifying the said microsatellite repeat and isolating the amplification products by capillary electrophoresis. Amplification of said microsatellite repeat can be performed using conventional polymerase chain reaction (PCR) techniques as described in paragraph "Mutation analysis" of Example 1. Suitable methods may also include Amplification Refractory Mutation System (ARMS), and High Resolution Melting analysis (HRM PCR).

In some embodiments, said patient is a patient suffering from a stage II or stage III colorectal cancer with MSI phenotype, and preferably suffering from a stage III colorectal cancer with MSI phenotype. In some embodiments, said patient is a patient that received a chemotherapeutic treatment, such as an adjuvant chemotherapeutic treatment. In a preferred embodiment, said patient is a patient suffering from a stage II or stage III colorectal cancer with MSI phenotype that received an adjuvant chemotherapeutic treatment.

Diagnostic Methods According to the Invention

The inventors surprisingly found that a microsatellite repeat of 17 thymidine nucleotides located in the splicing acceptor site of intron 8 of the HSPH1 gene (NCBI Gene ID: 10808) coding for the HSP110 protein was almost always mutated in MSI CRC cell lines and primary tumors. Moreover, said microsatellite repeat is also frequently mutated in MSI adenoma. Thus said microsatellite repeat analysis may be used in order to diagnose the MSI phenotype in adenoma and primary tumors at very early stage, when diagnostic methods are inefficient.

Thus, the invention also provides an in vitro method for diagnosing the microsatellite instability phenotype (MSI) of a tumor, said method comprising the steps of:
a) genotyping the microsatellite repeat of 17 thymidine nucleotides localized in the splicing acceptor site of intron 8 of the gene encoding heat-shock protein 110 (HSP110) in a biological sample of a patient likely to be affected by a cancer with MSI phenotype;
b) detecting the presence or absence of instability on said microsatellite repeat,
wherein the detection of instability on said microsatellite repeat in the biological sample of the patient indicates that the patient suffers from a cancer with MSI phenotype.

As used herein, the biological sample may be cultured cells or cultured immortalized cells, and/or a biopsy of an adenoma or a primary tumor selected in the group consisting of colorectal cancer, stomach cancer, endometrial cancer, bladder cancer, urinary tract cancer, ovary cancer, prostate cancer, lymphomas, leukemias, glioblastoma, astrocytoma and neuroblastoma. Preferably, the biological sample is a biopsy of colorectal cancer.

Genotyping the microsatellite repeat of 17 thymidine nucleotides may be performed by methods known by the skilled in the art. For instance, genotyping the microsatellite repeat of 17 thymidine nucleotides may be performed by amplifying the said microsatellite repeat and isolating the amplification products by capillary electrophoresis. Amplification of said microsatellite repeat can be performed using conventional polymerase chain reaction (PCR) techniques as described in paragraph "Mutation analysis" of Example 1. Suitable methods may also include Amplification Refractory Mutation System (ARMS), and High Resolution Melting analysis (HRM PCR).

In a preferred embodiment, the forward primer and the reverse primer for microsatellite repeat genotyping have respectively the sequences 5'-CCCTGTCCATCCATTG-GAATTGA-3' (SEQ ID NO: 10) and 5'-GGAACTG-CATCTGTGACGGAA-3' (SEQ ID NO: 11).

In a preferred embodiment, amplification of the microsatellite markers comprises an initial denaturation step followed by cycles of denaturation-annealing-elongation steps and a final elongation step.

The initial denaturation step may be performed under heating conditions ranging from 90° C. to 105° C., during 15 sec to 5 min. Preferably, the heating conditions range from 92° C. to 102° C., more preferably the heating conditions are at 94° C. Preferably, the initial denaturation step is performed during 20 sec to 2 min, more preferably during 25 sec to 1 min and still more preferably the initial denaturation step is performed during 30 sec.

In a preferred embodiment, the initial denaturation step is performed at 94° C. during 30 sec.

Each cycle of denaturation-annealing-elongation step includes a denaturation phase under heating conditions, followed by an annealing phase performed under conditions which allow the hybridization of the primers to the sequence to be amplified, and an elongation phase performed under conditions which allow the polymerase to synthesizes an extension product from each primer that is annealed to the sequence to be amplified.

The denaturation phase may be performed between 90° C. to 105° C., preferably 92° C. to 100° C., more preferably between 94° C. to 98° C., during 10 sec to 4 min, preferably during 10 sec to 2 min, more preferably during 15 sec to 1 min.

The annealing phase may be performed between 35° C. and 70° C., preferably between 40° C. to 65° C., more preferably between 45° C. to 60° C., still more preferably between 50° C. to 60° C., during 10 sec to 2 min, preferably during 20 sec to 1.5 min, more preferably during 25 sec to 45 sec.

The elongation phase may be performed between 40° C. and 80° C., preferably between 50° C. to 75° C., more preferably between 60° C. to 72° C., during 10 sec to 5 min, preferably during 20 sec to 3 min, more preferably during 40 sec to 2 min, still more preferably during 30 sec to 1 min.

In a preferred embodiment, the denaturation phase is performed at 94° C. during 30 sec, the annealing phase is performed at 57° C. during 30 sec and the elongation phase is performed at 72° C. during 1 min. The denaturation-annealing-elongation step may be repeated during 30 to 60 cycles, preferably during 32 to 45 cycles, more preferably during 35 to 42 cycles. Still more preferably, the denaturation-annealing-elongation step is repeated during 40 cycles.

The final elongation step may be performed between 40° C. and 80° C., preferably between 50° C. to 75° C., more preferably between 60° C. to 72° C., during 1 min to 10 min, preferably during 3 min to 8 min, and more preferably during 5 min to 7 min.

In a preferred embodiment, the final elongation step is performed at 72° C. during 7 min.

By "instability" is meant a deletion or an addition of the repeated pattern of thymidine nucleotide.

In a particular embodiment, instability is present when a deletion or an addition of at least one nucleotide is detected in the said biological sample. Preferably, instability is present when a deletion of at least 3 thymidine nucleotides is detected in said biological sample. More preferably, instability is present when a deletion of 3 to 8 thymidine nucleotides is detected in said biological sample.

The invention also provides an in vitro method for diagnosing the microsatellite instability phenotype (MSI) of a tumor, said method comprising the steps of:
a) detecting the presence or absence of instability on the microsatellite repeat of 17 thymidine nucleotides localized in the splicing acceptor site of intron 8 of the gene encoding heat-shock protein 110 (HSP110) in a biological sample of a patient likely to be affected by a cancer with MSI phenotype;
b) detecting the presence or absence of instability on at least one microsatellite selected in the group consisting of the microsatellites BAT26, NR21, NR27, NR24 and BAT25 in a biological sample of a patient likely to be affected by a cancer with MSI phenotype;
wherein the detection of instability on said microsatellite repeat at step a) and the detection of instability on at least one microsatellite repeat at step b) in the biological sample of the patient indicates that the patient suffers from a cancer with MSI phenotype.

The biological sample may be cultured cells or cultured immortalized cells, and/or a biopsy of an adenoma or a primary tumor selected in the group consisting of colorectal cancer, stomach cancer, endometrial cancer, bladder cancer, urinary tract cancer, ovary cancer, prostate cancer, lymphomas, leukemias, glioblastoma, astrocytoma and neuroblastoma. Preferably, the biological sample is a biopsy of colorectal cancer.

In some embodiments, the detection of instability on the microsatellite repeat of 17 thymidine nucleotides localized in the splicing acceptor site of intron 8 of the gene encoding HSP110 and on at least 2, 3, 4, or 5 microsatellite repeats selected in the group consisting of the microsatellite repeats BAT26, NR21, NR27, NR24 and BAT25, indicates that the patient suffers from a cancer with MSI phenotype.

Preferably, the detection of instability on the microsatellite repeat of 17 thymidine nucleotides localized in the splicing acceptor site of intron 8 of the gene encoding HSP110 and on the five microsatellite repeats BAT26, NR21, NR27, NR24 and BAT25, indicates that the patient suffers from a cancer with MSI phenotype.

The BAT26 microsatellite marker is a 26A repeat localized in the intron 5 of the hMSH2 gene, and is found for instance between positions 16298 and 16323 of the NCBI Reference Sequence NG_0007110.1. More preferably, the BAT26 microsatellite marker has a repeated pattern comprised between 20A to 26A.

The NR21 microsatellite marker is a 21T repeat localized in the 5' untranslated region of the SLC7A8 gene, and is found for instance between positions 483 and 503 of the NCBI Reference Sequence NM_012244.2. More preferably, the NR21 microsatellite marker consists of a repeated pattern comprised between 16T to 21T.

The NR27 microsatellite marker is a 26A repeat localized in the 5' untranslated region of the BIRC3 gene, and is found for instance between positions 1031 and 1056 of the NCBI Reference Sequence NM_001165.3. More preferably, the NR27 microsatellite marker consists of a repeated pattern comprised between 23A to 26A.

The NR24 microsatellite marker is a 23T repeat localized in the 3' untranslated region of the 2NF2 gene, and is found for instance between positions 3248 and 3270 of the NCBI Reference Sequence NM_021088.2. More preferably, the NR24 microsatellite marker consists of a repeated pattern comprised between 18T to 23T.

The BAT25 microsatellite marker is a 25T repeat localized in the intron 16 of the c-KIT gene, and is found for instance between positions 74118 and 74142 of the NCBI Reference Sequence NG_007456.1. More preferably, the BAT25 microsatellite marker consists of a repeated pattern comprised between 19T to 25T.

According to the present invention, in step a) and b) detection of the presence or absence of instability may be performed by any method well-known in the art. For example, detection of the presence or absence of instability is performed by sequencing or genotyping. Suitable methods may also include Amplification Refractory Mutation System (ARMS), and High Resolution Melting analysis (HRM PCR).

The genotyping can be performed by amplifying the microsatellites and Isolating the amplification products by capillary electrophoresis. Amplification of the microsatellites can be performed using conventional polymerase chain reaction (PCR) techniques and more preferably, amplification of microsatellites is performed by multiplex PCR. Suitable methods may also include Amplification Refractory Mutation System (ARMS), and High Resolution Melting analysis (HRM PCR).

In a preferred embodiment, amplification of said microsatellite repeat of 17 thymidine nucleotides localized in the splicing acceptor site of intron 8 of the gene encoding HSP110 can be performed as described hereabove.

In a preferred embodiment, amplification of said at least one microsatellite selected in the group consisting of the microsatellite repeats BAT26, NR21, NR27, NR24 and BAT25, comprises an initial denaturation step followed by cycles of denaturation-annealing-elongation steps and a final extension step.

The initial denaturation step may be performed under heating conditions ranging from 90° C. to 105° C., during 15 sec to 15 min. Preferably, the heating conditions range from 92° C. to 102° C., more preferably from 95° C. to 100° C., still more preferably the heating conditions are at 95° C. Preferably, the initial denaturation step is performed during 1 min to 15 min, more preferably during 2 min to 12 min, still more preferably during 5 min to 10 min, and still more preferably the initial denaturation step is performed during 5 min.

In a preferred embodiment, the initial denaturation step is performed at 95° C. during 5 min.

Each cycle of denaturation-annealing-elongation step includes a denaturation phase under heating conditions, followed by an annealing phase performed under conditions which allow the hybridization of the primers to the sequence to be amplified, and an elongation phase performed under conditions which allow the polymerase to synthesizes an extension product from each primer that is annealed to the sequence to be amplified.

The denaturation phase may be performed between 90° C. to 105° C., preferably 92° C. to 100° C., more preferably between 94° C. to 98° C., during 10 sec to 4 min, preferably during 10 sec to 2 min, more preferably during 15 sec to 1 min.

The annealing phase may be performed between 35° C. and 70° C., preferably between 40° C. to 65° C., more preferably between 45° C. to 60° C., still more preferably between 50° C. to 60° C., during 10 sec to 2 min, preferably during 20 sec to 1.5 min, more preferably during 25 sec to 45 sec.

The elongation phase may be performed between 40° C. and 80° C., preferably between 50° C. to 75° C., more preferably between 60° C. to 72° C., during 10 sec to 5 min, preferably during 20 sec to 3 min, more preferably during 25 sec to 1 min, still more preferably during 30 sec to 45 sec.

In a preferred embodiment, the denaturation phase is performed at 95° C. during 30 sec, the annealing phase is performed at 55° C. during 30 sec, and the elongation phase is performed at 72° C. during 30 sec. The denaturation-annealing-elongation step may be repeated during 30 to 60 cycles, preferably during 32 to 40 cycles, more preferably during 35 to 40 cycles. Still more preferably, the denaturation-annealing-elongation step is repeated during 35 cycles.

The final extension step may be performed between 40° C. and 80° C., preferably between 50° C. to 75° C., more preferably between 60° C. to 72° C., during 1 min to 10 min, preferably during 3 min to 8 min, more preferably during 4 min to 6 min.

In a preferred embodiment, the final extension step is performed at 72° C. during 5 min.

Amplification of the microsatellite marker BAT26 may be performed using the forward primer having the sequence 5'-CTGCGGTAATCAAGTTTTTAG-3' (SEQ ID NO: 14) and the reverse primer having the sequence 5'-AACCATTCAACATTTTTAACCC-3' (SEQ ID NO: 15).

Amplification of the microsatellite marker NR21 may be performed using the forward primer having the sequence 5'-GAGTCGCTGGCACAGTTCTA-3' (SEQ ID NO: 16) and the reverse primer having the sequence 5'-CTGGTCACTCGCGITTACAA-3' (SEQ ID NO: 17).

Amplification of the microsatellite marker NR27 may be performed using the forward primer having the sequence 5'-AACCATGCTTGCAAACCACT-3' (SEQ ID NO: 18) and the reverse primer having the sequence 5'-CGATAATACTAGCAATGACC-3' (SEQ ID NO: 19).

Amplification of the microsatellite marker NR24 may be performed using the forward primer having the sequence 5'-GCTGAATTTTACCTCCTGAC-3' (SEQ ID NO: 20) and the reverse primer having the sequence 5'-ATTGTGCCATTGCATTCCAA-3' (SEQ ID NO: 21).

Amplification of the microsatellite marker BAT25 may be performed using the forward primer having the sequence 5'-TACCAGGTGGCAAAGGGCA-3' (SEQ ID NO: 22) and the reverse primer having the sequence 5'-TCTGCATTTTAACTATGGCTC-3' (SEQ ID NO: 23).

By "instability on a microsatellite repeat of 17 thymidine nucleotides localized in the splicing acceptor site of intron 8 of the gene encoding HSP110" is meant a deletion or an addition of the repeated patter of thymidine nucleotides. As described herein, instability may be deemed to be present when a deletion of at least 3 thymidine nucleotides is detected in said biological sample. As described herein, instability may be deemed to be present when a deletion of 3 to 8 thymidine nucleotides or more is detected in said biological sample.

By "instability on at least one microsatellite marker selected from the group consisting of the microsatellite repeats BAT26, NR21, NR27, NR24 and BAT25" is meant a deletion or an addition of the repeated patter of mononucleotides, dinucleotides or trinucleotides.

In an exemplary embodiment, instability on the BAT26 microsatellite is deemed to be present when the BAT26 microsatellite consists of a repeated pattern of more than 26A or less than 20A.

In an exemplary embodiment, instability on the NR21 microsatellite is deemed to be present when the NR21 microsatellite consists of a repeated pattern of more than 21T or less than 16T.

In an exemplary embodiment, instability on the NR27 microsatellite is deemed to be present when the NR27 microsatellite consists of a repeated pattern of more than 26A or less than 23A.

In an exemplary embodiment, instability on the NR24 microsatellite marker is deemed to be present when the NR24 microsatellite consists of a repeated pattern of more than 23T or less than 18T.

In an exemplary embodiment, instability on the BAT25 microsatellite marker is deemed to be present when the BAT25 microsatellite consists of a repeated pattern of more than 25T or less than 19T.

Preferably, instability is deemed to be present when a deletion or an addition is detected on one allelle, and more preferably on two alleles.

In a particular embodiment, the method further comprises in step a) and b) comparison with a control sample. When a negative control sample is used, the negative control sample may e.g. correspond to a tissue sample from a healthy or MSS individual (preferably from the same tissue as the cancer cells), to a sample of healthy tissue from the patient (e.g. healthy tissue surrounding the cancerous tissue). In a specific embodiment, the negative control sample is the same type of sample than the biological sample of the patient. For example, if the biological sample of the patient is blood, the negative control sample is blood. In another example, if the biological sample of the patient is a biopsy of a colorectal cancer, the negative control sample is a biopsy of a colorectal cancer with microsatellite stability (MSS) phenotype.

The present invention is also directed to an in vitro method for diagnosing the microsatellite instability (MSI) phenotype of a tumor, said method comprising the step of detecting the presence or absence of a mutated heat-shock protein 110 (HSP110) as described hereabove in a biological sample of said patient, wherein the detection of the presence of said mutated HSP110 in the biological sample of the patient indicates that the patient suffers from a cancer with MSI phenotype.

In some embodiments, said method comprises the steps of:
   a) measuring the expression of a mutated HSP110 protein according to the invention in a biological sample of said patient; and/or
   b) measuring the expression of a mutated HSP110 mRNA according to the invention in a biological sample of said patient, wherein the detection of the presence of said mutated HSP110 protein and/or mRNA in the biological sample of the patient indicates that the patient suffers from a cancer with MSI phenotype.

In a specific embodiment, the method according to the invention comprises the steps of:
   a) measuring the expression of a mutated HSP110 as described hereabove in a biological sample of said patient;
   b) measuring the expression of a mutated HSP110 as described hereabove in a negative control sample;
wherein a significantly higher expression of mutated HSP110 measured at step a) in comparison to the expression measured at step b) is indicative of a good prognosis of survival and/or of response to the treatment.

At steps a) and b), measuring the expression of a mutated HSP110 may be performed by measuring the mutated HSP110 protein and/or the mutated HSP110 mRNA as described hereabove.

The higher expression is considered to be statistically significant if the expression level of mutated HSP110 in the biological sample of the patient is increased 2, 3, 4, 5, 6, 7, 8, 9 or 10 fold, or by at least 30%, 40%, 50%, 60%, 70% or 75% compared with the level of mutated HSP110 in the negative control sample. In a preferred embodiment, the higher expression is considered to be statistically significant if the expression level of mutated HSP110 in the biological sample of the patient is increased of at least 75%.

In another specific embodiment, the method according to the invention comprises the steps of:
   a) measuring the expression of a mutated HSP110 as described hereabove in a biological sample of said patient;
   b) measuring the expression of a wild-type HSP110 in said biological sample;
   c) comparing the expression measured at step (a) and (b), thereby deducing the diagnosis of the MSI phenotype.

At step a), measuring the expression of a mutated HSP110 may be performed by measuring the mutated HSP110 protein and/or the mutated HSP110 mRNA as described hereabove.

At step b), measuring the expression of wild-type HSP110 may be performed by measuring the wild-type HSP110 protein and/or the wild-type HSP110 mRNA as described hereabove.

Indeed, an expression level of mutated HSP110 superior or equal to 50%, 60%, 70%, 75%, 80%, 90% or 100% of the expression level of wild-type HSP110 indicates that the patient suffers from a cancer with MSI phenotype.

Comparing the expression measured at steps a) and b) may be performed by calculating an expression ratio, for example with the formula: Ratio=expression level of mutated HSP110/expression level of wild-type HSP110. An expression ratio superior or equal to 0.75 may for example indicate that the patient suffers from a cancer with MSI phenotype.

In still another specific embodiment, the method according to the invention comprises the steps of:
   a) measuring the expression of mutated HSP110 and wild-type HSP110 as described hereabove in a biological sample of said patient;
   b) analyzing expression obtained at step a) to generate an expression ratio;
   c) measuring the expression of mutated HSP110 and wild-type HSP110 as described hereabove in a negative control sample;
   d) analyzing expression obtained at step c) to generate an expression ratio;

wherein a significantly higher expression ratio generated at step b) in comparison to the expression ratio generated at step d) indicates that the patient suffers from a cancer with MSI phenotype.

At steps a) and c), measuring the expression of a mutated HSP110 may be performed by measuring the mutated HSP110 protein and/or the mutated HSP110 mRNA as described hereabove, and measuring the expression of wild-type HSP110 may be performed by measuring the wild-type HSP110 protein and/or the wild-type HSP110 mRNA as described hereabove.

The higher expression ratio is considered to be statistically significant if the ratio generated at step (b) is increased at least 2, 3, 4, 5, 6, 7, 8, 9 or 10 fold compared with the ratio generated at step (d). In a preferred embodiment, the ratio is considered to be statistically significant if the expression ratio in the biological sample of the patient is increased at least 7.5 fold.

Methods for measuring the expression level of mutated HSP110 and wild-type HSP110 are well-known in the art. The expression level may be measured either by quantifying mRNAs, or by quantifying proteins. Suitable methods include, e.g., immunochemistry, Elisa, Western blotting, flow cytometry, Northern blotting, PCR (e.g. RT-PCR and QRT-PCR), ligase chain reaction (LCR), transcription-mediated amplification (TMA), strand displacement amplification (SDA) and nucleic acid sequence based amplification (NASBA). Suitable methods may also include Amplification Refractory Mutation System (ARMS), and High Resolution Melting analysis (HRM PCR).

In some embodiments, measuring the expression level of mutated HSP110 and wild-type HSP110 is performed using the method described hereabove in the chapter "Prognosis methods and uses according to the invention".

As used herein, the biological sample may consist of a blood sample, a serum sample, a plasma sample, a feces sample or a biopsy of a cancer. Preferably the biological sample may consist of a biopsy of an adenoma or a primary cancer. Still more preferably the biological sample may consist of a biopsy of an adenoma or a primary cancer selected from the group consisting of colorectal cancer, stomach cancer, endometrial cancer, bladder cancer, urinary tract cancer, ovary cancer, prostate cancer, lymphomas, leukemias, glioblastoma, astrocytoma and neuroblastoma. Preferably, the biological sample is a biopsy of a colorectal cancer.

When a negative control sample is used, the negative control sample may e.g. correspond to a tissue sample from a healthy or MSS individual (preferably from the same tissue as the cancer cells), to a sample of healthy tissue from the patient (e.g. healthy tissue surrounding the cancerous tissue), or to a sample comprising an amount of mutated and/or wild-type HSP110 that is indicative of the expression level of mutated and/or wild-type HSP110 in a healthy or MSS individual. In a specific embodiment, the negative control sample is the same type of sample than the biological sample of the patient. For example, if the biological sample of the patient is blood, the negative control sample is blood. In another example, if the biological sample of the patient is a biopsy of a colorectal cancer, the negative control sample is a biopsy of a colorectal cancer with microsatellite stability (MSS) phenotype.

Methods for Determining a Suitable Therapeutic Regimen

The above methods can be used to determine and/or select the therapeutic regimen suitable for treating a subject suffering from a cancer liable to have a MSI phenotype.

Thus, the invention also relates to a method for determining a therapeutic regimen suitable for treating a subject suffering from a cancer liable to have a MSI phenotype, wherein said method comprises the steps of:
 a) determining the length of thymidine repetition of a microsatellite repeat of 17 thymidine nucleotides localized in the splicing acceptor site of intron 8 of the gene encoding heat-shock protein 110 (HSP110) in a biological sample of said patient, and
 b) deducing and/or selecting a suitable therapeutic regimen for the subject based on the length of said thymidine repetition.

The invention also pertains to the use of the microsatellite repeat of 17 thymidines localized in the splicing acceptor site of intron 8 of the gene encoding HSP110, as a biomarker for determining a suitable therapeutic regimen.

In some embodiments, said cancer liable to have a MSI phenotype may be a colorectal cancer, preferably a stage II or stage III colorectal cancer.

A "suitable therapeutic regimen" may refer to surgery, chemotherapy and/or radiotherapy suitable for treating a subject suffering from a cancer liable to have a MSI phenotype.

Small thymidine deletions, i.e. 3 or 4 thymidines, or less, indicate that a suitable therapeutic regimen may be a chemotherapeutic treatment that combines at least 2, 3, 4, 5, 6, 7, 8, 9, 10 or at most 10, 9, 8, 7, 6, 5, 4, 3, 2 agents, such as e.g. a combination of oxaliplatin, 5-fluorouracil and folinic acid, i.e. the FOLFOX treatment, or a combination of 5-fluorouracil and folinic acid, i.e. the FUFOL or LV5FU2 treatment.

Large thymidine deletions, i.e. 5 to 8 thymidines, or more, indicate that a suitable therapeutic regimen may be a chemotherapeutic treatment with a gingle agent such as 5-fluorouracil.

Determining the length of said thymidine repetition by may be performed by methods known by the skilled in the art. For instance, it may be performed by genotyping. Genotyping the microsatellite repeat of 17 thymidine nucleotides may be performed by methods known by the skilled in the art. For instance, genotyping as described in paragraph "Mutation analysis" of Example 1 or as described in paragraph "Diagnostic method according to the invention" of the description. Genotyping the microsatellite repeat of 17 thymidine nucleotides may be performed by methods known by the skilled in the art. For instance, genotyping the microsatellite repeat of 17 thymidine nucleotides may be performed by amplifying the said microsatellite repeat and isolating the amplification products by capillary electrophoresis. Amplification of said microsatellite repeat can be performed using conventional polymerase chain reaction (PCR) techniques as described in paragraph "Mutation analysis" of Example 1. Suitable methods may also include Amplification Refractory Mutation System (ARMS), and High Resolution Melting analysis (HRM PCR).

Kits According to the Invention

The invention also provides a kit comprising or consisting of a forward primer, a reverse primer and a probe, which can be used to detect the presence of mutated HSP110 as defined hereabove. The kit may further comprise a forward primer, a reverse primer and a probe, which can be used to detect wild-type HSP110.

In particular, the invention provides a kit comprising forward and reverse primers which are able to hybridize to mutated HSP110 and wild-type HSP110, and two probes, being able either to hybridize specifically to mutated HSP110, or to wild-type HSP110 as described above.

The forward primer according to the invention may have a nucleotide sequence comprising, or consisting of, SEQ ID NO: 4 or a sequence differing from sequence SEQ ID NO: 4 by one or two nucleotide substitution(s).

The reverse primer according to the invention may have a nucleotide sequence comprising, or consisting of, SEQ ID NO: 5 or a sequence differing from SEQ ID NO: 5 by one or two nucleotide substitution(s).

The probe specifically hybridizing to mutated HSP110 may have a nucleotide sequence comprising, or consisting of, sequence SEQ ID NO: 6 or a sequence differing from sequence SEQ ID NO: 6 by one or two nucleotide substitution(s).

The probe specifically hybridizing to wild-type HSP110 may have a nucleotide sequence comprising, or consisting of, sequence SEQ ID NO: 7 or a sequence differing from sequence SEQ ID NO: 7 by one or two nucleotide substitution(s).

Preferably, the probe is labelled. For instance, the probe can be labelled in a covalent or non-covalent manner with a wide variety of labels known in the art, including hapten labels (e.g. biotin), mass tag labels (e.g. stable isotope labels), radioactive labels, metal chelate labels, luminescent label (e.g. fluorescent, phosphorescent and chemiluminescent labels), etc.

Preferably, the probe is labelled with at least one fluorescent label or dye. The fluorescent dye can be a wide variety of dyes known in the art, including 6-FAM™, VIC®, TET™, NED™, Cy3®, Cy5®, HEX, TAMRA, DABCYL, BHQ™, DDQ, etc.

More preferably, the probe is labelled with a reporter dye and a quencher dye. Still more preferably, the probe is labelled at its 5' end with the reporter dye and at its 3' end with the quencher dye. The reporter dye may be a fluorescent dye, which can be for Instance 6-FAM™, VIC®, TET™, NED™, Cy3®, Cy5®, HEX, etc. The quencher dye may be a non-fluorescent dye (e.g. MGB™) or a fluorescent dye, which can be for instance TAMRA, DABCYL, BHQ™, DDQ, etc.

In a more preferred embodiment, the probe specifically hybridizing to mutated HSP110 is labelled with the reporter dye VIC™ at its 5' end and with the quencher dye TAMRA at its 3' end and the probe specifically hybridizing to wild-type HSP110 is labelled with the reporter dye 6-FAM™ at its 5' end and with the quencher dye TAMRA at its 3' end.

The forward and reverse primers and probe according to the invention are preferably 17 to 30 nucleotides long, more preferably 17 to 25 nucleotides long. In particular, said forward and reverse primers and probe may, independently from each other, be 17, 18, 19, 20, 21, 22, 23, 24 or 25 nucleotide long.

Said forward and reverse primer hybridizes respectively to the sequence SEQ ID NO: 3 and SEQ ID NO: 8 or to the sequence reverse to sequence SEQ ID NO: 3 and SEQ ID NO: 8 under high stringency and specific hybridization conditions. Furthermore, said probe hybridizing to mutated HSP110 according to the invention hybridizes to the sequence SEQ ID NO: 3 and said probe hybridizing to wild-type HSP110 according to the invention hybridizes to the sequence SEQ ID NO: 8.

The conditions of temperature and ionic strength determine the "stringency" of the hybridization.

The invention further provide a kit comprising or consisting a forward primer and a reverse primer which can be used to detect the length of the thymidine deletion in the microsatellite repeat as described hereabove.

The forward primer according to the invention may have a nucleotide sequence comprising, or consisting of, SEQ ID NO: 10 or a sequence differing from sequence SEQ ID NO: 10 by one or two nucleotide substitution(s).

The reverse primer according to the invention may have a nucleotide sequence comprising, or consisting of, SEQ ID NO: 11 or a sequence differing from SEQ ID NO: 11 by one or two nucleotide substitution(s).

The forward and reverse primers and probe according to the invention are preferably 17 to 30 nucleotides long, more preferably 17 to 25 nucleotides long. In particular, said forward and reverse primers and probe may, independently from each other, be 17, 18, 19, 20, 21, 22, 23, 24 or 25 nucleotide long.

Said forward and reverse primer hybridizes to the sequence SEQ ID NO: 9 or to the sequence reverse to sequence SEQ ID NO: 9 under high stringency and specific hybridization conditions.

The conditions of temperature and ionic strength determine the "stringency" of the hybridization. High stringency hybridization conditions correspond to a high Tm between 60° C. to 75° C. Hybridization requires that the two nucleic acids contain complementary sequences, although depending on the stringency of the hybridization, mismatches between bases are possible.

The invention also provides a kit comprising or consisting of an antibody, which can be used to detect the presence of mutated HSP110 as defined hereabove, i.e. an antibody that specifically recognizes a mutated HSP110 protein according to the invention. The kit may further comprise an antibody which can be used to detect wild-type HSP110.

In some embodiments, the invention provides a kit comprising an antibody that specifically recognizes a mutated HSP110 protein and an antibody that specifically recognizes a wild-type HSP110 as described above.

In some embodiments, said antibody that specifically recognizes a mutated HSP110 protein and said antibody that specifically recognizes a wild-type HSP110 are identical. For example, said antibody may be the Ab24503 antibody from Abcam.

In some embodiments, said antibody that specifically recognizes a mutated HSP110 protein and said antibody that specifically recognizes a wild-type HSP110 are different. For example, said antibody that specifically recognizes a mutated HSP110 protein is able to recognize a mutated HSP110 protein of sequence SEQ ID NO: 1, and said antibody that specifically recognizes a wild-type HSP110 may be the SPA-1101 antibody from Stressgen.

The invention also provides a kit comprising or consisting of:
  a) means for detecting the presence of mutated HSP110 as defined hereabove, and/or
  b) means for detecting detect wild-type HSP110, and/or
  c) means for detecting the length of the thymidine deletion in the microsatellite repeat as described hereabove.

In some embodiments, said means for detecting the presence of mutated HSP110 may be a forward primer, a reverse primer and a probe as described hereabove, and/or an antibody that specifically recognizes a mutated HSP110 protein as defined hereabove. In some embodiments, said means for detecting the presence of wild-type HSP110 may be a forward primer, a reverse primer and a probe as described hereabove, and/or an antibody that specifically recognizes a wild-type HSP110 protein as defined hereabove.

In some embodiments, said means for detecting the length of the thymidine deletion in the microsatellite repeat may be a forward primer and a reverse primer as defined hereabove.

By "detecting the length of the thymidine deletion in the microsatellite repeat" may also be meant "detecting instability of said microsatellite repeat".

Compounds and Pharmaceutical Compositions

It is known that HSP110 is a protein which accumulates abnormally in cancer cells, thus enhancing their survival (Yamagishi et al., *The FEBS journal* 275 (18), 4558 (2008); Hosaka et al., *Cancer science* 97 (7), 623 (2006); Yamagishi et al., *Experimental cell research* 312 (17), 3215 (2006); Siatskas et al., *Faseb J* 19 (12), 1752 (2005)). Moreover, HSP110 is especially strongly expressed in colon cancer cells (Kai et al., *Oncology reports* 10 (6), 1777 (2003)) and gene expression profile analysis of MSS primary CRC has linked HSP110 expression with metastasis and poor prognosis (Slaby et al., *Oncology reports* 21 (5), 1235 (2009)).

Here, it has been found that a mutated HSP110 is capable of having a dominant negative effect on the wild-type HSP110 in tumor cells, thus blocking its anti-apoptotic effect and sensitizing the tumor cells to apoptosis.

Thus, the invention is also directed to a compound selected from the group consisting of:
  a) the mutated heat-shock protein 110 (HSP110) as described hereabove; and/or
  b) a fragment of at least six consecutive amino acids of the mutated heat-shock protein (HSP110) comprising or consisting of an amino acids sequence at least 80% identical to SEQ ID NO: 1, preferably at least 80%, 85%, 90%, 95%, 96%, 97%, 98%, 99% or 100% identical to SEQ ID NO: 1; and/or
  c) a peptido-mimetic of the mutated HSP110 of a) or of the fragment of b); and/or
  d) a nucleic acid encoding the mutated HSP110 of a) or the fragment of b); and/or
  e) a Nonsense Mediated mRNA decay (NMD) inhibitor;
for use in the treatment of a cancer.

In a preferred embodiment, the compound according to the invention consists of a combination of the mutated heat-shock protein 110 (HSP110) as described hereabove and a Nonsense Mediated mRNA decay (NMD) inhibitor.

Nonsense-Mediated mRNA Decay (NMD) is a mRNA quality control process that degrades mRNA containing premature termination codons (PTC) in order to avoid the production of truncated proteins with potential deleterious effects for cells.

The identified mutated HSP110 is generated by a mRNA lacking exon 9, thus leading to the presence of a PTC. The inventors found that the mutated HSP110 is partially degraded in the MSI tumor cells via the NMD process. Consequently, its is advisable to inhibit NMD in order to restore the expression of the endogenous mutated HSP110 in tumor expressing such a protein, and/or to avoid the degradation of a mutated HSP110 administered to a patient.

As used herein a NMD inhibitor may be an indole derivative compound, preferably an indole derivative compound that has been described in the International Patent Application WO 2008/101935. In particular, said NMD inhibitor may be an indole derivative compound having the formula II of claim 16 of the patent application WO 2008/101935. Preferably, said NMD inhibitor may be an indole derivative selected in the group consisting of 6-Chloro-5,10-dimethyl-11H-pyrido[3',2':4,5]pyrrolo[3,2-g]isoquinolin, 5,10-dimethyl-11H-pyrido[3',2':4,5]pyrrolo[3,2-g]isoquinolin, 5,8-dimethyl-6-(pyridin-2-ylamino)-2H-isoquinolin-1-one, 6-(3-methoxy-pyridin-2-ylamino)-isoquinolin-1-one, 5,8-dimethyl-6-(5-methyl-pyridin-2-ylamino)-isoquinolin as defined in claim 21 of the patent application WO 2008/101935. More preferably, said NMD inhibitor may be 6-Chloro-5,10-dimethyl-11H-pyrido[3',2':4,5]pyrrolo[3,2-g]isoquinolin. This compound is also referred to as NMDI1 in the scientific litterature (Durant et al., *The Journal of Cell Biology* 178: 1145-1160 (2007)).

Methods for obtaining said compound are known by the skilled in the art. For example, methods for obtaining said compound are described in the patent application WO 2008/101935.

Most preferably, said cancer is a cancer liable to have a MSI phenotype. Said cancer may be, without limitation, a cancer selected in the group consisting of colorectal cancer, stomach cancer, endometrial cancer, bladder cancer, urinary tract cancer, ovary cancer, prostate cancer, lymphomas, leukemias, glioblastoma, astrocytoma and neuroblastoma. Preferably, said cancer is a colorectal cancer. Preferably, said cancer may be a primary tumor or an adenoma.

Still most preferably, said cancer is a cancer with MSS phenotype. Indeed, these cancers express low levels of mutated HSP110. Administering the mutated HSP110 and/or another inhibitor of wild-type HSP110 (i.e a peptido-mimetic or a fragment as decribed hereabove) is believed to restore their sensitivity to apoptosis.

Alternatively the cancer may have a MSI phenotype.

The inventors have found that cells expressing the mutated HSP110 are more sensitive to apoptosis, notably apoptosis induced by chemotherapeutic drugs. Therefore, the invention also pertains to a combination of a compound as described hereabove and of a chemotherapeutic drug, for simultaneous or sequential use in the treatment of cancer.

By a "chemotherapeutic drug" is meant a drug that has a marketing approval for the treatment of cancer, or a drug undergoing clinical or preclinical trial for the treatment of cancer.

The compound described herein may be formulated into a pharmaceutical composition. Thus the invention contemplates a pharmaceutical composition comprising any one of the above compound and a physiologically acceptable carrier. Physiologically acceptable carriers can be prepared by any method known by those skilled in the art.

Pharmaceutical compositions comprising at least one compound of the invention include all compositions wherein the compound(s) are contained in an amount effective to achieve the intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Remington's Pharmaceutical Sciences (Mack Publishing Company, Easton, USA, 1985), which is a standard reference text in this field. Pharmaceutically acceptable vehicles can be routinely selected in accordance with the mode of administration, solubility and stability of the peptides. For example, formulations for intravenous administration may include sterile aqueous solutions which may also contain buffers, diluents and other suitable additives. The use of biomaterials and other polymers for drug delivery, as well the different techniques and models to validate a specific mode of administration, are disclosed in literature.

The compound of the present invention may be administered by any means that achieve the intended purpose. For example, administration may be achieved by a number of different routes including, but not limited to subcutaneous, intravenous, intradermal, intramuscular, intraperitoneal, intracerebral, intrathecal, intranasal, oral, rectal, transdermal, buccal, topical, local, inhalant or subcutaneous use.

Dosages to be administered depend on individual needs, on the desired effect and the chosen route of administration. It is understood that the dosage administered will be dependent upon the age, sex, health, and weight of the recipient, concurrent treatment, if any, frequency of treatment, and the nature of the effect desired. The total dose required for each treatment may be administered by multiple doses or in a single dose.

Depending on the intended route of delivery, the compounds may be formulated as liquid (e.g., solutions, suspensions), solid (e.g., pills, tablets, suppositories) or semisolid (e.g., creams, gels) forms.

In a preferred embodiment, the compositions are presented in unit dosage forms to facilitate accurate dosing. The term "unit dosage forms" refers to physically discrete units suitable as unitary dosages for human subjects and other mammals, each unit containing a pre-determined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

The compounds of this invention can also be administered in sustained release forms or from sustained release drug delivery systems.

The invention also contemplates a pharmaceutical composition comprising a nucleic acid encoding the mutated HSP110 of the invention in the frame of e.g. a treatment by gene therapy. In this case, the nucleic acid is preferably present on a vector, on which the sequence coding for the peptide is placed under the control of expression signals (e.g. a promoter, a terminator and/or an enhancer) allowing its expression. The vector may for example correspond to a viral vector such as an adenoviral or a lentiviral vector.

The invention further provides kits comprising a pharmaceutical composition comprising a compound of the invention and instructions regarding the mode of administration. These instructions may e.g. indicate the medical indication, and/or the route of administration, and/or the dosage, and/or the group of patients to be treated.

The invention further provides a method for treating cancer, wherein said method comprises the administration of an effective amount of a compound selected from the group consisting of:
  a) the mutated heat-shock protein 110 (HSP110) as described hereabove; and/or
  b) a fragment comprising or consisting of at least six consecutive amino acids at least 80% identical to SEQ ID NO: 1, preferably at least 80%, 85%, 90%, 95%, 96%, 97%, 98%, 99% or 100% identical to SEQ ID NO: 1; and/or
  c) a peptido-mimetic of the mutated HSP110 of a) or of the fragment of b); and/or
  d) a nucleic acid encoding the mutated HSP110 of a) or a fragment of b); and/or
  e) a Nonsense Mediated mRNA decay (NMD) inhibitor, to an individual in need thereof.

In a preferred embodiment, said method comprises the administration of the mutated heat-shock protein 110 (HSP110) as described hereabove and a Nonsense Mediated mRNA decay (NMD) inhibitor.

The compound is administered in an "effective amount", i.e. in an amount sufficient to treat the cancer. It will be appreciated that this amount will vary with the effectiveness of therapeutic agent(s) employed, with the nature of any carrier used, with the seriousness of the disease and the age of the patient. The determination of appropriate amounts for any given composition is within the skill in the art, through standard series of tests designed to assess appropriate therapeutic levels.

By "individual in need thereof" is meant an individual suffering from a cancer, or an individual that is in remission after having suffered from cancer.

In the frame of the present invention, the individual preferably is a human individual. However, the veterinary use of the polypeptides and drugs according to the present invention is also envisioned. The individual may thus also correspond to a non-human individual, preferably a non-human mammal.

The term "treating" is meant to encompass both therapeutic and prophylactic methods, i.e. a method aiming at curing, improving the condition and/or extending the lifespan of an individual suffering from the cancer. It also refers to methods aiming at preventing the appearance or the spreading of metastases, as well as methods aiming at preventing a relapse.

All references cited herein, including journal articles or abstracts, published or unpublished patent application, issued patents or any other references, are entirely incorporated by reference herein, including all data, tables, figures and text presented in the cited references.

Although having distinct meanings, the terms "comprising", "having", "containing' and "consisting of" have been used interchangeably throughout this specification and may be replaced with one another.

The invention will be further evaluated in view of the following examples and figures.

DESCRIPTION OF THE SEQUENCES

Figure 1:
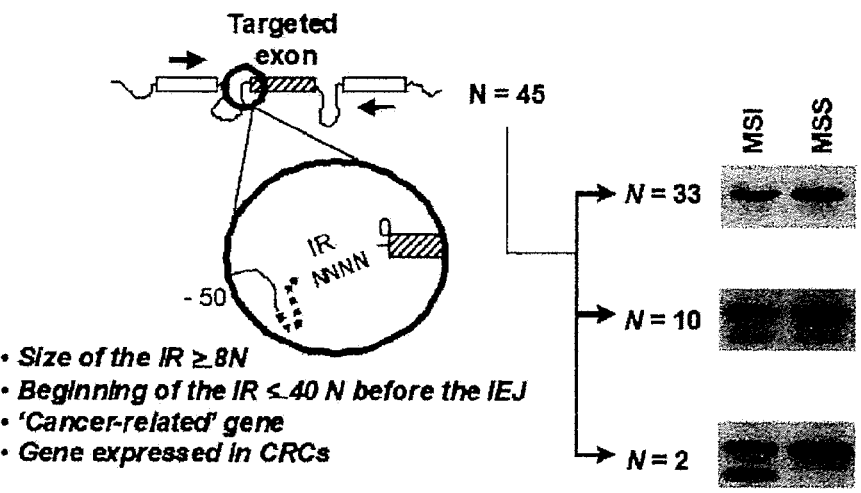
FIG. 1 depicts the screening of a large series of candidate genes containing intronic DNA repeats whose instability due to MSI might generate exon skipping or exon retention. The criteria used to select the candidate genes are shown (IR: Intronic Repeat. IEJ: Intron-Exon Junction). All selected genes were expressed in CRCs. Among 45 candidate genes, two displayed aberrant RT-PCR profiles that were suggestive of exon skipping in CRC cell lines displaying MSI, i.e. MRE11 and HSP110.

SEQ ID NO: 1 refers to the amino acid sequence of the mutated HSP110 protein.

SEQ ID NO: 2 refers to the amino acid sequence of the wild-type HSP110 protein.

SEQ ID NO: 3 refers to the nucleotidic sequence of the mutated HSP110.

SEQ ID NO: 4, 5, 6, 7, 10, 11, 12 to 23 refer to primers and probes sequences.

SEQ ID NO: 8 refers to the nucleotidic sequence of the wild-type HSP110.

SEQ ID NO: 9 refers to the microsatellite repeat of 17 thymidine nucleotides localized in the splicing acceptor site of intron 8 of the gene encoding HSP110.

EXAMPLES

Example 1

Material and Methods

Tumor Samples and Cell Lines

CRC cell lines were purchased from the American Type Culture Collection and maintained in DMEM (LifeTechnologies) containing 10% fetal calf serum (Invitrogen) and Glutamine. Primary tumours and normal colonic tissues were obtained from patients undergoing surgery for CRC. All cases were histopathologically confirmed as being adenocarcinomas. The MSI status was determined by fluorescent multiplex PCR comprising 5 quasimonomorphic mononucleotide repeats (BAT-25, BAT-26, NR-21, NR-24 and NR-27), as described in Buhard et al., *J Clin Oncol* 24 (2), 241 (2006).

Mutation Analysis

Tumour DNA from frozen samples was extracted using QIAamp DNA Tissue Kit (Qiagen) according to manufacturer's instructions. Specific primers for HSP110 intron 8 were designed. The forward primer and the reverse primer for mutation analysis have respectively the sequences 5'-CCCTGTCCATCCATTGGAATTGA-3' (SEQ ID NO: 10) and 5'-GGAACTGCATCTGTGACGGAA-3' (SEQ ID NO: 11). PCR reactions were performed in a final volume of 20 µl containing 100 ng of genomic DNA, 0.15-0.40 µM of each primer and 1 unit of HotStarTaq DNA polymerase (Qiagen). The thermal cycling conditions comprised an initial denaturation step at 94° C. for 10 min and 40 cycles at 94° C. for 30 s and 57° C. for 30 s. Adequate dilutions of the fluorescent PCR products were mixed with formamide and GeneScan™400HD ROX™ Size Standard (Applied Biosystems), heat-denatured and run on a short capillary containing GS Performance Optimized Polymer 4 on the ABI 3130 Genetic Analyzer using GeneMapper 3.7 software (Applied Biosystems).

Real-Time Quantitative RT-PCR (ORT-PCR) Analysis

Total RNA was isolated using Trizol reagent according to the manufacturer's instructions (Invitrogen). RNA integrity was evaluated on a 2100 Bioanalyzer using the RNA 6000 Nano LabChip kit (Agilent). Only samples with intact RNAs were used for gene expression analysis (28S/18S RNA ratio>1.6 and absence of aberrant peaks on the RNA profile). cDNAs were synthesized using the High Capacity cDNA Archive Kit according to the manufacturer's instructions (Applied Biosystems). For QRT-PCR experiments, expression values were obtained from the Ct number at which the increase in signal associated with exponential amplification of PCR products starts to be detected using the Applied SDS Biosystems analysis software according to the manufacturer. Primers (Forward 5'-GCTACACGAATTCCAGCTGTGA-3' (SEQ ID NO: 4) and Reverse 5'-GAGCAGCATG-GTTTCGACTAAA-3' (SEQ ID NO: 5)) and internal probes were designed using Primer Express and synthesized by Applied Biosystems. Internal probes were specifically designed to amplify either the wild-type HSP110 (herein after called HSP110wt) (5'-6FAM-TACAGTGTG-CAATACTT-3' (SEQ ID NO: 7)) or mutated HSP110 (herein after called HSP110delE9) (5'-VIC-ATGTGCATTA-CAGTGTTC-3' (SEQ ID NO: 6)) transcripts. Assays for no-template control and no-reverse transcriptase control (reverse transcriptase-negative) produced negligible signals (usually Ct>35) and were used to confirm the absence of primer-dimer formation and genomic DNA contamination. PCR reactions were performed in triplicate using an ABI Prism 7900 Sequence Detection System and the TaqMan PCR master mix (Applied Biosystems). Results were expressed as N-fold difference in HSP110ΔE9 relative to HSP110wt expression (ΔCt), where ΔCt was determined in each case by subtracting the average Ct value of the HSP110delE9 mRNA from the average Ct value of the HSP110wt mRNA. The thermal cycling conditions comprised an initial denaturation step at 95° C. for 10 min and 40 cycles at 95° C. for 15 s and 60° C. for 1 min.

Cells, Plasmids, Transfections and Materials

HCT116 cells, mouse embryonic fibroblasts (MEFs), American Type Culture Collection, ATCC) and HSF1$^{+/+}$ MEF were cultivated in DMEM/10% FBS (fetal bovine serum, Lonza, Basel, Switzerland). HSP70 and HSP27 constructs were previously described (Ribeil et al., *Nature* 445: 102-105 (2007); Brunet et al., *BMC Med Gene* 10: 144 (2009)). The GFP-HSP110 construct was obtained from Addgene (Cambridge, England). The HSP110 mutant was produced by PCR from GFP-HSP110 vector using the following primers: 5'CGC GCG CGC AAG ATC TAC ATG TCG GTG GTG GGG 3' (Bgl II) (SEQ ID NO:12) and 5'CGC GCG CGC AAG CTT TCA TGA ACA CTG TAA TGC ACA TCC3' (HindIII) (SEQ ID NO:13). After digestion by the enzymes Bgl II and Hind III, mutant HSP110 cDNA was cloned into the EGFp C2 vector. Transfections were performed using the Jet PEI reagent (Ozyme, Saint-Quentin-en-Yvelines, France). Oxaliplatin was purchased from Sigma-Aldrich (stock solution 5 mg/ml). Recombinant His-TRAIL was a gift from Olivier Micheau (INSERM U866, France).

Immunoprecipitation and Western-Blotting

Transfected cells were first lysed in lysis buffer (50 mM Hepes (pH 7.6), 150 mM NaCl, 5 mM EDTA and 0.1% NP40) followed by immunoprecipitation using GFP-tag antibody. Immunoprecipitates were separated in a 10% SDS-polyacrylamide gel and then transferred to PVDF membranes using a wet transfer apparatus (BioRad, Hercules, California, USA). Membranes were first probed overnight using primary antibodies: HA-tag antibody was from Covance (Eurogentec, Angers, France), 14-3-3 from Santa-Cruz (TebuBio, Le Perray en Yvelines, France) and GFP-tag antibody from Millipore (Molsheim, France). Next, membranes were incubated for 1 hour with appropriate secondary antibodies coupled to horseradish peroxidase (Jackson ImmunoResearch Laboratories, West Grove, PE) and revealed with ECL (Amersham, Les Ullis, France).

Cell Death Analysis

Adherent cells were plated onto 12-well culture plates ($1.5 \times 10^5$ cells/well) in complete medium. When indicated, cells were treated with TRAIL (150 ng/ml or 500 ng/ml) for 4 hours and cell death was measured by Hoechst 33342 staining (Sigma-Aldrich). Following treatment for 48 h with oxaliplatin (OxaPt, 20 and 40 µM), apoptotic cells were detected by Apo2.7 staining. Briefly, cells were harvested, washed in PBS and permeabilized with digitonin (100 mg/ml, 10 min at 4° C.). Cells were incubated with anti-Apo2.7 antibody and apoptotic cells were analyzed by flow cytometry using a LSR2 flow cytometer (Becton Dickinson, Franklin Lakes, N.J.).

HSP110 Chaperone Activity

HSP110 chaperone activity was evaluated using a protein thermolability assay. Total protein (2 mg/mL) from HSF1$^{-/-}$ MEFs that had been transfected with HSP70 (positive control), HSP27 (negative control), HSP110 or Mutant HSP110 (Dc Assay Kits, Bio-Rad, France) was heated at 55° C. for 1 hour. After centrifugation to eliminate aggregated proteins, the remaining native proteins in the supernatant were quantified. The ratio between the initial amount of soluble protein and that obtained after heating allowed for the quantification of protein aggregation.

Nucleus/Cytoplasm Extraction

Cytoplasmic and nuclear extracts were obtained after lysis of $5$-$10 \times 10^6$ cells for 10 minutes on ice in lysis buffer (20 mM Hepes pH 7.4, 10 mM KCl, 1 mM EDTA, 10% glycerol) with 0.2% NP-40 in the presence of protease inhibitors. Cell lysates were centrifuged at 14,000 rpm for 10 min and the supernatant was carefully collected (cytoplasmic fraction). The pellet was washed once and resuspended in lysis buffer (20 mM Hepes pH 7.4, 10 mM KCl, 1 mM EDTA, 20% glycerol, 350 mM NaCl, protease inhibitors) and nuclear fractions were obtained after centrifugation (14000 rpm, 10 min).

Immunofluorescence Staining

GFP-transfected cells were fixed in PBS-paraformaldehyde (4%) for 15 min and then washed with PBS (Cambrex, Emerain ville, France). GFP fluorescence was assessed using the Cell Observer station (Zeiss, Germany).

Patients

Patients from the retrospective study underwent curative surgical resection of histologically proven Dukes' 2 or Dukes' 3 CRC. The study has been conducted according to the recommendations of the institutional authorities. Patients were operated at the Saint-Antoine hospital or at the Centre de Physiopathologie de Toulouse Purpan. Dukes' 3 CRC patients received adjuvant chemotherapy with drugs including FL (fluorouracil plus leucovorin) and oxaliplatin (FOL-FOX4).

Statistical Analysis

Differences between variables were assessed with the Chi-2 or Fisher's exact test, as appropriate. Comparisons of the mean between the variables were assessed using the Student t test. The primary outcome was disease free survival. Survival curves were obtained using Kaplan-Meier estimates. Difference between survival curves were assessed using the log-rank test with a end point at 5 years.

Example 2

Results

Figure 2:
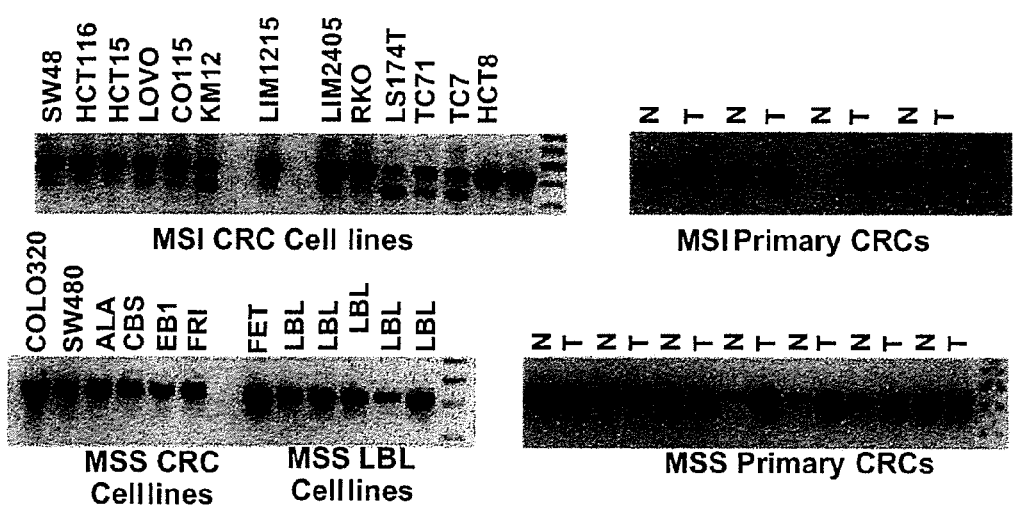
FIG. 2 depicts the analysis of the presence of a specific, additional HSP110 RT-PCR product detected in MSI tumour samples for 14 CRC cell lines. Its size was suggestive of exon 9 skipping in HSP110 mRNA. We failed to detect its expression in MMR-proficient cell lines, e.g. in 7 MSS CRC cell lines and 4 MSS LBL cell lines. The results were confirmed in a series of 4 and 7 primary CRCs (T) that were MSI or MSS, respectively, and their matching normal mucosa (N).

Investigation of Aberrant Splicing Events Due to MSI in CRC Cell Lines and Primary Tumours In order to find out new mutant with a putative role in MSI-driven carcinogenesis, we analyzed by non quantitative RT-PCR the expression pattern of 45 candidate exons that are located downstream of an intron containing a mononucleotide repeat sequence of at least 8 nucleotides and in the vicinity of the splice acceptor site. The detailed criteria used to select these candidate genes are shown in FIG. 1. The search was undertaken by non quantitative RT-PCR using a set of human MSI and MSS CRC cell lines (N=21; 14 MSI, 7 MSS). Using primers that matched upstream and downstream sequences of each targeted exon, 43 displayed the same expression pattern in MSI and MSS cancer cell lines. These were (N=10) or were not (N=33) alternatively spliced. In the remaining 2 cases (MRE11 and HSP110), the pattern of expression was markedly different between MSI and MSS samples. This was due to the presence of an additional PCR product that was only detectable in MSI CRC cell lines and was due to exon 5 skipping in MRE11 (result not shown), as already reported by Giannini et al., Oncogene 23 (15), 2640 (2004), and exon 9 skipping in HSP110 (FIG. 2 and not shown). The presence of this additional HSP110 RT-PCR product was also found to be specific to MSI primary tumour samples (FIG. 2). It was not detected in a series of non-tumour human cell lines as additional MMR-proficient controls (Lymphoblastoid cell lines [LBLs], N=20) (FIG. 2). Amongst patients with MSI CRCs, we observed that amplification of the additional RT-PCR product was restricted to MSI tumour tissues and was never observed in matching normal mucosal samples (FIG. 2).

HSP110 $T_7$ Intronic DNA Microsatellite is Always Mutated in MSI CRC Cell Lines and Primary Tumours Next, we determined the mutational status of the HSP110 $T_{17}$ DNA repeat located upstream and near the splice acceptor site in intron 8. Allelic profiles of this non-coding repeat were analyzed using fluorescence genotyping in our panel of MSI and MSS CRC cell lines and primary tumours, as well as in control LBLs to assess the polymorphic status of this sequence (Table 2).

TABLE 2

Allelic profile of T17 repeat and HSP110delE9 expression level in MSI and MSS cell lines and primary tomurs, and in control lymphoblasts (LBL).

| SAMPLE TYPE | SAMPLE NAME | MSI/MSS STATUS | T17 GENOTYPE | DELETION SIZE (in bp)* | HSP110delE9 mRNA EXPRESSION (in %) |
|---|---|---|---|---|---|
| CRC-CELL LINE | CO115 | MSI | 139/140 | 7 | 29.4 |
| CRC-CELL LINE | LS174T | MSI | 140/142 | 6 | 193.9 |
| CRC-CELL LINE | LOVO | MSI | 141/141 | 5 | 25.7 |
| CRC-CELL LINE | TC71 | MSI | 142/146 | 4 | 48.1 |
| CRC-CELL LINE | HCT15 | MSI | 142/143 | 4 | 17.1 |
| CRC-CELL LINE | HCT116 | MSI | 143/144 | 3 | 14.3 |
| CRC-CELL LINE | TC7 | MSI | 141/143 | 5 | 90.2 |
| CRC-CELL LINE | SW48 | MSI | 141/144 | 5 | 14.1 |
| CRC-CELL LINE | RKO | MSI | 139/142 | 6 | 14.4 |
| CRC-CELL LINE | HCT8 | MSI | 143/145 | 3 | 7.3 |
| CRC-CELL LINE | LS411 | MSI | 140/141 | 6 | 596.9 |
| CRC-CELL LINE | KM12 | MSI | 140/141 | 6 | 88.4 |
| CRC-CELL LINE | LIM1215 | MSI | 142/143 | 4 | 12.6 |
| CRC-CELL LINE | LIM2405 | MSI | 141/143 | 5 | 12.9 |
| CRC-CELL LINE | ALA | MSS | 146 | 0 | 8.2 |
| CRC-CELL LINE | COLO320 | MSS | 146 | 0 | 6.8 |
| CRC-CELL LINE | EB | MSS | 145 | 0 | 5.0 |
| CRC-CELL LINE | FET | MSS | 146 | 0 | 6.0 |
| CRC-CELL LINE | FRI | MSS | 145 | 0 | 4.6 |
| CRC-CELL LINE | GLY | MSS | 145/146 | 0 | 9.1 |
| CRC-CELL LINE | SW480 | MSS | 146 | 0 | 8.4 |
| LBL-CELL LINE | LBL-1 | MSS | 145 | 0 | 17.9 |
| LBL-CELL LINE | LBL-2 | MSS | 145/146 | 0 | 18.0 |
| LBL-CELL LINE | LBL-3 | MSS | 146 | 0 | 14.0 |
| LBL-CELL LINE | LBL-4 | MSS | 145 | 0 | 10.6 |
| LBL-CELL LINE | LBL-5 | MSS | 146 | 0 | 22.6 |
| LBL-CELL LINE | LBL-6 | MSS | 145/146 | 0 | 26.0 |
| LBL-CELL LINE | LBL-7 | MSS | 145/146 | 0 | 19.3 |
| LBL-CELL LINE | LBL-8 | MSS | 145 | 0 | 19.7 |
| LBL-CELL LINE | LBL-9 | MSS | 145/146 | 0 | 24.0 |
| LBL-CELL LINE | LBL-10 | MSS | 145 | 0 | 18.9 |
| LBL-CELL LINE | LBL-11 | MSS | 146 | 0 | 19.9 |
| LBL-CELL LINE | LBL-12 | MSS | 145/146 | 0 | 15.4 |
| LBL-CELL LINE | LBL-13 | MSS | 146 | 0 | 16.7 |
| LBL-CELL LINE | LBL-14 | MSS | 145 | 0 | 26.8 |
| LBL-CELL LINE | LBL-15 | MSS | 145/146 | 0 | 18.3 |
| LBL-CELL LINE | LBL-16 | MSS | 145/146 | 0 | 23.7 |
| LBL-CELL LINE | LBL-17 | MSS | 145/146 | 0 | 20.8 |
| LBL-CELL LINE | LBL-18 | MSS | 145/146 | 0 | 24.3 |
| LBL-CELL LINE | LBL-19 | MSS | 145 | 0 | 25.3 |
| LBL-CELL LINE | LBL-20 | MSS | 146 | 0 | 26.5 |
| PRIMARY CRC | TMSI1 | MSI | 141/145 | 5 | 46.8 |
| PRIMARY CRC | TMSI10 | MSI | 143/146 | 3 | 11.7 |
| PRIMARY CRC | TMSI11 | MSI | 141/144 | 5 | 18.6 |
| PRIMARY CRC | TMSI12 | MSI | 140/142/144 | 6 | 44.9 |
| PRIMARY CRC | TMSI13 | MSI | 140/144 | 6 | 38.9 |
| PRIMARY CRC | TMSI14 | MSI | 141/142/145/146 | 5 | 40.8 |
| PRIMARY CRC | TMSI15 | MSI | 141/144/145 | 5 | 24.1 |
| PRIMARY CRC | TMSI16 | MSI | 140/144 | 6 | 24.2 |
| PRIMARY CRC | TMSI17 | MSI | 140/143/145 | 6 | 26.8 |
| PRIMARY CRC | TMSI18 | MSI | 139/144 | 7 | 25.9 |
| PRIMARY CRC | TMSI19 | MSI | 138/146 | 8 | 143.3 |
| PRIMARY CRC | TMSI2 | MSI | 142/144 | 4 | 18.7 |
| PRIMARY CRC | TMSI20 | MSI | 141/144/146 | 5 | 31.2 |
| PRIMARY CRC | TMSI21 | MSI | 143/145/146 | 3 | 15.9 |
| PRIMARY CRC | TMSI22 | MSI | 140/142/144 | 6 | 39.9 |
| PRIMARY CRC | TMSI23 | MSI | 140/142/145 | 6 | 46.2 |
| PRIMARY CRC | TMSI24 | MSI | 141/143/145 | 5 | 49.8 |
| PRIMARY CRC | TMSI25 | MSI | 142/146 | 4 | 45.5 |
| PRIMARY CRC | TMSI26 | MSI | 140/145 | 6 | 106.3 |
| PRIMARY CRC | TMSI27 | MSI | 139/140/144/145 | 7 | 252.7 |
| PRIMARY CRC | TMSI28 | MSI | 139/143/146 | 7 | 26.7 |
| PRIMARY CRC | TMSI29 | MSI | 140/143/146 | 6 | 206.4 |
| PRIMARY CRC | TMSI3 | MSI | 141/142/145 | 5 | 28.5 |
| PRIMARY CRC | TMSI30 | MSI | 142/145 | 4 | 18.9 |
| PRIMARY CRC | TMSI31 | MSI | 142/143/145 | 4 | 22.4 |
| PRIMARY CRC | TMSI32 | MSI | 142/145 | 4 | 55.2 |
| PRIMARY CRC | TMSI33 | MSI | 140/141/145 | 6 | 288.2 |
| PRIMARY CRC | TMSI34 | MSI | 140/146 | 6 | 314.0 |
| PRIMARY CRC | TMSI35 | MSI | 143/145 | 3 | 20.8 |
| PRIMARY CRC | TMSI36 | MSI | 141/146 | 5 | 58.5 |
| PRIMARY CRC | TMSI37 | MSI | 138/142/145 | 8 | 29.7 |

TABLE 2-continued

Allelic profile of T17 repeat and HSP110delE9 expression level in MSI
and MSS cell lines and primary tomurs, and in control lymphoblasts (LBL).

| SAMPLE TYPE | SAMPLE NAME | MSI/MSS STATUS | T17 GENOTYPE | DELETION SIZE (in bp)* | HSP110delE9 mRNA EXPRESSION (in %) |
|---|---|---|---|---|---|
| PRIMARY CRC | TMSI38 | MSI | 141/145/146 | 5 | 479.2 |
| PRIMARY CRC | TMSI39 | MSI | 141/145 | 5 | 319.5 |
| PRIMARY CRC | TMSI4 | MSI | 141/142/145 | 5 | 76.8 |
| PRIMARY CRC | TMSI40 | MSI | 141/144 | 5 | 26.2 |
| PRIMARY CRC | TMSI41 | MSI | 140/145 | 6 | 27.2 |
| PRIMARY CRC | TMSI42 | MSI | 143/145 | 3 | 21.3 |
| PRIMARY CRC | TMSI43 | MSI | 141/144 | 5 | 57.5 |
| PRIMARY CRC | TMSI5 | MSI | 140/144 | 6 | 69.3 |
| PRIMARY CRC | TMSI6 | MSI | 141/145 | 5 | 73.3 |
| PRIMARY CRC | TMSI7 | MSI | 142/143/146 | 4 | 25.4 |
| PRIMARY CRC | TMSI8 | MSI | 142/146 | 4 | 19.1 |
| PRIMARY CRC | TMSI9 | MSI | 141/145/146 | 5 | 38.8 |
| PRIMARY CRC | TMSS1 | MSS | 145 | 0 | 12.7 |
| PRIMARY CRC | TMSS10 | MSS | 146 | 0 | 11.1 |
| PRIMARY CRC | TMSS11 | MSS | 146/145 | 0 | 6.3 |
| PRIMARY CRC | TMSS12 | MSS | 146 | 0 | 6.8 |
| PRIMARY CRC | TMSS13 | MSS | 145 | 0 | 6.9 |
| PRIMARY CRC | TMSS14 | MSS | 146/145 | 0 | 7.4 |
| PRIMARY CRC | TMSS15 | MSS | 146/145 | 0 | 6.6 |
| PRIMARY CRC | TMSS16 | MSS | 146/145 | 0 | 7.8 |
| PRIMARY CRC | TMSS17 | MSS | 145 | 0 | 7.6 |
| PRIMARY CRC | TMSS18 | MSS | 146/145 | 0 | 8.7 |
| PRIMARY CRC | TMSS19 | MSS | 146 | 0 | 6.0 |
| PRIMARY CRC | TMSS2 | MSS | 146/145 | 0 | 10.8 |
| PRIMARY CRC | TMSS20 | MSS | 146 | 0 | 8.4 |
| PRIMARY CRC | TMSS3 | MSS | 146 | 0 | 18.4 |
| PRIMARY CRC | TMSS4 | MSS | 146/145 | 0 | 16.3 |
| PRIMARY CRC | TMSS5 | MSS | 146/145 | 0 | 16.4 |
| PRIMARY CRC | TMSS6 | MSS | 146 | 0 | 18.7 |
| PRIMARY CRC | TMSS7 | MSS | 145 | 0 | 18.4 |
| PRIMARY CRC | TMSS8 | MSS | 146/145 | 0 | 16.0 |
| PRIMARY CRC | TMSS9 | MSS | 146 | 0 | 16.2 |

*calculated by substracting the size of the shortest HSP110 allele to 146 in each case,
** relative to HSP110 wt expression (Quantitative RT-PCR).

Figure 4:
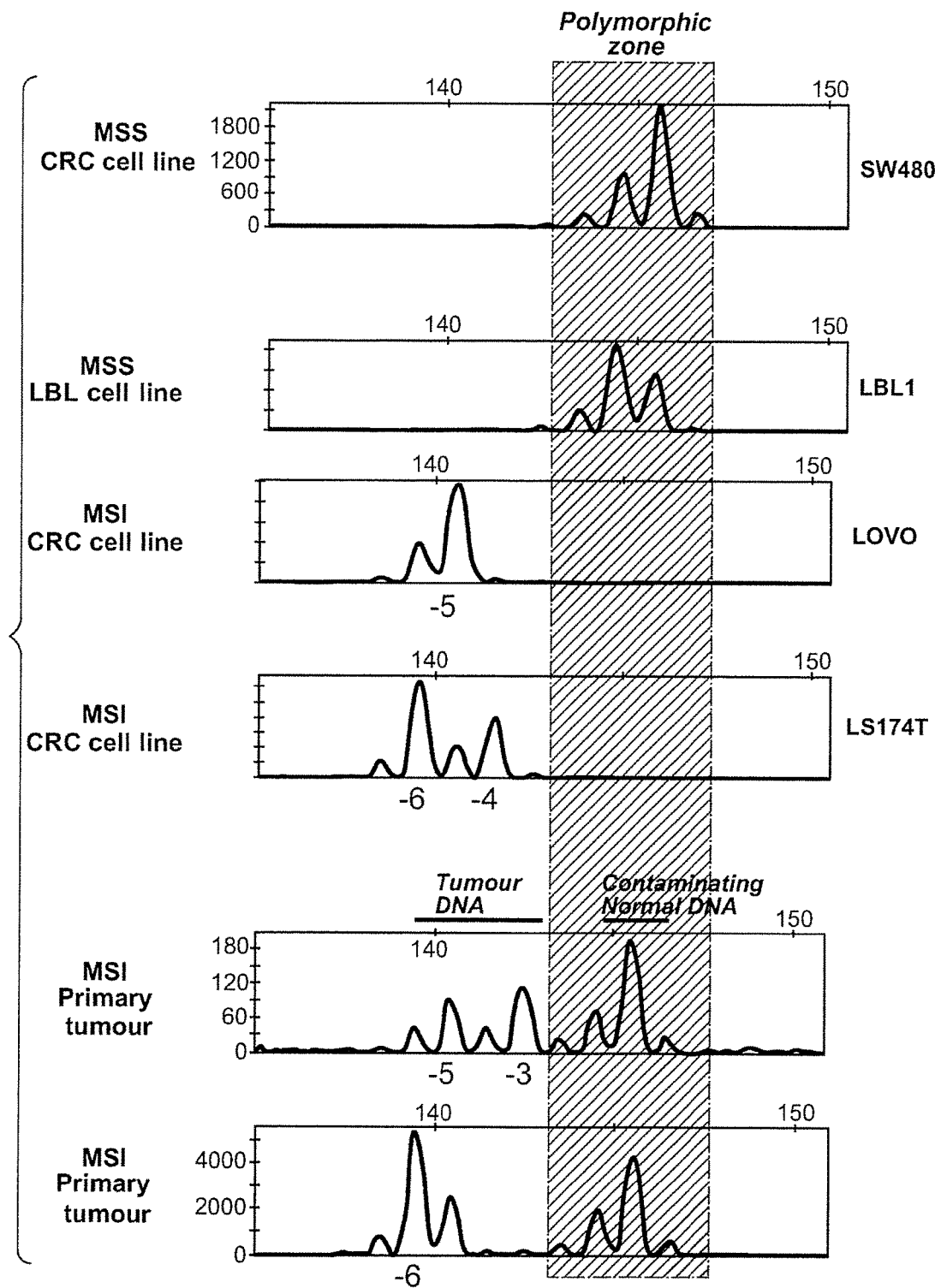
FIG. 4 depicts allelic profiles for several MSI CRC cell lines and primary tumours and controls (MSS CRC and LBL cell lines) at the intronic HSP110 $T_{17}$. MSS samples were weakly polymorphic, whereas MSI CRC cell lines and primary tumours always displayed aberrant alleles falling outside of the polymorphic zone (hatched zone). Various allelic deletions ranging from 3 to 8 base pairs in size were observed. The deletions observed were mostly bi-allelic in MSI CRC cell lines. In MSI primary tumours, the allelic profiles were in most cases highly suggestive of bi-allelic mutations, as shown. Numbers indicate the size of the HSP110 $T_{17}$ deletion in MSI tumour samples (in base pair).
Figure 5:
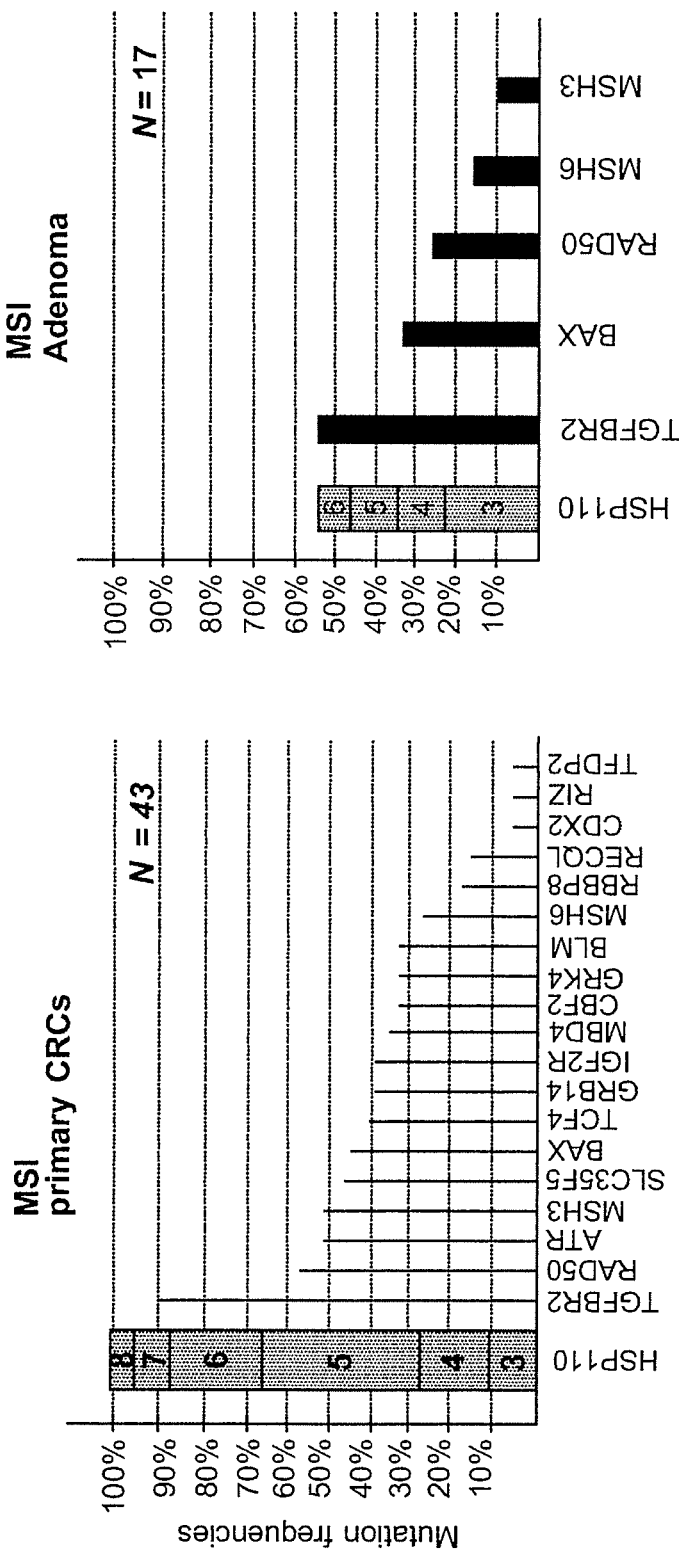
FIG. 5 depicts the mutation frequency analysis of the intronic HSP110 $T_{17}$. Mutation of the repeat was more frequently detected in MSI primary CRCs (100%) and pre-malignant adenoma (53%) than for any of the microsatellite coding alterations. Numbers indicate the size of the HSP110 $T_{17}$ deletion in MSI tumour or adenoma samples.

Overall, this sequence was weakly polymorphic in MMR-proficient samples (FIG. 4), whereas it was systematically mutated in 14/14 (100%) of the MSI CRC cell lines and in 43/43 (100%) of the MSI CRC primary tumours. The allelic deletions ranged from 3 to 8 base pairs beyond the polymorphic zone (FIG. 4 and Table 2). Mutation of HSP110 $T_{17}$ was more frequent than all coding microsatellites reported in MSI primary CRCs (FIG. 5). This mutation was also detected in 9/17 (53%) adenomas displaying MSI, although with smaller allelic deletions than observed with MSI primary CRCs. Mutation of HSP110 $T_{17}$ was as frequent as that affecting TGFBR2 in such pre-malignant colonic lesions (FIG. 5).

Figure 6:
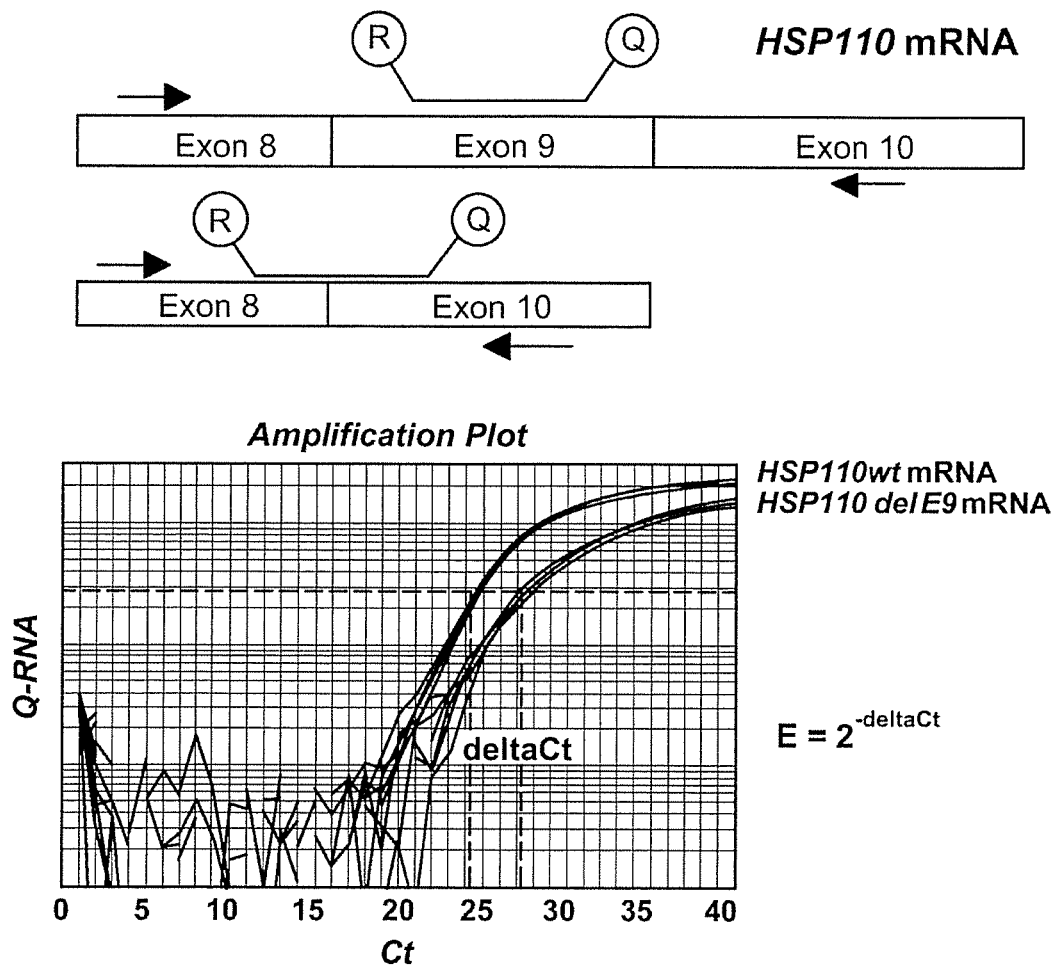
FIG. 6 depicts a diagram showing the analysis of HSP110wt and HSP110delE9 expression by RT-PCR. Amplification plots corresponding to HSP110wt and HSP110delE9 QRT-PCR products are shown. They were amplified in a competitive manner by quantitative RT-PCR using the same PCR primers but distinct internal probes which were specific for either the HSP110wt or HSP110delE9 transcript. Results are expressed (E) as N-fold difference in HSP110delE9 relative to HSP110wt expression (deltaCt), where deltaCt was determined in each case by subtracting the average Ct value of the HSP110delE9 mRNA from the average Ct value of the HSP110wt mRNA.
Figure 7:
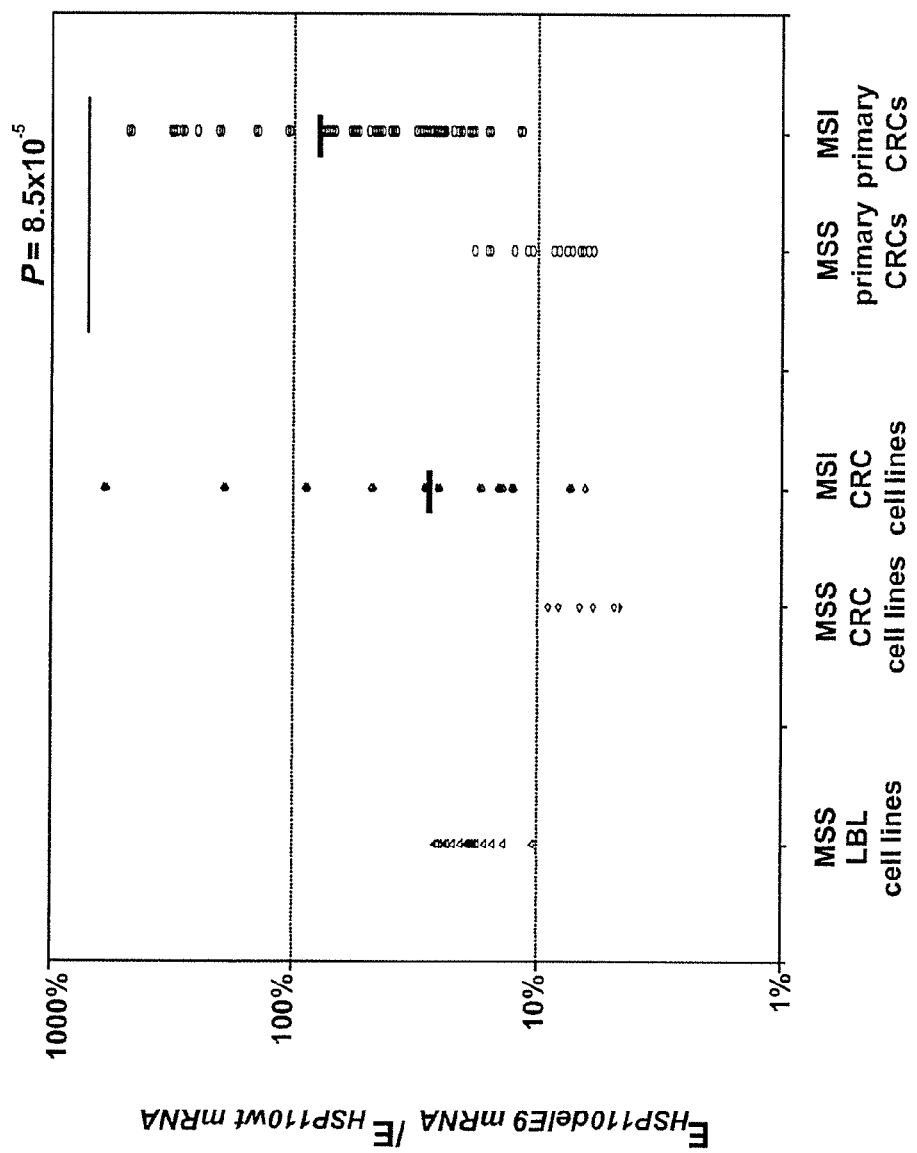
FIG. 7 depicts quantification of HSP110wt and HSP110delE9 expression in MSS and MSI cell lines and primary CRCs. Values of E ratio ($E_{HSP110delE9}/E_{HSP110wt}$) were calculated for the 14 MSI CRC cell lines and 43 primary tumour samples. As controls, we also tested MSS LBLs (N=20), MSS CRC cell lines (N=7; ALA, COLO320, SW480, FET, GLY, FRI, EB) and MSS primary CRCs (N=20). A highly significant difference was observed between MSI and MSS primary CRCs concerning HSP110delE9 expression (P=$8.5\times10^{-5}$; Student ttest). Medium E values are indicated by black bars in each case.

Overexpression of Exon 9-Negative HSP110 mRNAs (HSP110delE9) in MSI CRC Cell Lines and Primary Tumours We first confirmed by quantitative RT-PCR that the two HSP110 PCR products observed in MSI cancer cell lines corresponded to HSP110 alternative mRNAs that contained or lacked exon 9 (FIG. 6). Both HSP110 mRNA containing exon 9 (HSP110wt) and HSP110 mRNA lacking exon 9 (HSP110delE9) were quantified in a competitive manner in MSI and MSS CRC cell lines, as well as in MSS LBLs (Table 2). We observed that HSP110delE9 mRNA was weakly expressed in MSS CRC cell lines, i.e. 10-20-fold lower than HSP110wt mRNA (FIG. 7). In contrast, HSP110delE9 mRNA expression was higher in MSI CRC cell lines and was significantly different between MSI (N=43) and MSS (N=20) primary CRCs (P=8.5×10$^{-5}$; FIG. 6 and Table 2).

Figure 8:
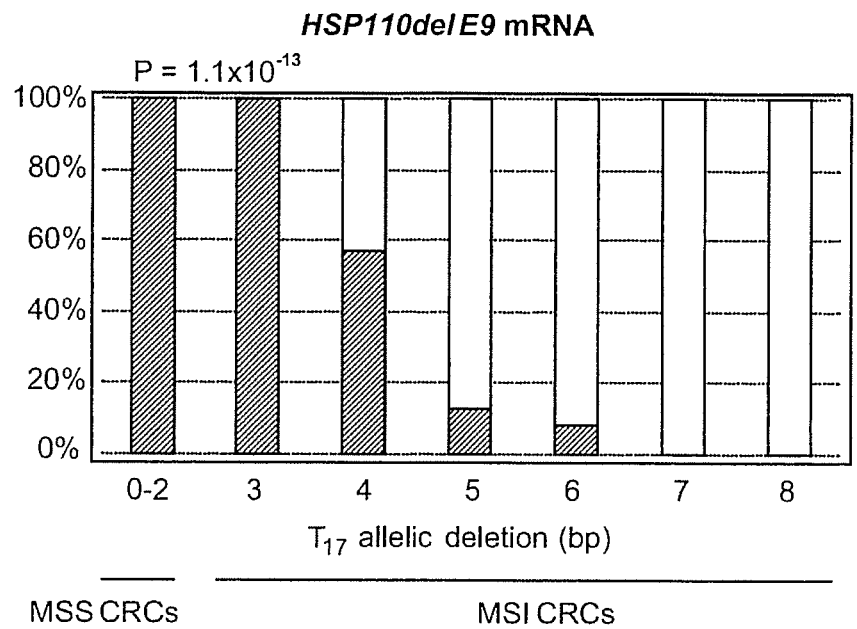
FIG. 8 depicts the correlation of $T_{17}$ repeat length and HSP110delE9 mRNA expression. Hatched and white bars correspond to CRCs in which HSP110delE9 mRNA expression was low or high, respectively, i.e. below or above the median value calculated in our tumour series. The size of the $T_{17}$ deletion was significantly different between these two groups of tumours (P=$1.1\times10^{-13}$; Student t test). HSP110delE9 mRNA was generally expressed at low levels in MSI tumours displaying small $T_{17}$ deletions, i.e. 3 or 4 base pairs, or in MSS tumours that were not mutated. In contrast, it was highly expressed in MSI tumours displaying larger $T_{17}$ deletions, i.e. from 5 to 8 base pairs.
Figure 9:
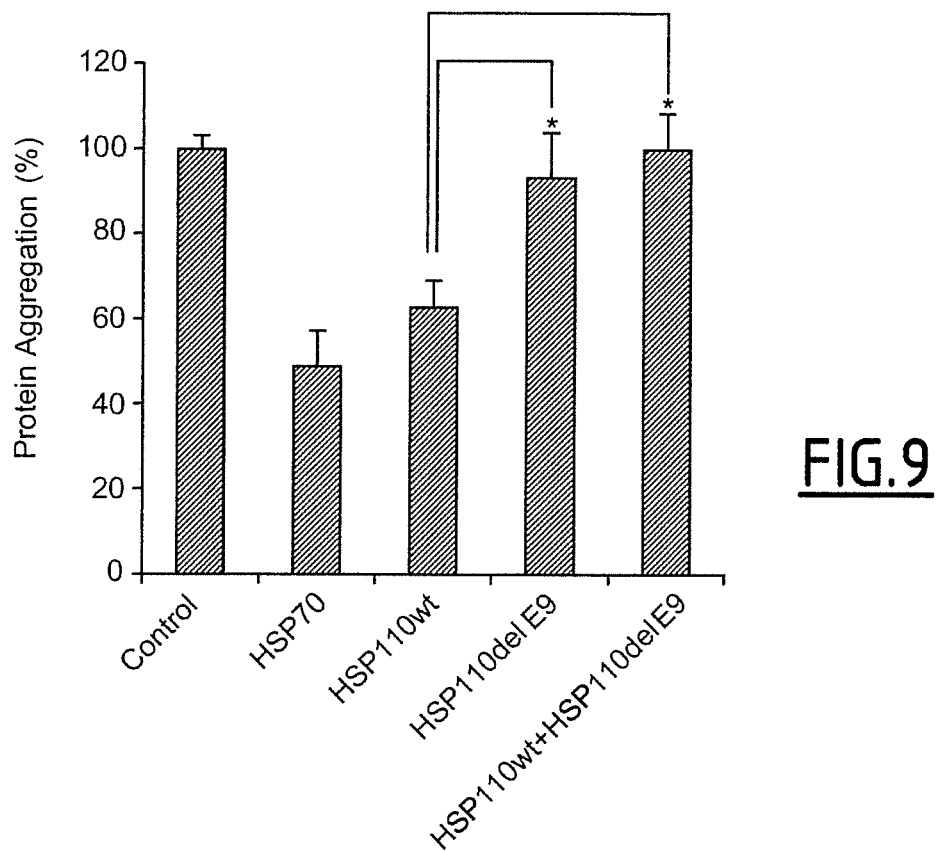
FIG. 9 depicts the effect of HSP110delE9 expression on protein aggregation. Protein extracts from MEF HSF1$^{+/+}$ cells transfected with HSP70, HSP110 and/or HSP110delE9 were heated at 55° C. for 1 h. The ratio between the initial amount of soluble protein before and after heat shock allowed to the quantification of protein aggregation. Each bar is the mean value of 4 different experiments. *P<0.05.

HSP110delE9 Expression in CRC Correlates with the Allellc Status of the HSP10 $T_{17}$ DNA Repeat We investigated whether mutation of the HSP110 $T_{17}$ intronic DNA repeat might influence the expression of HSP110 in our series of primary CRCs. The length of $T_{17}$ deletion was associated with significantly increased expression of HSP110delE9 mRNA, to the detriment of the HSP110wt transcript (FIG. 8; P=1.1×10$^{-13}$). These results were confirmed at the protein level by quantifying the amount of HSP110wt and HSP110delE9 in 10 MSI primary CRCs that displayed variable allelic shifts in the $T_{17}$ repeat (from 3 to 8 bp). Here again, a close relationship was observed using Western blot between the HSP110delE9 expression level and the length of microsatellite deletion (FIG. 9). We concluded that mutation of the HSP110 intronic $T_{17}$ microsatellite was probably the causative event leading to aberrant expression of this chaperone in colorectal tumours.

HSP110delE9 Displays Altered Chaperone Functions

Figure 3:
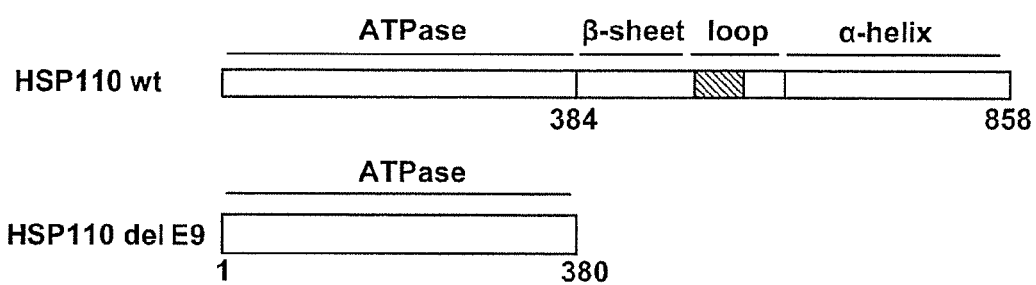
FIG. 3 depicts the structure of the wild-type HSP110 and mutated HSP110 proteins.
Figure 10:
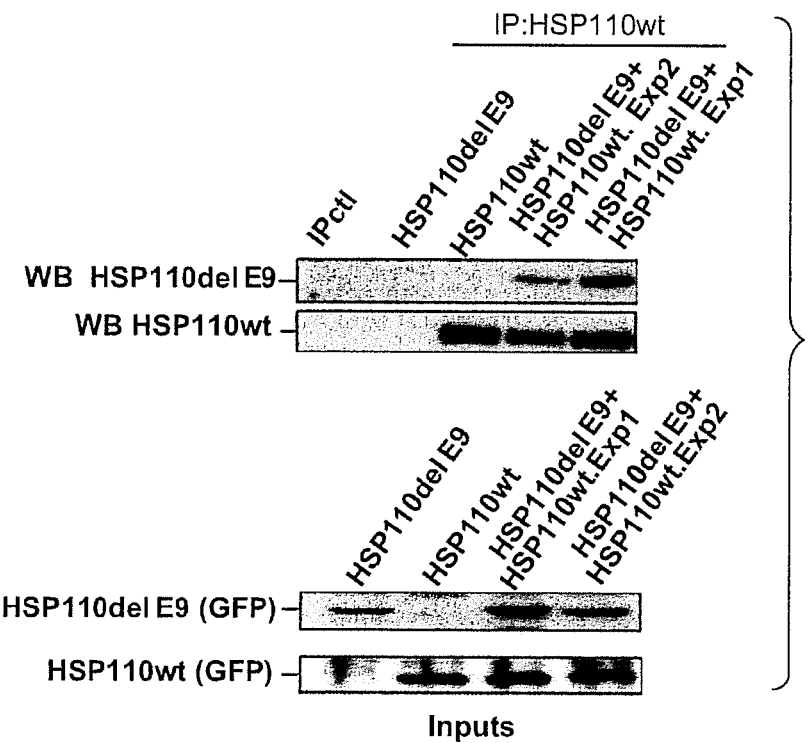
FIG. 10 depicts the analysis of HSP110delE9 to wild-type HSP110. Cell lysates from HCT116 transfected with GFP-tagged HSP110 and/or HSP110delE9 were subjected to immunoprecipitation using HSP110 that recognizes the C-terminus of HSP110. After migration, membranes were immunoblotted with GFP antibody. Inputs: protein level in total cell lysates.

The skipping of HSP110 exon 9 is frameshift and therefore generates a premature terminaison codon in exon 10 of the HSP110delE9 mRNA. HSP110delE9 is a truncated protein that contains the N-terminal ATP binding domain but is devoid of the substrate binding domain (FIG. 3). We performed several functional assays to better understand the role of increased expression of HSP110delE9 in MSI CRC cell lines. Chaperone activity was first studied using a protein thermolability assay that measures the in vitro ability of HSP110 to block protein aggregation induced by a heat shock using Murine Embryonic Fibroblasts (MEF). While HSP110wt displayed anti-aggregation activity comparable to other HSPs such as HSP70, HSP110delE9 lost this chaperone activity (FIG. 9). Interestingly, this effect was dominant negative because the anti-aggregation activity of HSP110wt was abrogated if HSP110delE9 was added at the same time (FIG. 9). HSP110 has been shown to associate with other chaperones such as HSP70 and this contributes to the overall cell chaperone network. We confirmed here in HCT116 cells that HSP110wt efficiently interacted with HSP70 and with HSP27, but not with HSP90. In contrast, HSP110delE9 lost the ability to associate with HSP70 and HSP27 but associated strongly with HSP110wt, in line with its dominant negative effect (FIG. 10). Finally, HSP110delE9 displayed an altered cellular localization compared to HSP110wt. While the latter was found both in the nucleus and cytosol, HSP110delE9 was restricted to the cytosol.

Figure 11:
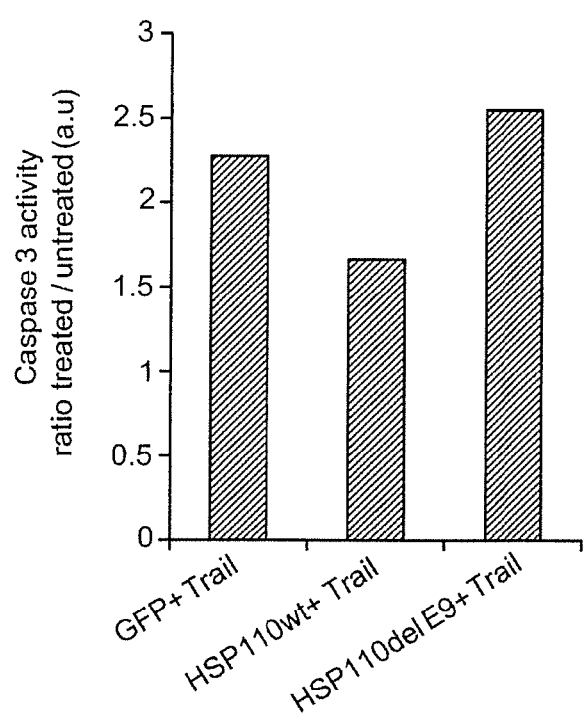
FIG. 11 depicts the effect of HSP110delE9 on apoptosis. HCT116 cells transfected with GFP-tagged HSP110, HSP110delE9 or an empty vector (GFP) were treated with recombinant TRAIL ligand (5 h) at the indicated doses. Apoptosis was measured by FACS analysis of caspase 3 activity.
Figure 12:
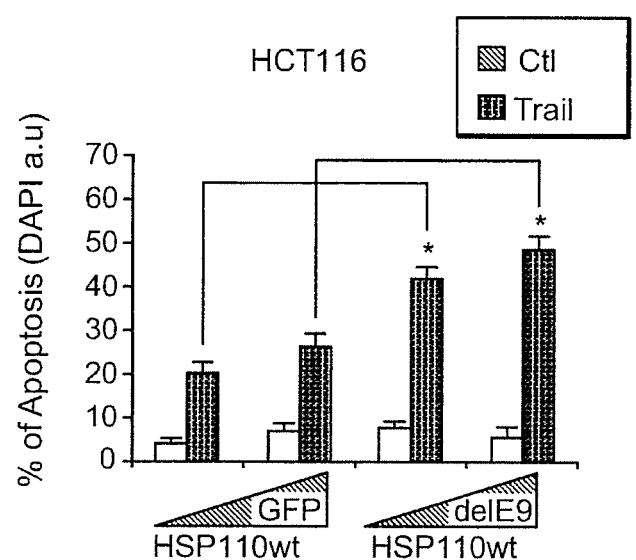
FIG. 12 depicts the effect of increasing dose of HSP110delE9 on apoptosis. HCT116 cells transfected with GFP-tagged HSP110 and increased doses of HSP110delE9 or an empty vector (GFP) were treated with recombinant TRAIL ligand (60 ng/ml, 5 h) and the percentage of apoptosis was determined by DAPI staining (chromatin condensation).
Figure 13:
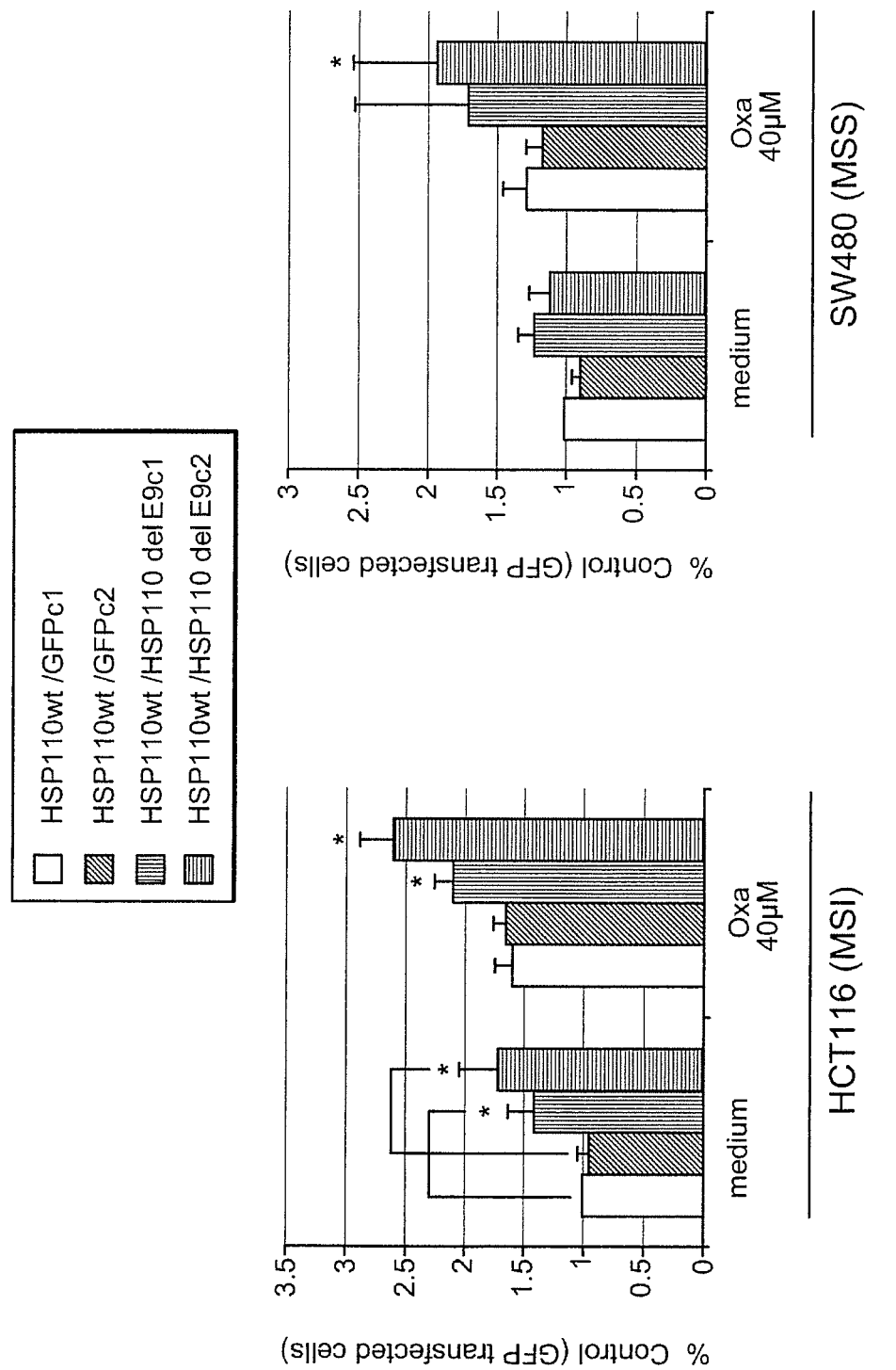
FIG. 13 depicts the pro-apoptotic effect of HSP110delE9 on tumor cells treated with a chemotherapeutic agent. HCT116 (MSI) or SW480 (MSS) cells were transfected with HSP110wt (1.5 μg) and co-transfected with two different doses (0.5 and 1 μg) of either GFP-empty vector or HSP110delE9. After treatment with oxaliplatin (Oxa, 40 μM, 48 h), apoptosis was assessed by FACS analysis. *P<0.05.

HSP110delE9 Blocks HSP10wt Anti-Apoptotic Function and Sensitizes Cancer Cells to Oxaliplatin A number of studies have previously described the anti-apoptotic role of HSP110. We therefore investigated the effect on apoptosis of the HSP110 truncation due to exon 9 skipping. HCT116 cells were transfected with HSP110wt or HSP110delE9 and apoptosis was triggered using the cell death factor, TRAIL (Tumor necrosis factor-related-apoptosis-inducing ligand). As expected, TRAIL induced dose dependent apoptosis and HSP110wt exerted a protective effect, as demonstrated by the appearance of well known apoptotic markers including caspase-8 cleavage, caspase-3 activity, cleavage of the caspase-3 target PARP, mitochondrial membrane permeation and nuclear condensation (FIG. 11). In contrast, HSP110delE9 not only lacked the protective properties of HSP110wt but was also able to block its anti-apoptotic function in a dose-dependent manner (FIG. 12). Probably as a consequence, the over-expression of HSP110delE9 in various MSI (HCT116, LoVo) but also MSS (SW480) CRC cell lines increased their sensitivity to anticancer agents such as oxaliplatin, a commonly used drug in the acdjuvant treatment of CRC patients (FIG. 13).

HSP110delE9 Impacts Patient Survival and Response to Chemotherapy

Figure 14:
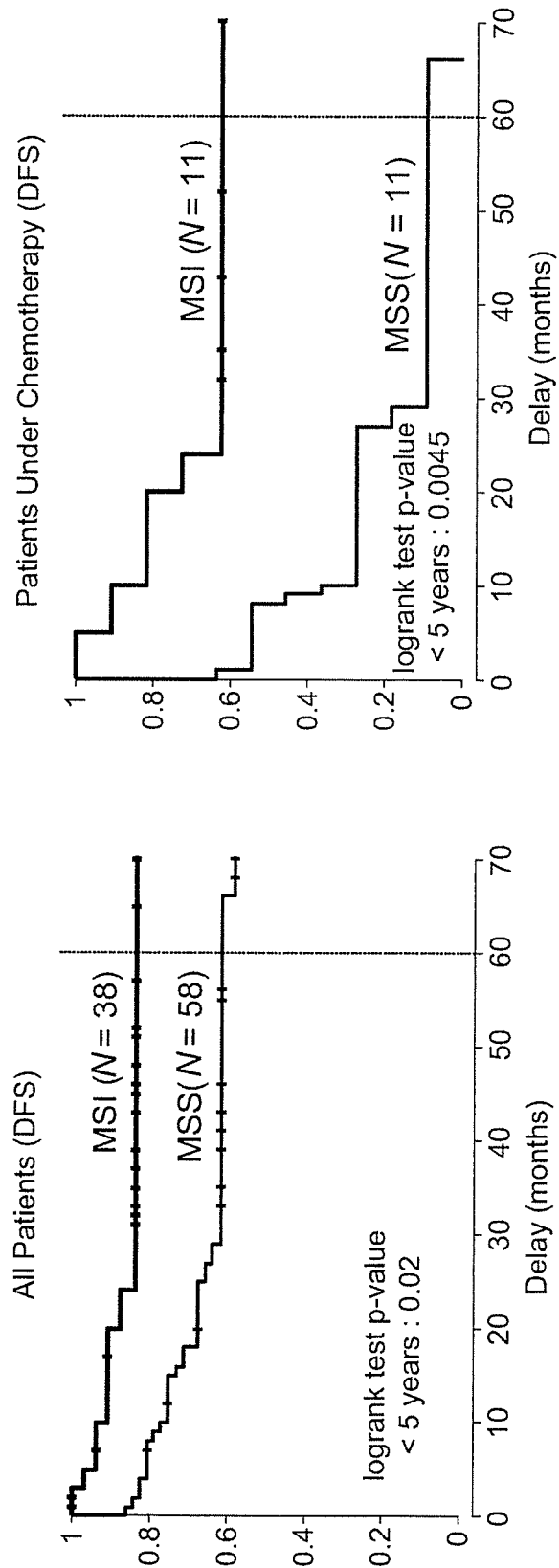
FIG. 14 depicts Kaplan-Meier univariate analyses of disease-free survival (DFS) in patients with MSI or MSS CRCs. For statistical analyses, only the first 5 years are shown. Expectedly, the following clinicopathological characteristics of patients with MSI or MSS CRCs were different, i.e. Dukes' stage (P=$2.6\times10^{-4}$; Fisher exact test), age at diagnosis (P=$2.9\times10^{-5}$) and tumour location (P=$5\times10^{-4}$).
Figure 15:
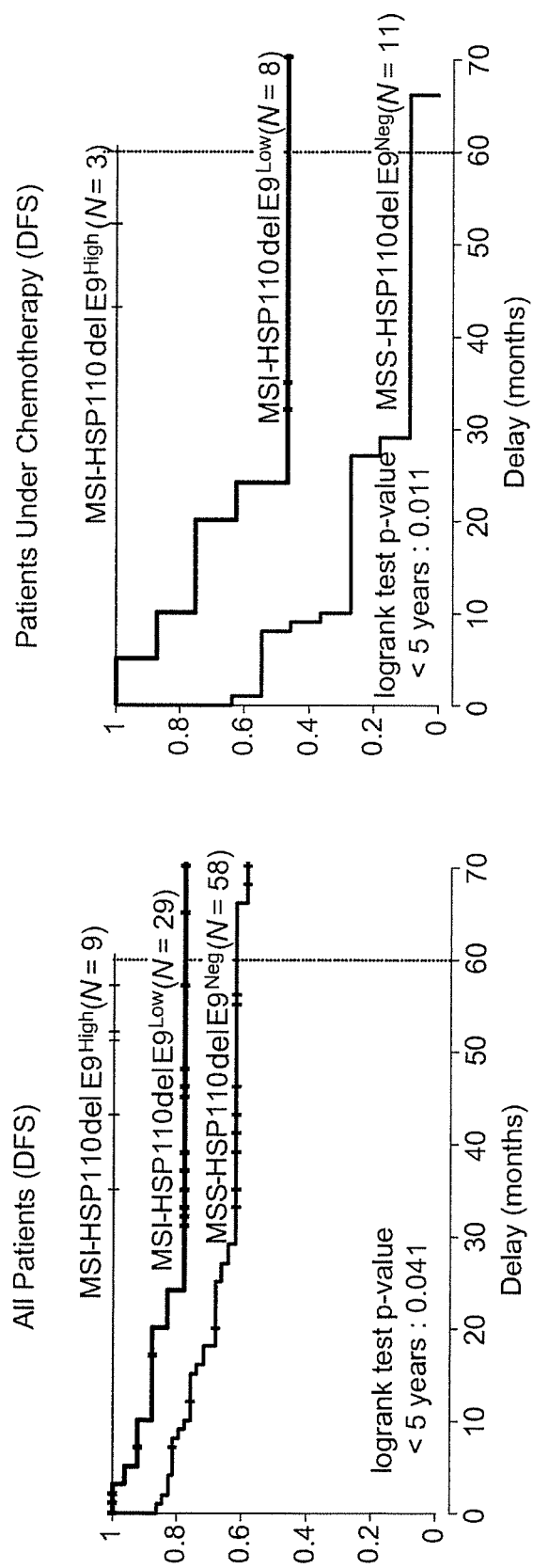
FIG. 15 depicts Kaplan-Meier estimates of DFS in different groups of CRC patients according to HSP110 expression. Univariate analysis was performed as in FIG. 1. The following clinicopathological characteristics of patients with MSI-HSP110delE9$^{High}$ (N=9; 24%) or MSI-HSP110delE9$^{Low}$ (N=29; 76%) tumours were not significantly different, i.e. Dukes' stage, tumour location, gender, BRAF, KRAS and PIK3CA gene mutation status, CIMP and CIN status, frameshift mutations in target genes for MSI, MLH1 and MGMT methylation status.

We next investigated whether HSP110delE9 was of clinical significance by evaluating the expression of HSP110delE9 mRNA relative to HSP110wt transcript in CRC. In all, 38 MSI and 58 MSS CRC patients with clinical data were included in this study. We stratified MSI tumours into two groups according to the level of HSP110delE9 expression, i.e. MSI-HSP110delE9$^{High}$ (N=9; 24%) and MSI-HSP110delE9$^{Low}$ (N=29; 76%) tumours in which the HSP110delE9/HSP110wt mRNA ratio was above and below 75%, respectively (FIG. 6). As expected, the disease-free survival (DFS) of patients was positively associated with their tumour MSI status (FIG. 14). Furthermore, MSI-HSP110delE9$^{High}$ patients displayed excellent DFS and response to chemotherapy, in contrast to MSS-HSP110delE9$^{Neg}$ patients that did not express HSP110delE9 and to MSI-HSP110delE9$^{Low}$ patients (FIG. 15). Importantly, no significant difference in the dinicopathological characteristics of patients with MSI-HSP110delE9$^{High}$ and MSI-HSP110delE9$^{Low}$ tumours was observed, including Dukes stage, patient age and gender, primary tumour location and KRAS and BRAF mutation status (Table 3).

TABLE 3

Association between clinicopathological variables and HSP110del9 expression in MSI CRCs (Fisher exact test p-values, t-test p-values for Age):

| Annotation | Modality | P value | Patients with MSI-HSP110delE9$^{High}$ CRC | Patients with MSI-HSP110delE9$^{Low}$ CRC |
|---|---|---|---|---|
| Dukes' stage | B | 1 | 6 (11%) | 18 (7%) |
| Dukes' stage | C | 1 | 3 (22%) | 11 (7%) |
| Tumour.Location | left colon | 0.34 | 1 (12%) | 9 (32%) |
| Tumour.Location | right colon | 0.34 | 7 (88%) | 19 (68%) |
| Sex | F | 0.45 | 5 (56%) | 11 (38%) |
| Sex | M | 0.45 | 4 (44%) | 18 (62%) |
| BRAF Gene.mutation.Status | Mutated | 1 | 3 (33%) | 11 (39%) |
| BRAF Gene.mutation.Status | Wild-Type | 1 | 6 (67%) | 17 (61%) |
| KRAS Gene.mutation.Status | Mutated | 1 | 2 (22%) | 6 (21%) |
| KRAS Gene.mutation.Status | Wild-Type | 1 | 7 (78%) | 22 (79%) |
| PIK3CA Gene.mutation.Status | Mutated | 1 | 1 (11%) | 4 (15%) |
| PIK3CA Gene.mutation.Status | Wild-Type | 1 | 8 (89%) | 22 (85%) |
| CIMP | Negatif | 1 | 3 (33%) | 10 (36%) |
| CIMP | Positif | 1 | 6 (67%) | 18 (64%) |
| CIN | Low | 1 | 7 (100%) | 27 (93%) |
| CIN | High | 1 | 0 (0%) | 2 (7%) |
| ATR* Gene.mutation.Status | Mutated | 0.45 | 6 (67%) | 14 (48%) |
| ATR* Gene.mutation.Status | Wild-Type | 0.45 | 3 (33%) | 15 (52%) |
| BAX* Gene.mutation.Status | Mutated | 1 | 5 (56%) | 14 (48%) |
| BAX* Gene.mutation.Status | Wild-Type | 1 | 4 (44%) | 15 (52%) |
| BLM* Gene.mutation.Status | Mutated | 0.42 | 4 (44%) | 8 (28%) |
| BLM* Gene.mutation.Status | Wild-Type | 0.42 | 5 (56%) | 21 (72%) |
| GRB14* Gene.mutation.Status | Mutated | 1 | 4 (44%) | 11 (38%) |
| GRB14* Gene.mutation.Status | Wild-Type | 1 | 5 (56%) | 18 (62%) |
| GRK4* Gene.mutation.Status | Mutated | 1 | 3 (33%) | 8 (28%) |
| GRK4* Gene.mutation.Status | Wild-Type | 1 | 6 (67%) | 21 (72%) |

TABLE 3-continued

Association between clinicopathological variables and HSP110del9 expression in MSI CRCs (Fisher exact test p-values, t-test p-values for Age):

| Annotation | Modality | P value | Patients with MSI-HSP110delE9$^{High}$ CRC | Patients with MSI-HSP110delE9$^{Low}$ CRC |
|---|---|---|---|---|
| IGF2R* Gene.mutation.Status | Mutated | 1 | 4 (44%) | 12 (41%) |
| IGF2R* Gene.mutation.Status | Wild-Type | 1 | 5 (56%) | 17 (59%) |
| RAD50* Gene.mutation.Status | Mutated | 0.15 | 7 (78%) | 14 (48%) |
| RAD50* Gene.mutation.Status | Wild-Type | 0.15 | 2 (22%) | 15 (52%) |
| RBBP8* Gene.mutation.Status | Mutated | 0.32 | 3 (33%) | 4 (14%) |
| RBBP8* Gene.mutation.Status | Wild-Type | 0.32 | 6 (67%) | 25 (86%) |
| RECQL* Gene.mutation.Status | Mutated | 0.31 | 0 (0%) | 5 (17%) |
| RECQL* Gene.mutation.Status | Wild-Type | 0.31 | 9 (100%) | 24 (83%) |
| TCF4* Gene.mutation.Status | Mutated | 1 | 4 (44%) | 13 (45%) |
| TCF4* Gene.mutation.Status | Wild-Type | 1 | 5 (56%) | 16 (55%) |
| MLH1 Gene.methylation.Status | Methylated | 0.71 | 6 (67%) | 16 (55%) |
| MLH1 Gene.methylation.Status | Unmethylated | 0.71 | 3 (33%) | 13 (45%) |
| MGMT Gene.methylation.Status | Methylated | 0.45 | 4 (44%) | 18 (62%) |
| MGMT Gene.methylation.Status | Unmethylated | 0.45 | 5 (56%) | 11 (38%) |

NA: Non Applicable.
*Mutations at coding microsatellite sequences MSI (target genes).

Example 3

Discussion

Like other stress inducible HSPs, HSP110 protects the cell against adverse conditions. However, HSP110 also provides specific critical functions since hsp110 gene knock-out in both yeast and Drosophila is lethal (Trott et al., Genetics 170 (3), 1009 (2005)). HSP110 not only acts as a nucleotide exchange factor for HSP70 (Andreasson et al., Proceedings of the National Academy of Sciences of the United States of America 105 (43), 16519 (2008)) but also possesses chaperone anti-aggregation activity. It is approximately four-fold more efficient at binding and stabilizing denatured protein substrates compared to HSC70 and HSP70 (Wang et al., Cancer research 63 (10), 2553 (2003)). Because of its strong chaperone (or holder) function, HSP110 is a very good antigen carrier and is therefore being used as an extracellular protein in vaccine formulation (Manjili et al., Cancer research 62 (6), 1737 (2002); Manjili et al., J Immunol 171 (8), 4054 (2003)). HSP110 chaperone activity is ATP-independent but requires the substrate binding domain of the protein. The truncated HSP110 form (HSP110delE9) due to exon 9 skipping identified here in MSI CRC lacks the substrate binding domain. As a consequence, it has lost its HSP110 anti-aggregation chaperone function and is unable to bind HSP70, thereby also losing its function as a nucleotide exchange factor for HSP70 proteins.

A possible explanation for HSP110 overexpression in CRC cells (Kai et al., Oncology reports 10 (6), 1777 (2003)) is that they must extensively rewire their metabolic and signal transduction pathways, thereby becoming dependent on proteins that are dispensable for the survival of normal cells. The tumourigenic properties of HSP110, although not fully understood, may in part be explained by its anti-apoptotic properties (Ceballos et al., Oncogene 24 (28), 4559 (2005); Gotoh et al., FEBS letters 560 (1-3), 19 (2004)). Overexpression of HSP110 has been shown to protect against apoptotic cell death in different cellular models including colon cancer. Inversely, small interfering RNA-mediated depletion of HSP110 induces apoptosis in HCT116 cells (Hosaka et al., Cancer science 97 (7), 623 (2006)). Interestingly, we showed in this work that a similar induction of apoptosis in HCT116 cells was achieved by overexpression of the mutant HSP110delE9. Significant levels of HSP110delE9 expression were restricted to colon cancer cells displaying MSI, thus disadvantaging their survival. Indeed, HSP110delE9 has not only lost the normal HSP110 anti-apoptotic properties but also associates with HSP110 to block these protective functions in a dose-dependent manner. Further, when overexpressed in both MSI and MSS CRC cells, HSP110delE9 sensitizes these cells to apoptosis induced by chemotherapeutic drugs. It is worth noting these pro-apoptotic effects are especially observed when HSP110delE9 expression is similar or higher to that of HSP110wt, as shown by our transfection experiments. This is probably due to the fact that each molecule of HSP110delE9 forms a complex with one molecule of HSP110wt, thus neutralizing its function in a dominant manner.

The reason for the selection and expression of endogenous HSP110delE9 dominant negative pro-apoptotic mutant in MSI CRCs is unclear. A possible explanation is that long, non coding mononucleotide repeats such as the $T_{17}$ located in HSP110 intron 8 are often hotspots for mutations in MSI tumours due to the MMR deficiency (Suraweera et al., Gastroenterology 123 (6), 1804 (2002); Buhard et al., J Clin Oncol 24 (2), 241 (2006)). Whereas most of these microsatellites are functionally anonymous, a few are endowed with biological activity. Even though they result in a tumour suppressor effect, frequent mutation of these sequences can occur, as shown in the current work, thus representing the Achilles' heel of the MSI-driven tumourigenic process. All the MSI tumour samples tested here were mutated at the $T_{17}$ repeat of HSP110 and displayed accumulation of HSP110delE9 at variable levels. Those with high expression levels of HSP110delE9 mRNA, i.e. above the threshold of 75% of HSP110wt, represented about 25% of MSI colon tumours. In line with our in vitro results, they were associated with excellent survival and with response to chemotherapy. On the other hand, CRC patients with MSI-HSP110delE9$^{Low}$ showed intermediate survival as compared to MSI-HSP110delE9$^{High}$ and MSS CRC patients.

Overall, these results are highly suggestive of a dose-dependent clinical effect of HSP110delE9 expression in CRC. Further studies using larger series of CRC patients are necessary to understand how the endogenous expression of this mutant might impact both their prognosis and response to treatment We anticipate that HSP110delE9 should also display aberrant expression in MSI cancers from other primary locations such as stomach, endometrium and other more recently reported sites (Duval et al., *Proceedings of the National Academy of Sciences of the United States of America* 101 (14), 5002 (2004)). Besides, the targeting of HSPs has emerged as an interesting sensitization strategy in cancer therapy. This is driven by the knowledge that HSPs may have oncogene-like functions and mediate "non-onco-gene addiction" of stressed tumour cells that must adapt to a hostile microenvironment. Different inhibitors of HSP90 (eg. 17-allylamino, 17-demethoxygeldanamycin, 17AAG), HSP27 (eg. the oligonucleotide OGX-427) and HSP70 (eg. HSP70 peptide aptamers (Rerole et al., *Cancer research* 71 (2), 484 (2011))) are currently being evaluated in cancer patients, with some already in phase II/III clinical trials (Jego et al., *Cancer letters*). Interestingly, the present work is the first report of an HSP inhibitor that is produced endogenously by the cell. We are presently designing small peptides that mimic the sensitizing function of HSP110delE9 and could therefore be readily adapted for cancer therapy.

Example 4

The HSP110delE9 transcript contains a premature stop codon (PTC). Consequently, it is partially degraded by the NMD system in the tumor cells. Experiments were carried out, and it was demonstrated that the HSP110delE9 transcript was partially degraded by the NMD system, like other PTC+mRNA-generated through MSI in MSI colon cancer cell. The re-expression of HSP110delE9 consequently causes apoptosis of MSI colon tumor cell lines (data not shown). Synthesis of chemical or biological compounds mimicking the HSP110delE9 activity in tumor cells, in particular mimicking its anti-apoptotic effect may have a major therapeutical interest in the treatment of CRCs. In the same way, the use of compounds susceptible to promote the HSP110delE9 expression in the tumor cells would be of great interest. It is notably the case of compounds inhibiting the Nonsense mediated-mRNA decay (NMD) system. Different pharmacological inhibitors of NMD are now available. They can be used to reproduce these experiments, both in vitro in different cell models and in animal models (nude mice xenografted with MSI CRC in first-line).

Example 5

Methods

Patients and Specimens 365 patients who underwent surgical resection of histologically proven colorectal adenocarcinomas displaying an unambiguous MSI phenotype in one of the 6 clinical centres are identified in this study (Hôpital Saint-Antoine, Paris, France; CHU de Dijon, Dijon, France; CHU de Toulouse Purpan, Toulouse, France; Centre Antoine Lacassagne, Nice, France; St John of God Pathology, Subiaco, Australia; National University Hospital, Singapore). For these patients, clinical data were available and tumor tissue could be retrieved from the tumor collection. The study was conducted according to the recommendations of the institutional authorities. Patients with MSI CRC were treated with 5-fluorouracil plus leucovorin, either alone or in combination with other drugs such as oxaliplatin. Recurrence was uniformly assessed, i.e. physical examination with biological tests and measurement of carcino-embryonic antigen level, pulmonary X-ray and abdominal ultrasonography or computed tomography every 3 months during the first 3 years after surgery, then every 6 months for 2 years, and then annually. Patient follow-up was defined as the time between surgery and the last hospital contact or disease recurrence. In this study, the relapse-free survival was examined in a cohort of 282 MSS CRC patients that matched for age, gender, primary tumor location and tumor staging (Tables 4 to 7).

TABLE 4

Univariate analysis in Stage II & III MSI & MSS CRC Patients.

| | | | | | UNIVARIATE ANALYSIS | | |
|---|---|---|---|---|---|---|---|
| Annotation | Value | N | n. event | H.R. | 95% C.I. | P value modality | P value model |
| Stage (ref = II) | III | 587 | 142 | 2.4 | 1.7-3.4 | 1.50E−07 | 5.98E−08 |
| Age (ref = <75 y) | ≥75 y | 587 | 142 | 1.6 | 1.1-2.2 | 0.0081 | 0.0076 |
| Chemotherapy (ref = no) | Y | 587 | 142 | 1.5 | 1.1-2.2 | 0.018 | 0.017 |
| HSP110 Del (ref = small) | Large | 587 | 142 | 0.57 | 0.32-1 | 0.063 | 0.060 |
| HNPCC (none) | HNPCC | 166 | 35 | 0.42 | 0.16-1.1 | 0.073 | 0.064 |
| Tumor Location (ref = Left Colon) | Right Colon | 582 | 140 | 1.5 | 0.99-2.4 | 0.058 | 0.070 |
| | Rectum | 582 | 140 | 0.42 | 0.057-3.1 | 0.4 | 0.070 |
| MSI Status (ref = MSI) | MSS | 587 | 142 | 1.3 | 0.92-1.8 | 0.15 | 0.15 |
| Gender (ref = F) | M | 587 | 142 | 0.83 | 0.59-1.2 | 0.27 | 0.26 |
| Chemotherapy Type (ref = FOLFOX) | LV5FU2 | 126 | 41 | 0.95 | 0.5-1.8 | 0.88 | 0.88 |

TABLE 5

Multivariate analysis in Stage II & III MSI & MSS CRC Patients.

| Annotation | Value | N | H.R. | 95% C.I. | P value modality | P value model |
|---|---|---|---|---|---|---|
| Stage (ref = II) | III | 582 | 2.4 | 1.6-3.6 | 3.90E−05 | 2.60E−07 |
| Age (ref = <75 y) | ≥75 y | 582 | 1.4 | 0.98-2.1 | 0.062 | |
| Chemotherapy (ref = no) | Y | 582 | 1.1 | 0.67-1.7 | 0.8 | |
| HSP110 Del (ref = small) | Large | 582 | 0.51 | 0.27-0.97 | 0.041 | |
| HNPCC (none) | HNPCC | | | | | |
| Tumor Location (ref = Left Colon) | Right Colon | 582 | 1.4 | 0.87-2.2 | 0.17 | |
| | Rectum | 582 | 0.45 | 0.06-3.3 | 0.43 | |
| MSI Status (ref = MSI) | MSS | 582 | 1.2 | 0.81-1.6 | 0.44 | |
| Gender (ref = F) | M | 582 | 0.96 | 0.67-1.4 | 0.82 | |
| Chemotherapy Type (ref = FOLFOX) | LV5FU2 | | | | | |

TABLE 6

Univariate analysis in Stage III MSI & MSS CRC Patients.

| Annotation | Value | N | n. event | H.R. | 95% C.I. | P value modality | P value model |
|---|---|---|---|---|---|---|---|
| HSP110 Del (ref = small) | Large | 171 | 66 | 0.17 | 0.042-0.7 | 0.014 | 0.0051 |
| MSI Status (ref = MSI) | MSS | 171 | 66 | 1.5 | 0.91-2.4 | 0.11 | 0.11 |
| Chemotherapy. Adj. Performed | Y | 171 | 66 | 0.7 | 0.43-1.1 | 0.15 | 0.15 |
| Gender (ref = F) | M | 171 | 66 | 0.72 | 0.43-1.2 | 0.21 | 0.21 |
| HNPCC (none) | HNPCC | 45 | 14 | 0.51 | 0.12-2.3 | 0.38 | 0.38 |
| Chemotherapy Type (ref = FOLFOX) | LV5FU2 | 89 | 33 | 0.75 | 0.37-1.5 | 0.43 | 0.42 |
| Tumor Location (ref = Left Colon) | Right Colon | 168 | 65 | 1.3 | 0.68-2.3 | 0.46 | 0.75 |
| | Rectum | 168 | 65 | 1 | 0.13-7.7 | 0.99 | 0.75 |
| Age (ref = <75 y) | ≥75 y | 171 | 66 | 1 | 0.64-1.7 | 0.86 | 0.86 |

TABLE 7

Multivariate analysis in Stage III MSI & MSS CRC Patients.

| Annotation | Value | N | H.R. | 95% C.I. | P value modality | P value model |
|---|---|---|---|---|---|---|
| HSP110 Del (ref = small) | Large | 168 | 0.17 | 0.041-0.73 | 0.017 | 0.045 |
| MSI Status (ref = MSI) | MSS | 168 | 1.2 | 0.71-2 | 0.5 | |
| Chemotherapy. Adj. Performed | Y | 168 | 0.61 | 0.33-1.1 | 0.1 | |
| Gender (ref = F) | M | 168 | 0.71 | 0.4-1.2 | 0.22 | |
| HNPCC (none) | HNPCC | | | | | |
| Chemotherapy Type (ref = FOLFOX) | LV5FU2 | | | | | |
| Tumor Location (ref = Left Colon) | Right Colon | 168 | 1.3 | 0.67-2.5 | 0.43 | |
| | Rectum | 168 | 1.3 | 0.16-10 | 0.81 | |
| Age (ref = <75 y) | ≥75 y | 168 | 0.71 | 0.38-1.3 | 0.26 | |

Microsatellite-Instability Analysis of the $T_7$ Repeat in HSP110

Tumor DNA from samples was extracted using the QIAamp DNA Tissue Kit (Qiagen). To evaluate MSI or MMR-deficient status, pentaplex PCR or immunoperoxidase staining on formalin-fixed tumor tissue using MLH1, MSH2, MSH6 or PMS2 primary antibodies, were respectively performed. The mutation status of HSP110 $T_{17}$ was evaluated by PCR and fluorescence genotyping in the series of 365 MSI CRC samples and in a control series of 405 MSS colon tumor samples (including the 282 CRCs we used to examine relapse-free survival in MSS CRC patients), as described in Dorard and al., *Nature Medicine* 17:1283-1289 (2011).

Statistical Analysis

For the analysis of associations with patient outcome, relapse-free survival was used and defined as the time from surgery to the first recurrence (relapse or death). Survival curves were obtained according to the method of Kaplan and Meier and differences between survival distributions were assessed by log-rank test using an end point at five years. Univariate and multivariate models were computed using Cox proportional-hazards regression. For multivariate analyses, as all variables have to be assessed on the same samples to be comparable, variables available only for a subset of samples were not included in the multivariate model.

To find the minimum size of $T_{17}$ deletion in HSP110 that was associated with clinical outcome, the analyses were performed on stage III patients from the previously studied cohort described in Dorard and al., Nature Medicine 17:1283-1289 (2011). All thresholds defining two classes of deletion size (from 2 to 5 base pairs) were tested. The selected threshold was the one showing the most significant association with outcome. All tumors were thus classified into two classes, representing large ($Del^L$) and small ($Del^S$) HSP110 deletion. Subdivision among the class of small deletion tumors was investigated in the same manner, but using the stage III patients for the whole dataset in order to have sufficient sample size.

Differences between HSP110 deletion size groups and other clinical annotations were tested for statistical significance using the Fisher exact test for categorical variables, or an unpaired Student's t-test for continuous variables.

Adjustment of the MSS CRC population to stage II and III MSI CRC was confirmed by evaluating differences between MSI status and other clinical annotations as described above for the two HSP110 size groups.

For all the analyses, P values of less than 0.05 were considered to indicate statistical significance.

Results

HSP110 $T_{17}$ Status of MSI and MSS CRC

The study population consisted of a consecutive, multicentre, retrospective series of 365 patients with pathologically confirmed colorectal adenocarcinoma that unambiguously displayed MSI using well established criteria.

Figure 17:
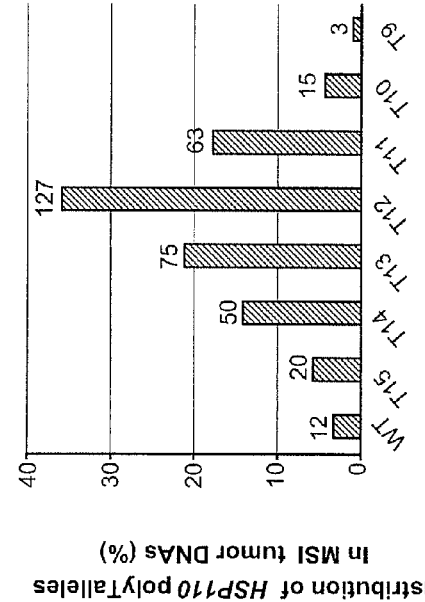
FIG. 17 depicts the distribution of mutated HSP110 $T_{17}$ alleles in MSI CRCs.
Figure 16:
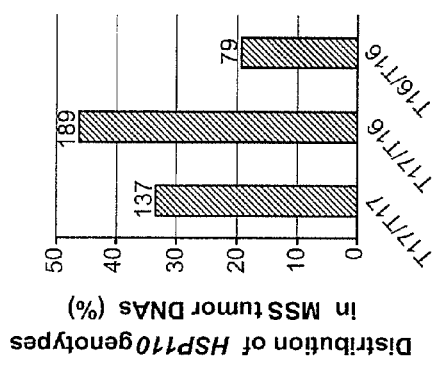
FIG. 16 depicts the distribution of HSP110 $T_{17}$ genotypes in 405 MSS CRCs.

The status of HSP110 $T_{17}$ was evaluated in a control series of 405 MSS CRCs (5.2% stage 0, 18.5% stage I, 20.5% stage II, 21.7% stage III, 14.3% stage IV, 19.8% unknown). As shown in FIG. 16 allelic lengths were either $T_{16}$ or $T_{17}$ in all cases, inside the reported polymorphic zone[6]. Of the 365 MSI tumors, 353 (96.7%) showed deletions of up to 7 base pairs that were outside the polymorphic zone. The frequency and distribution of the different HSP110 mutant $T_{17}$ alleles in MSI CRCs are shown in FIG. 17.

HSP110 $T_{17}$ Mutation Status and the Survival of MSI CRC Patients

Figure 18:
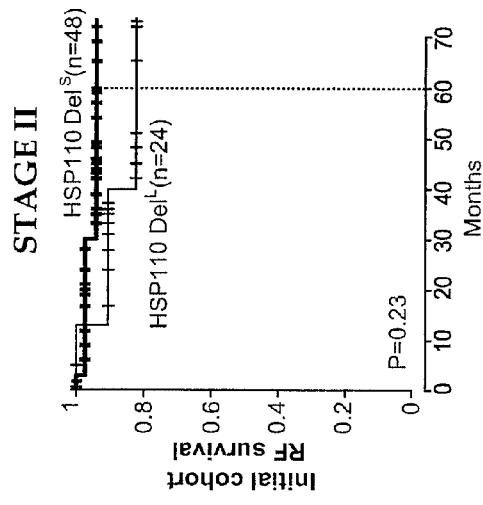
FIG. 18 depicts the survival analysis of stage II and stage III MSI CRC patients from the initial cohort according to the size of deletions in the HSP110 $T_{17}$ DNA repeat. Patients are classified into two groups according to the size of deletion in the $T_{17}$ intronic repeat of HSP110 (ΔT≥5 bp, $T_{11}$, $T_{10}$, $T_9$ for MSI HSP110Del$^L$ patients; 0≤ΔT<5, $T_{17}$ to $T_{12}$ for MSI HSP110Del$^S$ patients).
Figure 18:
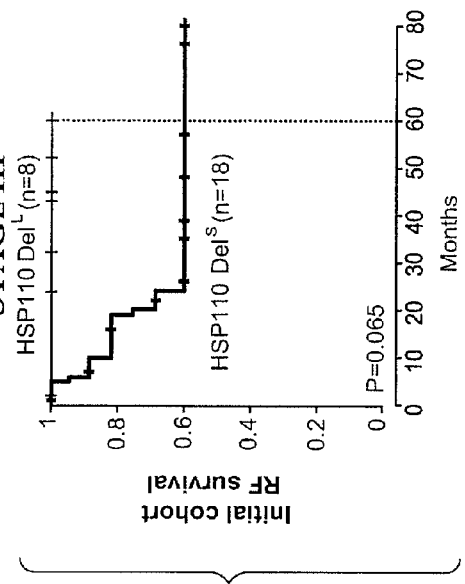
Figure 19:
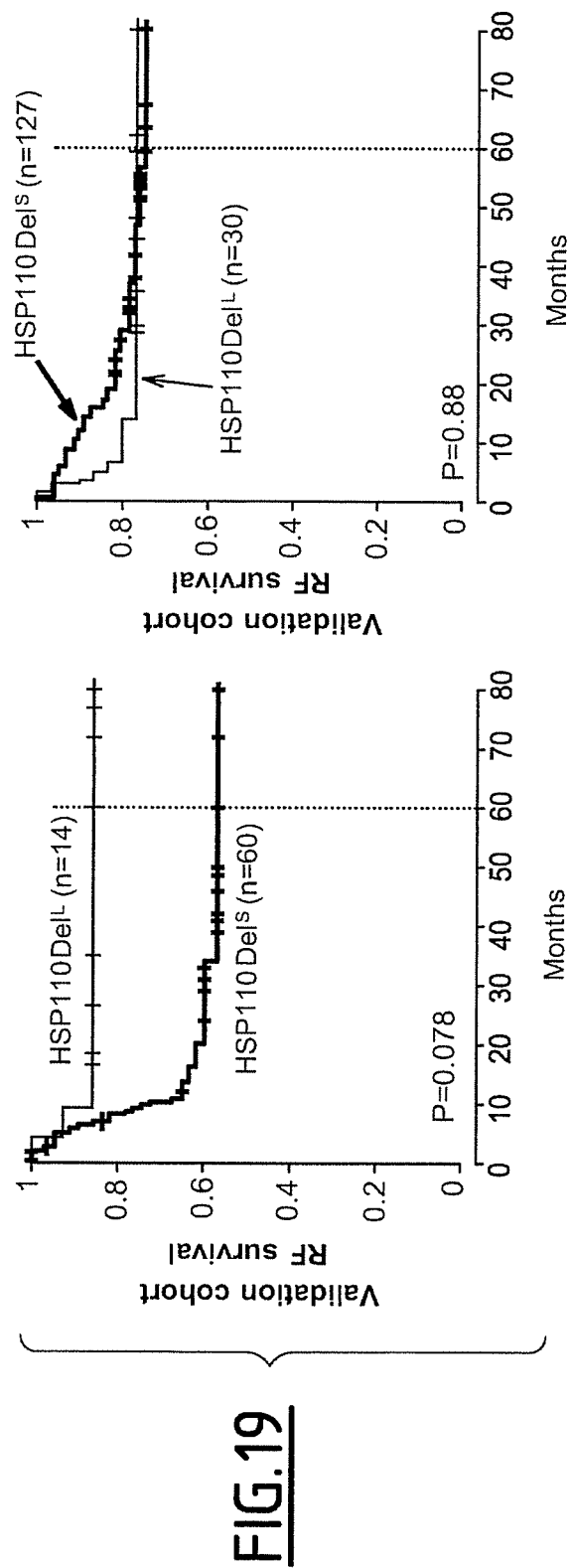
FIG. 19 depicts the survival analysis of stage II and stage III MSI CRC patients from the validation cohort according to the size of deletions in the HSP110 $T_{17}$ DNA repeat. Patients are classified into two groups according to the size of deletion in the $T_{17}$ intronic repeat of HSP110 (ΔT≥5 bp, $T_{11}$, $T_{10}$, $T_9$ for MSI HSP110Del$^L$ patients; 0≤ΔT<5, $T_{17}$ to $T_{12}$ for MSI HSP110Del$^S$ patients).
Figure 20:
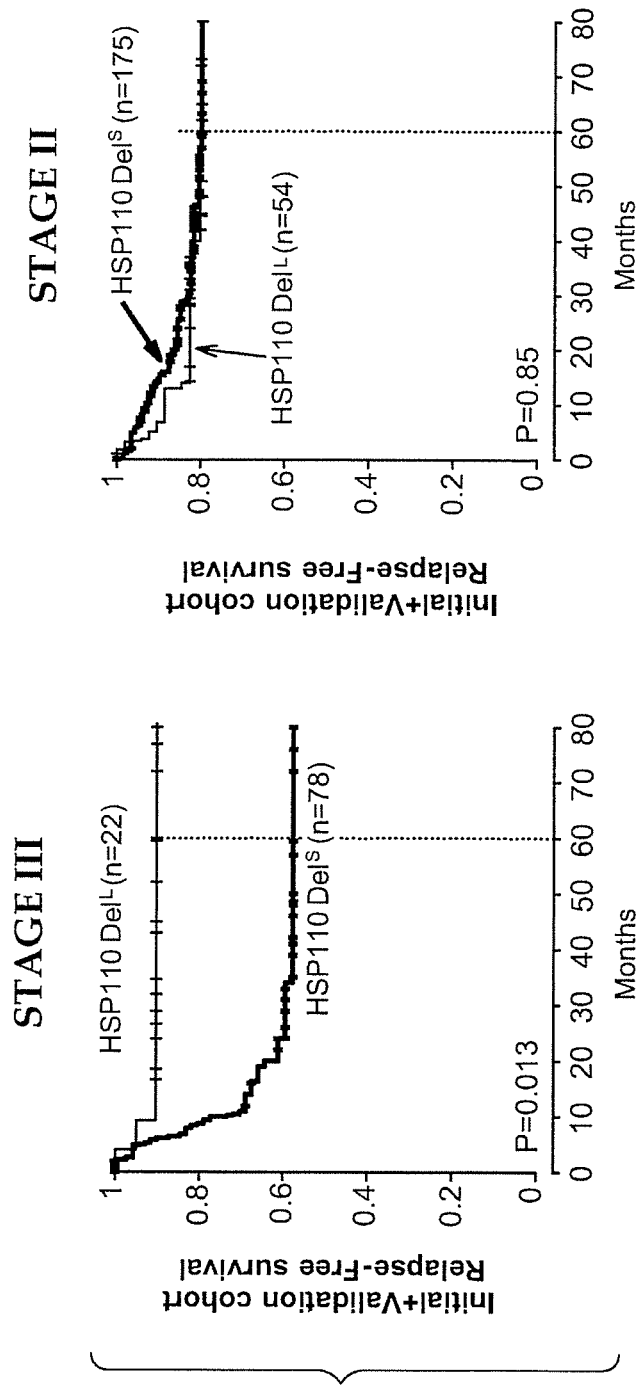
FIG. 20 depicts the survival analysis of stage II and stage III MSI CRC patients according to the size of deletions in the HSP110$T_{17}$ DNA repeat (overall cohort of patients). Patients are classified into two groups according to the size of deletion in the $T_{17}$ intronic repeat of HSP110 (ΔT≥5 bp, $T_{11}$, $T_{10}$, $T_9$ for MSI HSP110Del$^L$ patients; 0≤ΔT<5, $T_{17}$ to $T_{12}$ for MSI HSP110Del$^S$ patients).
Figure 21:
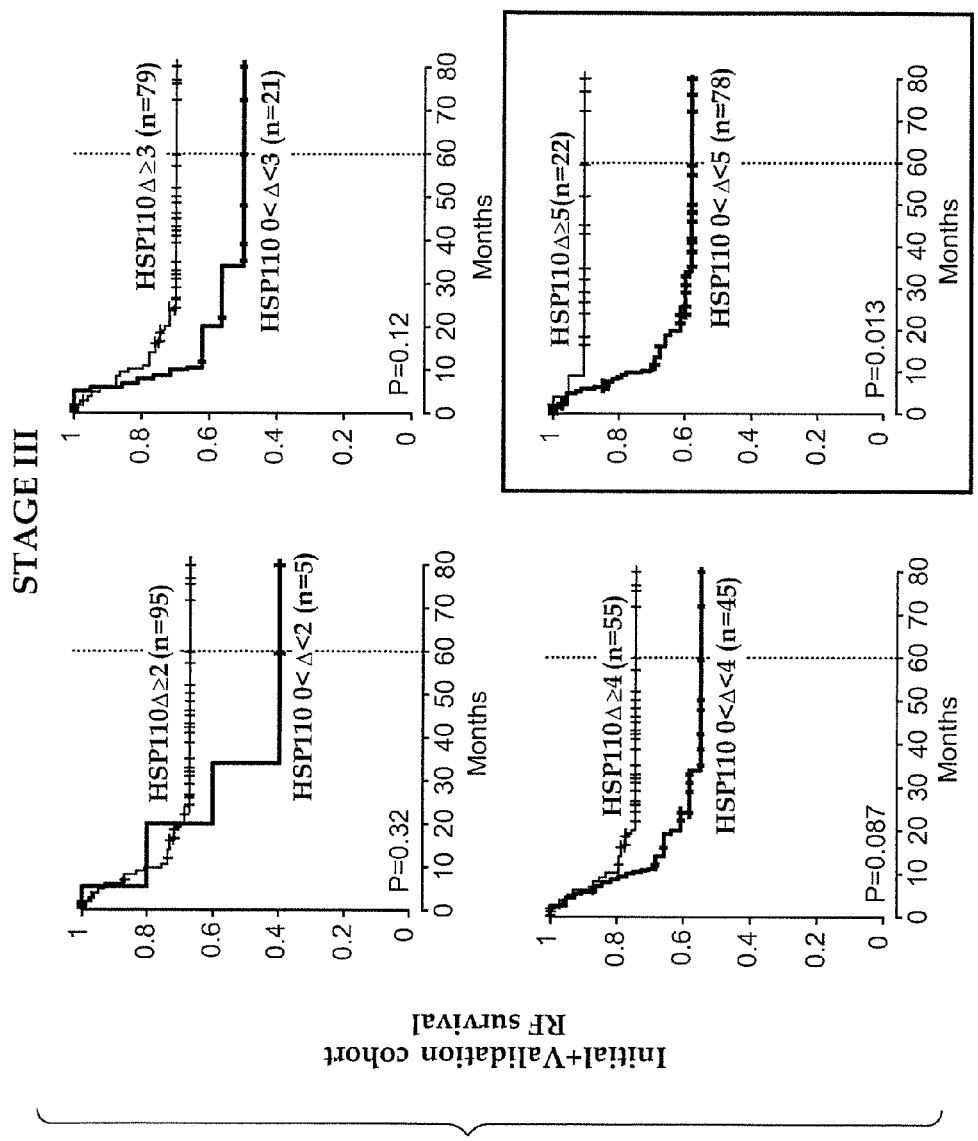
FIG. 21 depicts the survival analysis of MSI CRC patients according to the size of deletion in the HSP110 $T_{17}$ DNA repeat. In each survival analysis, patients are clustered in two groups according to the size of the $T_{17}$ deletion in tumor DNA (Top-left panel: ΔT≥2 bp, $T_{14}$ to $T_9$, i.e. MSI HSP110Del$^L$ CRC patients, 0≤ΔT<2, $T_{17}$ to $T_{15}$, i.e. MSI HSP110Del$^S$. Top-right panel: ΔT≥3 bp, $T_{13}$ to $T_9$, i.e. MSI HSP110Del$^L$ CRC patients, 0≤ΔT<3, T$_{17}$ to T$_{14}$, i.e. MSI HSP110Del$^S$. Bottom-left panel: ΔT≥4 bp, T$_{12}$ to T$_9$, i.e. MSI HSP110Del$^L$ CRC patients, 0≤ΔT<3, T$_{17}$ to T$_{13}$, i.e. MSI HSP110Del$^S$. Bottom-right panel: ΔT≥5 bp, T$_{11}$ to T$_9$, i.e. MSI HSP110Del$^L$ CRC patients, 0≤ΔT<5, T$_{17}$ to T$_{12}$, i.e. MSI HSP110Del$^S$.

The putative clinical relevance of HSP110 $T_{17}$ mutations in stage II and stage II MSI CRC was investigated. This was first examined in an initial cohort of 98 stage II or stage III tumors. Patients were clustered into two groups that displayed large deletions ($\Delta T \geq 5$ bp, comprising $T_{11}$, $T_{10}$, and $T_9$; HSP110Del$^L$) or small deletions ($0 \leq \Delta T < 5$, comprising $T_{17}$, $T_{16}$, $T_{15}$, $T_{14}$, $T_{13}$ and $T_{12}$; MSI HSP110Del$^S$). Although the number of stage III HSP110Del$^L$ cases was small (n=8), these patients showed excellent survival compared to HSP110Del$^S$ cases (P=0.065; FIG. 18). No such difference in survival was apparent for stage II cases (FIG. 18). Similar results were obtained in a multicentre validation cohort of 231 stage II or III MSI CRC patients (FIG. 19). When the two cohorts were combined, the difference in survival between stage III MSI HSP110Del$^L$ and HSP110Del$^S$ CRC patients reached significance (P=0.013; FIG. 20). The use of other cut-off points to classify the mutants ($\Delta T$=2, 3 or 4 bp) did not lead to significantly different survival groups (FIG. 21). In multivariate analysis, the HSP110 $T_{17}$ mutation status was significantly associated with relapse-free survival in stage II and III MSI CRC (Tables 8 to 13).

TABLE 8

Association of clinical and molecular annotations to outcome (relapse-free survival) in univariate Cox analysis on Stage II & III MSI CRC Patients.

| | | UNIVARIATE ANALYSIS | | | | | |
|---|---|---|---|---|---|---|---|
| Variable | Value | N | n | H.R. | 95% C.I. | P Value modality | P Value model |
| Tumor Stage (ref = II) | III | 329 | 70 | 2.1 | 1.3-3.3 | 0.0027 | 0.0022 |
| Age (ref = <75 y) | ≥ψ 57 | 329 | 70 | 1.7 | 1.1-2.8 | 0.024 | 0.022 |
| HNPCC (none) | HNPCC | 166 | 35 | 2.4 | 0.92-6.1 | 0.073 | 0.064 |
| Tumor Location (ref = LC) | RC | 324 | 68 | 1.9 | 0.96-3.9 | 0.064 | 0.13 |
| | RECTUM | 324 | 68 | 0.91 | 0.12-7.2 | 0.93 | |
| HSP110-Del (ref = small) | Large | 329 | 70 | 0.63 | 0.34-1.2 | 0.14 | 0.14 |
| Chemotherapy (ref = no) | yes | 329 | 70 | 1.2 | 0.74-2.1 | 0.41 | 0.41 |
| Chemo Type (ref = FOLFOX) | LV5FU2 | 72 | 17 | 1.4 | 0.51-4.1 | 0.49 | 0.49 |
| Gender (ref = F) | M | 329 | 70 | 0.86 | 0.53-1.4 | 0.56 | 0.56 |

CRC, colorectal cancer;

MSI, microsatellite instability;

y, years;

LC, left colon;

RC right colon;

F, female;

M, male;

RFS, relapse-free survival.

HNPCC and Chemotherapy type were not included in the multivariate model because of their smaller sample size.

TABLE 9

Association of clinical and molecular annotations to outcome (relapse-free survival) in multivariate Cox analysis on Stage II & III MSI CRC Patients.

| | | MULTIVARIATE ANALYSIS | | | | |
|---|---|---|---|---|---|---|
| Variable | Value | N | H.R. | 95% C.I. | P Value modality | P Value model |
| Tumor Stage (ref = II) | III | 324 | 2 | 1.1-3.5 | 0.015 | 0.0036 |
| Age (ref = <75 y) | ≥ψ 57 | 324 | 1.6 | 0.91-2.9 | 0.097 | |
| HNPCC (none) | HNPCC | | | | | |
| Tumor Location (ref = LC) | RC | 324 | 1.9 | 0.91-3.9 | 0.089 | |
| | RECTUM | 324 | 0.89 | 0.11-7.1 | 0.92 | |
| HSP110-Del (ref = small) | Large | 324 | 0.51 | 0.26-0.98 | 0.042 | |
| Chemo-therapy (ref = no) | yes | 324 | 0.51 | 0.63-2.4 | 0.54 | |
| Chemo Type (ref = FOLFOX) | LV5FU2 | | | | | |
| Gender (ref = F) | M | 324 | 1 | 0.61-1.7 | 0.97 | |

CRC, colorectal cancer;
MSI, microsatellite instability;
y, years;
LC, left colon;
RC right colon;
F, female;
M, male;
RFS, relapse-free survival.
HNPCC and Chemotherapy type were not included in the multivariate model because of their smaller sample size.

TABLE 10

Univariate analysis in Stage III MSI-CRC Patients.

| | | UNIVARIATE ANALYSIS | | | | | |
|---|---|---|---|---|---|---|---|
| Annotation | Value | N | n. event | H.R. | 95% C.I. | P value modality | P value model |
| HSP110 Del (ref = small) | Large | 100 | 31 | 0.2 | 0.047-0.83 | 0.026 | 0.013 |
| Gender (ref = F) | M | 100 | 31 | 0.58 | 0.26-1.3 | 0.19 | 0.18 |
| Chemotherapy (ref = no) | yes | 100 | 31 | 0.71 | 0.35-1.4 | 0.35 | 0.34 |
| HNPCC (none) | HNPCC | 45 | 14 | 0.51 | 0.12-2.3 | 0.38 | 0.38 |
| Age (ref = <75 y) | ≥75 y | 100 | 31 | 1.2 | 0.59-2.4 | 0.63 | 0.63 |
| Chemotherapy Type (ref = FOLFOX) | LV5FU2 | 48 | 13 | 1.3 | 0.38-4.2 | 0.7 | 0.70 |
| Tumor Location (ref = Left Colon) | Right Colon | 97 | 30 | 1.3 | 0.53-3.2 | 0.56 | 0.84 |
| | Rectum | 97 | | 1.3 | 0.16-11 | 0.81 | |

TABLE 11

Multivariate analysis in Stage III MSI-CRC Patients.

| | | MULTIVARIATE ANALYSIS | | | | |
|---|---|---|---|---|---|---|
| Annotation | Value | N | H.R. | 95% C.I. | P value modality | P value model |
| HSP110 Del (ref = small) | Large | 97 | 0.17 | 0.04-0.73 | 0.018 | 0.11 |
| Gender (ref = F) | M | 97 | 0.52 | 0.21-1.3 | 0.15 | |
| Chemotherapy (ref = no) | yes | 97 | 0.76 | 0.26-2.3 | 0.63 | |
| HNPCC (none) | HNPCC | | | | | |
| Age (ref = <75 y) | ≥75 y | 97 | 0.78 | 0.26-2.3 | 0.65 | |
| Chemotherapy Type (ref = FOLFOX) | LV5FU2 | | | | | |
| Tumor Location (ref = Left Colon) | Right Colon | 97 | 1.4 | 0.54-3.6 | 0.48 | |
| | Rectum | 97 | 1.6 | 0.18-15 | 0.66 | |

TABLE 12

Univariate analysis in MSI CRC Patients under chemotherapy.

UNIVARIATE ANALYSIS

| Annotation | Value | N | n. event | H.R. | 95% C.I. | P value modality | P value model |
|---|---|---|---|---|---|---|---|
| HSP110 Del (ref = small) | Large | 77 | 20 | 0.14 | 0.019-1.1 | 0.057 | 0.026 |
| Tumor Stage (ref = 2) | III | 77 | 20 | 1.7 | 0.6-4.6 | 0.33 | 0.32 |
| Chemotherapy Type (ref = FOLFOX) | LV5FU2 | 72 | 17 | 1.4 | 0.51-4.1 | 0.49 | 0.49 |
| Tumor Location (ref = Left Colon) | Right Colon | 77 | 20 | 2 | 0.6-7 | 0.26 | 0.51 |
|  | Rectum | 77 | 20 | 1.6 | 0.17-16 | 0.67 | 0.51 |
| HNPCC (none) | HNPCC | 27 | 6 | 1.5 | 0.31-76 | 0.6 | 0.60 |
| Gender (ref = F) | M | 77 | 20 | 0.82 | 0.33-2 | 0.66 | 0.66 |
| Age (ref = <75 y) | ≥75 y | 77 | 20 | 1.2 | 0.34-4 | 0.81 | 0.81 |

TABLE 13

Multivariate analysis in MSI CRC Patients under chemotherapy.

MULTIVARIATE ANALYSIS

| Annotation | Value | N | H.R. | 95% C.I. | P value modality | P value model |
|---|---|---|---|---|---|---|
| HSP110 Del (ref = small) | Large | 72 | 0.099 | 0.012-0.78 | 0.028 | 0.19 |
| Gender (ref = F) | M | 72 | 2 | 0.62-6.3 | 0.25 |  |
| Chemotherapy (ref = no) | yes | 72 | 1.3 | 0.43-3.7 | 0.67 |  |
| HNPCC (none) | HNPCC | 72 | 2.4 | 0.66-9 | 0.18 |  |
| Age (ref = <75 y) | ≥75 y | 72 | 1.6 | 0.15-16 | 0.7 |  |
| Chemotherapy Type (ref = FOLFOX) | LV5FU2 |  |  |  |  |  |
| Tumor Location (ref = Left Colon) | Right Colon | 72 | 0.73 | 0.25-2.1 | 0.55 |  |
|  | Rectum | 72 | 1 | 0.22-4.9 | 0.98 |  |

Amongst the clinical parameters, the only positive association observed was between HSP110Del$^L$ and proximal tumor location (P=0.027; Tables 14 and 15).

TABLE 14

Association of clinical annotations to HSP110 deletion status in stage II and III MSI CRC Patients.

Stage II & III MSI CRC Patients

| Annotation | Modality | N | n | P value | HSP110 Del$^S$ | HSP110 Del$^L$ |
|---|---|---|---|---|---|---|
| Tumor Stage | II | 329 | 229 | 0.89 | 175 (69%) | 54 (71%) |
|  | III |  | 100 |  | 78 (31%) | 22 (29%) |
| Tumor Localization | LC | 324 | 70 | 0.027* | 60 (24%) | 10 (13%) |
|  | RC |  | 246 |  | 181 (73%) | 65 (87%) |
|  | Rectum |  | 8 |  | 8 (3%) | 0 (0%) |
| Gender | F | 329 | 197 | 0.59 | 149 (59%) | 48 (63%) |
|  | M |  | 132 |  | 104 (41%) | 28 (37%) |
| Age at diagnosis | NA | 329 | 329 | 0.14 | 74 | 77.5 |
| RFS event | 0 | 329 | 258 | 0.2 | 194 (77%) | 64 (84%) |
|  | 1 |  | 71 |  | 59 (23%) | 12 (16%) |
| Chemo performed | N | 329 | 252 | 1 | 194 (77%) | 58 (76%) |
|  | Y |  | 77 |  | 59 (23%) | 18 (24%) |
| Chemo | LV5FU2 | 318 | 42 | 0.94 | 31 (13%) | 11 (15%) |
| Type | FOLFOX |  | 30 |  | 23 (9%) | 7 (9%) |
|  | FUFOL |  | 2 |  | 2 (1%) | 0 (0%) |
|  | None |  | 244 |  | 188 (77%) | 56 (76%) |
| HNPCC | HNPCC | 166 | 44 | 1 | 32 (26%) | 12 (27%) |
|  | None |  | 122 |  | 89 (74%) | 33 (73%) |
| HNPCC inferred | HNPCC | 329 | 63 | 1 | 49 (19%) | 14 (18%) |
|  | None |  | 266 |  | 204 (81%) | 62 (82%) |
| TOTAL |  | 329 | — | — | 253 (77%) | 76 (23%) |

CRC, colorectal cancer;
MSI, microsatellite instability;
LC, left colon;
RC right colon;
F, female;
M, male;
RFS, relapse-free survival.
N: total number of patients with the annotation;
n = number of patients for the given modality;
HNPCC inferred, young patients (<50 years) with MSI CRC.
P value: Fisher exact test P value.
*P value without Rectum are 0.039 and 0.088 in stage 2&3 patients and in stage 3 patients, respectively.

TABLE 15

Association of clinical annotations to HSP110 deletion status in stage III MSI CRC Patients.

Stage III MSI CRC Patients

| Annotation | Modality | N | n | P value | HSP110 Del$^S$ | HSP110 Del$^L$ |
|---|---|---|---|---|---|---|
| Tumor Stage | II |  |  |  |  |  |
|  | III | 329 | 100 | 0.89 | 78 (100%) | 22 (100%) |
| Tumor Localization | LC | 97 | 22 | 0.15* | 20 (27%) | 2 (9%) |
|  | RC |  | 72 |  | 52 (69%) | 20 (91%) |
|  | Rectum |  | 3 |  | 3 (4%) | 0 (0%) |
| Gender | F | 100 | 64 | 0.21 | 47 (60%) | 17 (77%) |
|  | M |  | 36 |  | 31 (40%) | 5 (23%) |
| Age at diagnosis | NA | 100 | 100 | 0.54 | 75.15 | 75.5 |
| RFS event | 0 | 100 | 69 | 0.017 | 49 (63%) | 20 (91%) |
|  | 1 |  | 31 |  | 29 (37%) | 2 (9%) |
| Chemo performed | N | 100 | 49 | 0.23 | 41 (53%) | 8 (36%) |
|  | Y |  | 51 |  | 37 (47%) | 14 (64%) |

TABLE 15-continued

Association of clinical annotations to HSP110 deletion status in stage III MSI CRC Patients.

| Anno-tation | Modality | Stage III MSI CRC Patients | | | | |
|---|---|---|---|---|---|---|
| | | N | n | P value | HSP110 Del$^S$ | HSP110 Del$^L$ |
| Chemo Type | LV5FU2 | 96 | 28 | 0.49 | 20 (27%) | 8 (36%) |
| | FOLFOX | | 20 | | 14 (19%) | 6 (27%) |
| | FUFOL | | 1 | | 1 (1%) | 0 (0%) |
| | None | | 47 | | 39 (53%) | 8 (36%) |
| HNPCC | HNPCC | 45 | 10 | 1 | 8 (23%) | 2 (20%) |
| | None | | 35 | | 27 (77%) | 8 (80%) |
| HNPCC inferred | HNPCC | 100 | 18 | 0.76 | 15 (19%) | 3 (14%) |
| | None | | 82 | | 63 (81%) | 19 (86%) |
| | TOTAL | 100 | — | — | 78 (78%) | 22 (22%) |

CRC, colorectal cancer;
MSI, microsatellite instability;
LC, left colon;
RC right colon;
F, female;
M, male;
RFS, relapse-free survival.
N: total number of patients with the annotation;
n = number of patients for the given modality;
HNPCC inferred, young patients (<50 years) with MSI CRC.
P value: Fisher exact test P value.
*P value without Rectum are 0.039 and 0.088 in stage 2&3 patients and in stage 3 patients, respectively.

Figure 22:
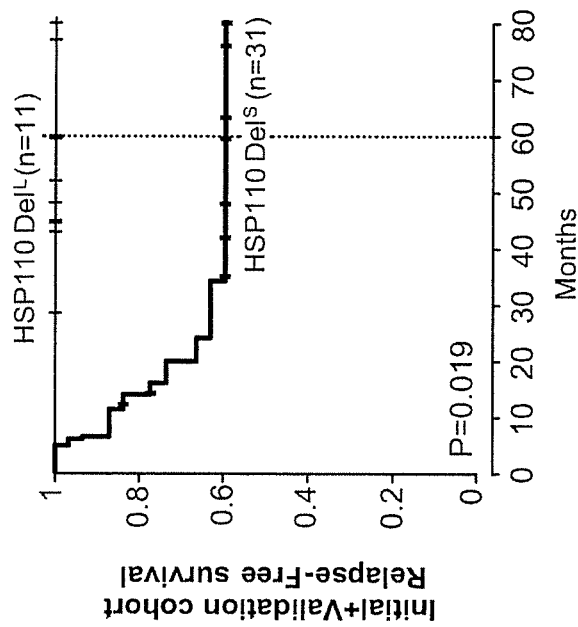
FIG. 22 depicts the survival analysis of stage II and stage III MSI CRC patients treated with chemotherapy according to the size of deletions in the HSP110 T$_{17}$ DNA repeat. Patients are classified into two groups according to the size of deletion in the T$_{17}$ intronic repeat of HSP110 (ΔT≥5 bp, T$_{11}$, T$_{10}$, T$_9$ for MSI HSP110Del$^L$ patients; 0≤ΔT<5, T$_{17}$ to T$_{12}$ for MSI HSP110Del$^S$ patients).
Figure 23:
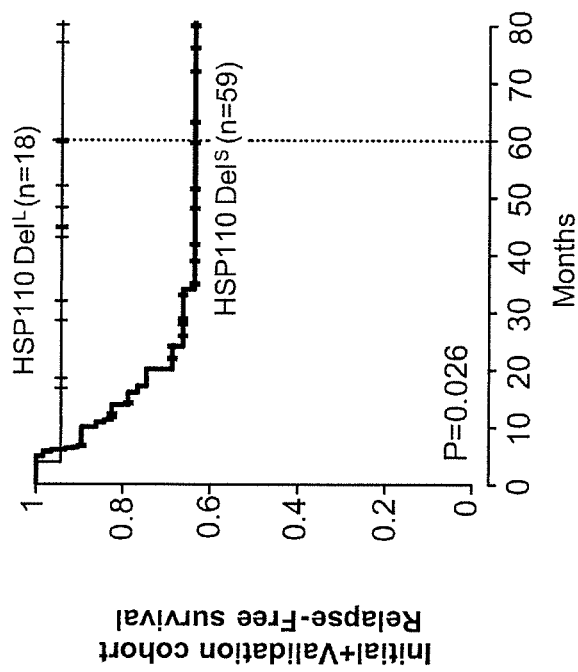
FIG. 23 depicts the survival analysis of stage II and stage III MSI CRC patients treated with 5-fluorouracil according to the size of deletions in the HSP110 T$_{17}$ DNA repeat. Patients are classified into two groups according to the size of deletion in the T$_{17}$ intronic repeat of HSP110 (ΔT≥5 bp, T$_{11}$, T$_{10}$, T$_9$ for MSI HSP110Del$^L$ patients; 0≤ΔT<5, T$_{17}$ to T$_{12}$ for MSI HSP110Del$^S$ patients).

HSP110 $T_{17}$ Mutation Status and the Survival of 5-fluorouracil-treated MSI CRC Patients It has been shown that the HSP110DE9 mutant chaperone caused the sensitization of colon cancer cells to chemotherapeutic agents including 5-fluorouracil and oxaliplatin in vitro. In the present study the relapse-free survival of CRC patients treated with 5-fluorouracil-based adjuvant chemotherapy in relation to their HSP110 $T_{17}$ mutation status was examined. In the overall cohort of patients, MSI HSP110Del$^L$ CRC subjects who received adjuvant chemotherapy showed significantly better relapse-free survival compared to HSP110Del$^S$ patients (P=0.026; FIG. 22). MSI HSP110Del$^L$ CRC subjects displayed excellent survival, regardless of the adjuvant chemotherapy regimen used. Since MSI CRC patients have been reported not to benefit from adjuvant chemotherapy with 5-fluorouracil alone, HSP110 $T_{17}$ mutation status in this particular group of MSI CRC patients was next investigated. Patients with MSI HSP110Del$^L$ CRC displayed excellent survival compared to MSI HSP110Del$^S$ patients (FIG. 23). Multivariate models confirmed that the survival of chemotherapy-treated MSI CRC patients was dependent on the mutation status of HSP110 $T_{17}$ (Tables 10 to 15).

Discussion

The results from analysis of a large, consecutive, multicentre and retrospective series of 365 MSI CRC patients are presented herein. Deletions within the HSP110 $T_{17}$ microsatellite were determined using the sensitive, established and highly reproducible PCR-fluorescence genotyping method (Buhard et al., *J Clin Oncol*, 24:241-251, (2006)). Using this approach, and further classifying MSI CRC according to size of the HSP110 $T_{17}$ deletion, two groups of stage III patients with very different relapse-free survival rates were observed. Patients with large deletions (HSP110Del$^L$; ΔT=5-7 bp) and accounting for approximately 20% of all stage III MSI CRC showed excellent prognosis, with only 2/22 (9%) relapsing after 5 years compared to over 40% of HSP110Del$^S$ patients (ΔT=0-4 bp). Thus, overall these data indicate that large deletions in the $T_{17}$ repeat of HSP110 are prognostic for improved survival of stage III MSI CRC patients. The use of other cut-off points to classify the mutants did not lead to significantly different survival groups. However, the closer the cut-off point between small and large deletions gets to 5, the more significant the difference is in terms of relapse-free survival in stage III CRC. In any case, 5 is the only cut-off value that permits the identification of a relapse-free group of stage III MSI CRC patients.

Another important question is whether the mutation status of HSP110 $T_{17}$ provides a mechanistic link for the different survival observed for stage III MSI HSP110Del$^L$ and HSP110Del$^S$ patients. Patients with stage II and stage III MSI HSP110Del$^L$ tumors showed excellent survival, regardless of whether the adjuvant chemotherapy they received was 5-fluorouracil alone or in combination with other drugs. Hence, the determination of HSP110 $T_{17}$ status may be a valuable predictive marker for MSI CRC patients who will benefit from adjuvant chemotherapy. It is worth noting that MSI HSP110Del$^L$ CRC patients displayed excellent survival when treated with 5-fluorouracil alone and that the difference in survival remained significant when compared to MSI HSP110Del$^S$ CRC subjects. Importantly, there was no association between HSP110 mutation status and patients' age or HNPCC status that was recently suggested as a criteria influencing response to this anticancer agent in MSI CRC. These findings may have important clinical implications for the use of adjuvant therapy in CRC patients. If confirmed by additional analyses of well characterized patient cohorts or by prospective, randomized, controlled studies, they would indicate the HSP110 $T_{17}$ mutational status could be used to direct rational adjuvant chemotherapy in MSI CRC. In the present cohort, MSI HSP110Del$^L$ CRC patients displayed excellent survival when treated with FOLFOX but the difference in survival did not reached significance when compared to MSI HSP110Del$^S$ CRC subjects.

The above findings provide evidence for an additional layer of clinical heterogeneity amongst MSI colon cancers related to HSP110 mutational status. The survival of MSI HSP110Del$^S$ and HSP110Del$^L$ CRC patient was therefore compared to that of an age, gender, tumor site and stage matched cohort of 282 MSS patients. The survival of MSI HSP110Del$^L$ patients was significantly better than that of MSS HSP110$^S$ patients in both stage III and adjuvant treated patient groups. No survival difference was observed between the MSS HSP110$^{WT}$ and MSI HSP110Del$^S$ patient groups. For patients treated with 5-fluorouracil as the sole chemotherapeutic agent, no significant difference between the survival of MSI and MSS groups was observed. However, MSI HSP110Del$^S$ patients displayed similar survival to MSS HSP110$^{WT}$ cases treated with 5-fluorouracil, whereas the survival of MSI HSP110Del$^L$ patients was significantly better. In multivariate models including MSI and MSS CRC patients, the HSP110 $T_{17}$ mutation status was significantly associated with relapse-free survival in CRC patients (Table 4). These last results suggest that the HSP110 $T_{17}$ mutational status may be superior to MSI as a predictive biomarker. They highlight the issue of clinical heterogeneity in CRC and, if confirmed by prospective studies, should lead to reconsideration of the clinical behavior of MSI and MSS colorectal tumors more generally.

The data presented here indicate that genotypic analysis of the $T_{17}$ repeat of HSP110 provides new insights into the clinical characteristics of MSI CRC. This simple method can be used to determine the HSP110 mutation status of both fresh or paraffin-embedded tumor DNA samples. It could thus be recommended routinely together with investigation of the microsatellite-instability phenotype in prospective, randomized, controlled studies, to confirm that mutational status of the HSP110 $T_{17}$ in colon tumors could be used to help clinicians in selecting subsets of patients who would most likely benefit from cytotoxic adjuvant chemotherapy.

The invention claimed is:

1. A therapeutic method for improving the condition of a subject suffering from a malignant tumor which expresses the protein of SEQ ID NO. 1, wherein said method comprises the steps of:
   a) determining in vitro a length of thymidine repetition of a microsatellite repeat of 17 thymidine nucleotides localized in the splicing acceptor site of intron 8 of the gene encoding heat-shock protein 110 (HSP110) in a tumor sample of said patient obtained from the malignant tumor which expresses the protein of SEQ ID NO. 1, and
   b) administering chemotherapy to the subject who has been determined to have a deletion of at least 8 thymidines of said thymidine repetition.

2. The method of claim 1, wherein the subject has a tumor type selected from the group consisting of colorectal cancer, stomach cancer, endometrial cancer, bladder cancer, urinary tract cancer, ovary cancer, prostate cancer, lymphomas, leukemias, glioblastoma, astrocytoma and neuroblastoma.

* * * * *

```
                         SEQUENCE LISTING

<160> NUMBER OF SEQ ID NOS: 23

<210> SEQ ID NO 1
<211> LENGTH: 380
<212> TYPE: PRT
<213> ORGANISM: Homo sapiens

<400> SEQUENCE: 1

Met Ser Val Val Gly Leu Asp Val Gly Ser Gln Ser Cys Tyr Ile Ala
1               5                   10                  15

Val Ala Arg Ala Gly Gly Ile Glu Thr Ile Ala Asn Glu Phe Ser Asp
            20                  25                  30

Arg Cys Thr Pro Ser Val Ile Ser Phe Gly Ser Lys Asn Arg Thr Ile
        35                  40                  45

Gly Val Ala Ala Lys Asn Gln Gln Ile Thr His Ala Asn Asn Thr Val
    50                  55                  60

Ser Asn Phe Lys Arg Phe His Gly Arg Ala Phe Asn Asp Pro Phe Ile
65                  70                  75                  80

Gln Lys Glu Lys Glu Asn Leu Ser Tyr Asp Leu Val Pro Leu Lys Asn
                85                  90                  95

Gly Gly Val Gly Ile Lys Val Met Tyr Met Gly Glu Glu His Leu Phe
            100                 105                 110

Ser Val Glu Gln Ile Thr Ala Met Leu Leu Thr Lys Leu Lys Glu Thr
        115                 120                 125

Ala Glu Asn Ser Leu Lys Lys Pro Val Thr Asp Cys Val Ile Ser Val
    130                 135                 140

Pro Ser Phe Phe Thr Asp Ala Glu Arg Arg Ser Val Leu Asp Ala Ala
145                 150                 155                 160

Gln Ile Val Gly Leu Asn Cys Leu Arg Leu Met Asn Asp Met Thr Ala
                165                 170                 175

Val Ala Leu Asn Tyr Gly Ile Tyr Lys Gln Asp Leu Pro Ser Leu Asp
            180                 185                 190

Glu Lys Pro Arg Ile Val Val Phe Val Asp Met Gly His Ser Ala Phe
        195                 200                 205

Gln Val Ser Ala Cys Ala Phe Asn Lys Gly Lys Leu Lys Val Leu Gly
    210                 215                 220

Thr Ala Phe Asp Pro Phe Leu Gly Gly Lys Asn Phe Asp Glu Lys Leu
225                 230                 235                 240

Val Glu His Phe Cys Ala Glu Phe Lys Thr Lys Tyr Lys Leu Asp Ala
                245                 250                 255

Lys Ser Lys Ile Arg Ala Leu Leu Arg Leu Tyr Gln Glu Cys Glu Lys
            260                 265                 270

Leu Lys Lys Leu Met Ser Ser Asn Ser Thr Asp Leu Pro Leu Asn Ile
        275                 280                 285

Glu Cys Phe Met Asn Asp Lys Asp Val Ser Gly Lys Met Asn Arg Ser
    290                 295                 300

Gln Phe Glu Glu Leu Cys Ala Glu Leu Leu Gln Lys Ile Glu Val Pro
305                 310                 315                 320

Leu Tyr Ser Leu Leu Glu Gln Thr His Leu Lys Val Glu Asp Val Ser
                325                 330                 335

Ala Val Glu Ile Val Gly Gly Ala Thr Arg Ile Pro Ala Val Lys Glu
            340                 345                 350
```

Arg Ile Ala Lys Phe Phe Gly Lys Asp Ile Ser Thr Thr Leu Asn Ala
            355                 360                 365

Asp Glu Ala Val Ala Arg Gly Cys Ala Leu Gln Cys
        370                 375                 380

<210> SEQ ID NO 2
<211> LENGTH: 858
<212> TYPE: PRT
<213> ORGANISM: Homo sapiens

<400> SEQUENCE: 2

Met Ser Val Val Gly Leu Asp Val Gly Ser Gln Ser Cys Tyr Ile Ala
1               5                   10                  15

Val Ala Arg Ala Gly Gly Ile Glu Thr Ile Ala Asn Glu Phe Ser Asp
            20                  25                  30

Arg Cys Thr Pro Ser Val Ile Ser Phe Gly Ser Lys Asn Arg Thr Ile
        35                  40                  45

Gly Val Ala Ala Lys Asn Gln Gln Ile Thr His Ala Asn Asn Thr Val
    50                  55                  60

Ser Asn Phe Lys Arg Phe His Gly Arg Ala Phe Asn Asp Pro Phe Ile
65                  70                  75                  80

Gln Lys Glu Lys Glu Asn Leu Ser Tyr Asp Leu Val Pro Leu Lys Asn
                85                  90                  95

Gly Gly Val Gly Ile Lys Val Met Tyr Met Gly Glu Glu His Leu Phe
            100                 105                 110

Ser Val Glu Gln Ile Thr Ala Met Leu Leu Thr Lys Leu Lys Glu Thr
        115                 120                 125

Ala Glu Asn Ser Leu Lys Lys Pro Val Thr Asp Cys Val Ile Ser Val
    130                 135                 140

Pro Ser Phe Phe Thr Asp Ala Glu Arg Arg Ser Val Leu Asp Ala Ala
145                 150                 155                 160

Gln Ile Val Gly Leu Asn Cys Leu Arg Leu Met Asn Asp Met Thr Ala
                165                 170                 175

Val Ala Leu Asn Tyr Gly Ile Tyr Lys Gln Asp Leu Pro Ser Leu Asp
            180                 185                 190

Glu Lys Pro Arg Ile Val Val Phe Val Asp Met Gly His Ser Ala Phe
        195                 200                 205

Gln Val Ser Ala Cys Ala Phe Asn Lys Gly Lys Leu Lys Val Leu Gly
    210                 215                 220

Thr Ala Phe Asp Pro Phe Leu Gly Gly Lys Asn Phe Asp Glu Lys Leu
225                 230                 235                 240

Val Glu His Phe Cys Ala Glu Phe Lys Thr Lys Tyr Lys Leu Asp Ala
                245                 250                 255

Lys Ser Lys Ile Arg Ala Leu Leu Arg Leu Tyr Gln Glu Cys Glu Lys
            260                 265                 270

Leu Lys Lys Leu Met Ser Ser Asn Ser Thr Asp Leu Pro Leu Asn Ile
        275                 280                 285

Glu Cys Phe Met Asn Asp Lys Asp Val Ser Gly Lys Met Asn Arg Ser
    290                 295                 300

Gln Phe Glu Glu Leu Cys Ala Glu Leu Leu Gln Lys Ile Glu Val Pro
305                 310                 315                 320

Leu Tyr Ser Leu Leu Glu Gln Thr His Leu Lys Val Glu Asp Val Ser
                325                 330                 335

Ala Val Glu Ile Val Gly Gly Ala Thr Arg Ile Pro Ala Val Lys Glu
            340                 345                 350

```
Arg Ile Ala Lys Phe Phe Gly Lys Asp Ile Ser Thr Thr Leu Asn Ala
        355                 360                 365

Asp Glu Ala Val Ala Arg Gly Cys Ala Leu Gln Cys Ala Ile Leu Ser
    370                 375                 380

Pro Ala Phe Lys Val Arg Glu Phe Ser Val Thr Asp Ala Val Pro Phe
385                 390                 395                 400

Pro Ile Ser Leu Ile Trp Asn His Asp Ser Glu Asp Thr Glu Gly Val
                405                 410                 415

His Glu Val Phe Ser Arg Asn His Ala Ala Pro Phe Ser Lys Val Leu
            420                 425                 430

Thr Phe Leu Arg Arg Gly Pro Phe Glu Leu Glu Ala Phe Tyr Ser Asp
        435                 440                 445

Pro Gln Gly Val Pro Tyr Pro Glu Ala Lys Ile Gly Arg Phe Val Val
    450                 455                 460

Gln Asn Val Ser Ala Gln Lys Asp Gly Glu Lys Ser Arg Val Lys Val
465                 470                 475                 480

Lys Val Arg Val Asn Thr His Gly Ile Phe Thr Ile Ser Thr Ala Ser
                485                 490                 495

Met Val Glu Lys Val Pro Thr Glu Glu Asn Glu Met Ser Ser Glu Ala
            500                 505                 510

Asp Met Glu Cys Leu Asn Gln Arg Pro Pro Glu Asn Pro Asp Thr Asp
        515                 520                 525

Lys Asn Val Gln Gln Asp Asn Ser Glu Ala Gly Thr Gln Pro Gln Val
    530                 535                 540

Gln Thr Asp Ala Gln Gln Thr Ser Gln Ser Pro Ser Pro Glu Leu
545                 550                 555                 560

Thr Ser Glu Glu Asn Lys Ile Pro Asp Ala Asp Lys Ala Asn Glu Lys
                565                 570                 575

Lys Val Asp Gln Pro Pro Glu Ala Lys Lys Pro Lys Ile Lys Val Val
            580                 585                 590

Asn Val Glu Leu Pro Ile Glu Ala Asn Leu Val Trp Gln Leu Gly Lys
        595                 600                 605

Asp Leu Leu Asn Met Tyr Ile Glu Thr Glu Gly Lys Met Ile Met Gln
    610                 615                 620

Asp Lys Leu Glu Lys Glu Arg Asn Asp Ala Lys Asn Ala Val Glu Glu
625                 630                 635                 640

Tyr Val Tyr Glu Phe Arg Asp Lys Leu Cys Gly Pro Tyr Glu Lys Phe
                645                 650                 655

Ile Cys Glu Gln Asp His Gln Asn Phe Leu Arg Leu Leu Thr Glu Thr
            660                 665                 670

Glu Asp Trp Leu Tyr Glu Glu Gly Glu Asp Gln Ala Lys Gln Ala Tyr
        675                 680                 685

Val Asp Lys Leu Glu Glu Leu Met Lys Ile Gly Thr Pro Val Lys Val
    690                 695                 700

Arg Phe Gln Glu Ala Glu Glu Arg Pro Lys Met Phe Glu Glu Leu Gly
705                 710                 715                 720

Gln Arg Leu Gln His Tyr Ala Lys Ile Ala Ala Asp Phe Arg Asn Lys
                725                 730                 735

Asp Glu Lys Tyr Asn His Ile Asp Glu Ser Glu Met Lys Lys Val Glu
            740                 745                 750

Lys Ser Val Asn Glu Val Met Glu Trp Met Asn Asn Val Met Asn Ala
        755                 760                 765
```

Gln Ala Lys Lys Ser Leu Asp Gln Asp Pro Val Val Arg Ala Gln Glu
    770                 775                 780
Ile Lys Thr Lys Ile Lys Glu Leu Asn Asn Thr Cys Glu Pro Val Val
785                 790                 795                 800
Thr Gln Pro Lys Pro Lys Ile Glu Ser Pro Lys Leu Glu Arg Thr Pro
                805                 810                 815
Asn Gly Pro Asn Ile Asp Lys Lys Glu Glu Asp Leu Glu Asp Lys Asn
            820                 825                 830
Asn Phe Gly Ala Glu Pro Pro His Gln Asn Gly Glu Cys Tyr Pro Asn
        835                 840                 845
Glu Lys Asn Ser Val Asn Met Asp Leu Asp
    850                 855

<210> SEQ ID NO 3
<211> LENGTH: 3573
<212> TYPE: DNA
<213> ORGANISM: Homo sapiens

<400> SEQUENCE: 3
tgagtaaatg ccgcagattc tggaaagttc tgatcagtgc gatacataag gctgaggaag     60
tgggacctcc ccttttgggt cggtagttca gcgccggcgc cggtgtgcga gccgcggcag    120
agtgaggcag gcaacccgag gtgcggagcg acctgcggag gctgagcccc gctttctccc    180
agggtttctt atcagccagc cgccgctgtc cccggggggga taggaggctc ctgacaggcc    240
gcggctgtct gtgtgtcctt ctgagtgtca gaggaacggc cagacccgc gggccggagc    300 agaacgcggc cagggcagaa agcggcggca ggagaagcag gcaggggcc ggaggacgca    360 gaccgagacc cgaggcggag gcggaccgcg agccggccat gtcggtggtg gggttggacg    420
tgggctcgca gagctgctac atcgcggtag ccccgggccgg gggcatcgag accatcgcca    480
atgagttcag cgaccggtgc accccgtcag tcatatcatt tggatcaaaa aatagaacaa    540
tcggagttgc agccaaaaat cagcaaatca ctcatgcaaa caatacgtg tctaacttca    600 aaagatttca tggccgagca ttcaatgacc ccttcattca aaaggagaag gaaaacttga    660
gttacgattt ggttccattg aaaaatggtg gagttggaat aaaggtaatg tacatggtg    720 aagaacatct atttagtgtg gagcagataa cagccatgtt gttgactaag ctgaaggaaa    780
ctgctgaaaa cagcctcaag aaaccagtaa cagattgtgt tatttcagtc ccctccttct    840
ttacagatgc tgagaggcga tctgtgttag atgctgcaca gattgttggc ctaaactgtt    900
taagacttat gaatgacatg acagctgttg ctttgaatta cggaatttat aagcaggatc    960
tcccaagcct ggatgagaaa cctcggatag tggttttgt tgatatggga cattcagctt   1020
ttcaagtgtc tgcttgtgct tttaacaagg gaaaattgaa ggtactggga acagcttttg   1080 atccttttctt aggaggaaaa aacttcgatg aaaagttagt ggaacatttt tgtgcagaat   1140
ttaaaactaa gtacaagttg gatgcaaaat ccaaaatacg agcactccta cgtctgtatc   1200
aggaatgtga aaaactgaaa aagctaatga gctctaacag cacagacctt ccactgaata   1260
tcgaatgctt tatgaatgat aaagatgttt ccggaaagat gaacaggtca caatttgaag   1320
aactctgtgc tgaacttctg caaaagatag aagtaccct ttattcactg ttggaacaaa   1380
ctcatctcaa agtagaagat gtgagtgcag ttgagattgt tggaggcgct acacgaattc   1440
cagctgtgaa ggaaagaatt gccaaattct ttggaaaaga tattagcaca acactcaatg   1500
cagatgaagc agtagccaga ggatgtgcat tacagtgttc atgaagtctt tagtcgaaac   1560
catgctgctc ctttctccaa agttctcacc tttctgagaa gggggccttt tgagctagaa   1620

```
gctttctatt ctgatcccca aggagttcca tatccagaag caaaatagg ccgctttgta    1680 gttcagaatg tttctgcaca gaaagatgga gaaaaatcta gagtaaaagt caaagtgcga    1740
gtcaacaccc atggcatttt caccatctct acggcatcta tggtggagaa agtcccaact    1800
gaggagaatg aaatgtcttc tgaagctgac atggagtgtc tgaatcagag accaccagaa    1860
aacccagaca ctgataaaaa tgtccagcaa gacaacagtg aagctggaac acagccccag    1920
gtacaaactg atgctcaaca aacctcacag tctccccctt cacctgaact tacctcagaa    1980
gaaaacaaaa tcccagatgc tgacaaagca aatgaaaaaa agttgaccca gcctccagaa    2040
gctaaaaagc ccaaaataaa ggtggtgaat gttgagctgc ctattgaagc caacttggtc    2100
tggcagttag ggaaagacct tcttaacatg tatattgaga cagagggtaa gatgataatg    2160
caagataaat tggaaaaaga aaggaatgat gctaaaaatg cagttgagga atatgtgtat    2220
gagttcagag acaagctgtg tggaccatat gaaaaattta tatgtgagca ggatcatcaa    2280 aatttttga gactcctcac agaaactgaa gactggctgt atgaagaagg agaggaccaa    2340
gctaaacaag catatgttga caagttggaa gaattaatga aaattggcac tccagttaaa    2400
gttcggtttc aggaagctga gaacggcca aaaatgtttg aagaactagg acagaggctg    2460
cagcattatg ccaagatagc agctgacttc agaaataagg atgagaaata caaccatatt    2520
gatgagtctg aaatgaaaaa agtggagaag tctgttaatg aagtgatgga atggatgaat    2580
aatgtcatga atgctcaggc taaaaagagt cttgatcagg atccagttgt acgtgctcag    2640
gaaattaaaa caaaaatcaa ggaattgaac aacacatgtg aacccgttgt aacacaaccg    2700
aaaccaaaaa ttgaatcacc caaactggaa agaactccaa atggcccaaa tattgataaa    2760
aaggaagaag atttagaaga caaaaacaat tttggtgctg aacctccaca tcagaatggt    2820
gaatgttacc ctaatgagaa aaattctgtt aatatggact tggactagat aaccttaaat    2880
tggcctattc cttcaattaa taaaatattt ttgccatagt atgtgactct acataacata    2940
ctgaaactat ttatatttc tttttttaagg atatttagaa attttgtgta ttatatggaa    3000
aaagaaaaaa agcttaagtc tgtagtcttt atgatcctaa aagggaaaat tgccttggta    3060
actttcagat tcctgtggaa ttgtgaattc atactaagct ttctgtgcag tctcaccatt    3120
tgcatcactg aggatgaaac tgactttgt cttttggaga aaaaaactg tactgcttgt    3180 tcaagagggc tgtgattaaa atctttaagc atttgttcct gccaaggtag ttttcttgca    3240
ttttgctctc cattcagcat gtgtgtggt gtggatgttt ataacaaga ctaagtctga    3300 cttcataagg gctttctaaa accatttctg tccaagagaa aatgactttt tgctttgata    3360
ttaaaaattc aatgagtaaa acaaaagcta gtcaaatgtg ttagcagcat gcagaacaaa    3420
aactttaaac tttctctctc actatacagt atattgtcat gtgaaagtgt ggaatggaag    3480
aaatgtcgat cctgttgtaa ctgattgtga acacttttat gagctttaaa ataaagttca    3540
tcttatggtg tcatttctaa aaaaaaaaaa aaa                                 3573
```

<210> SEQ ID NO 4
<211> LENGTH: 22
<212> TYPE: DNA
<213> ORGANISM: Homo sapiens

<400> SEQUENCE: 4
gctacacgaa ttccagctgt ga    22

<210> SEQ ID NO 5

<211> LENGTH: 22
<212> TYPE: DNA
<213> ORGANISM: Homo sapiens

<400> SEQUENCE: 5
gagcagcatg gtttcgacta aa                                              22

<210> SEQ ID NO 6
<211> LENGTH: 18
<212> TYPE: DNA
<213> ORGANISM: Homo sapiens

<400> SEQUENCE: 6
atgtgcatta cagtgttc                                                   18

<210> SEQ ID NO 7
<211> LENGTH: 17
<212> TYPE: DNA
<213> ORGANISM: Homo sapiens

<400> SEQUENCE: 7
tacagtgtgc aatactt                                                    17

<210> SEQ ID NO 8
<211> LENGTH: 3680
<212> TYPE: DNA
<213> ORGANISM: Homo sapiens

<400> SEQUENCE: 8
tgagtaaatg ccgcagattc tggaaagttc tgatcagtgc gatacataag gctgaggaag     60
tgggacctcc ccttttgggt cggtagttca gcgccggcgc cggtgtgcga gccgcggcag    120
agtgaggcag gcaacccgag gtgcggagcg acctgcggag gctgagcccc gctttctccc    180
agggtttctt atcagccagc cgccgctgtc cccggggag taggaggctc ctgacaggcc     240
gcggctgtct gtgtgtcctt ctgagtgtca gaggaacggc cagaccccgc gggccggagc    300
agaacgcggc cagggcagaa agcggcggca ggagaagcag gcaggggcc ggaggacgca      360
gaccgagacc cgaggcggag gcggaccgcg agccggccat gtcggtggtg gggttggacg    420
tgggctcgca gagctgctac atcgcggtag cccgggccgg gggcatcgag accatcgcca    480
atgagttcag cgaccggtgc accccgtcag tcatatcatt tggatcaaaa aatagaacaa    540
tcggagttgc agccaaaaat cagcaaatca ctcatgcaaa caatacggtg tctaacttca    600
aaagatttca tggccgagca ttcaatgacc ccttcattca aaggagaag gaaaacttga      660
gttacgattt ggttccattg aaaaatggtg gagttggaat aaaggtaatg tacatgggtg    720
aagaacatct atttagtgtg gagcagataa cagccatgtt gttgactaag ctgaaggaaa    780
ctgctgaaaa cagcctcaag aaaccagtaa cagattgtgt tatttcagtc ccctccttct    840
ttacagatgc tgagaggcga tctgtgttag atgctgcaca gattgttggc ctaaactgtt    900
taagacttat gaatgacatg acagctgttg cttttgaatta cggaattat aagcaggatc     960
tcccaagcct ggatgagaaa cctcggatag tggttttttgt tgatatggga cattcagctt   1020
ttcaagtgtc tgcttgtgct tttaacaagg gaaaattgaa ggtactggga acagcttttg    1080
atcctttctt aggaggaaaa aacttcgatg aaaagttagt ggaacatttt tgtgcagaat    1140
ttaaaactaa gtacaagttg gatgcaaaat ccaaaatacg agcactccta cgtctgtatc    1200
aggaatgtga aaaactgaaa aagctaatga gctctaacag cacagacctt ccactgaata    1260
tcgaatgctt tatgaatgat aaagatgttt ccggaaagat gaacaggtca caatttgaag    1320

```
aactctgtgc tgaacttctg caaaagatag aagtaccect ttattcactg ttggaacaaa    1380
ctcatctcaa agtagaagat gtgagtgcag ttgagattgt tggaggcgct acacgaattc    1440
cagctgtgaa ggaaagaatt gccaaattct ttggaaaaga tattagcaca acactcaatg    1500
cagatgaagc agtagccaga ggatgtgcat tacagtgtgc aatactttcc ccggcattta    1560
aagttagaga attttccgtc acagatgcag ttccttttcc aatatctctg atctggaacc    1620
atgattcaga agatactgaa ggtgttcatg aagtctttag tcgaaaccat gctgctcctt    1680
tctccaaagt tctcacctt ctgagaaggg ggccttttga gctagaagct ttctattctg     1740
atccccaagg agttccatat ccagaagcaa aaataggccg ctttgtagtt cagaatgttt    1800
ctgcacagaa agatggagaa aaatctagag taaaagtcaa agtgcgagtc aacacccatg    1860
gcattttcac catctctacg gcatctatgg tggagaaagt cccaactgag gagaatgaaa    1920
tgtcttctga agctgacatg gagtgtctga atcagagacc accagaaaac ccagacactg    1980
ataaaaatgt ccagcaagac aacagtgaag ctggaacaca gccccaggta caaactgatg    2040
ctcaacaaac ctcacagtct ccccttcac ctgaacttac ctcagaagaa acaaaatcc      2100 cagatgctga caaagcaaat gaaaaaaaag ttgaccagcc tccagaagct aaaaagccca    2160
aaataaaggt ggtgaatgtt gagctgccta ttgaagccaa cttggtctgg cagttaggga    2220
aagaccttct taacatgtat attgagacag agggtaagat gataatgcaa gataaattgg    2280
aaaaagaaag gaatgatgct aaaaatgcag ttgaggaata tgtgtatgag ttcagagaca    2340
agctgtgtgg accatatgaa aaatttatat gtgagcagga tcatcaaaat ttttgagac     2400 tcctcacaga aactgaagac tggctgtatg aagaaggaga ggaccaagct aaacaagcat    2460
atgttgacaa gttggaagaa ttaatgaaaa ttggcactcc agttaaagtt cggtttcagg    2520
aagctgaaga acggccaaaa atgtttgaag aactaggaca gaggctgcag cattatgcca    2580
agatagcagc tgacttcaga aataaggatg agaaatacaa ccatattgat gagtctgaaa    2640 tgaaaaagt ggagaagtct gttaatgaag tgatggaatg gatgaataat gtcatgaatg     2700
ctcaggctaa aaagagtctt gatcaggatc cagttgtacg tgctcaggaa attaaaacaa    2760
aaatcaagga attgaacaac acatgtgaac ccgttgtaac acaaccgaaa ccaaaaattg    2820
aatcacccaa actggaaaga actccaaatg gcccaaatat tgataaaaag gaagaagatt    2880
tagaagacaa aaacaatttt ggtgctgaac ctccacatca gaatggtgaa tgttacccta    2940
atgagaaaaa ttctgttaat atggacttgg actagataac cttaaattgg cctattcctt    3000
caattaataa aatattttg ccatagtatg tgactctaca taacatactg aaactattta     3060
tattttcttt ttaaggata tttagaaatt ttgtgtatta tatggaaaaa gaaaaaaagc     3120
ttaagtctgt agtctttatg atcctaaaag ggaaaattgc cttggtaact ttcagattcc    3180
tgtggaattg tgaattcata ctaagctttc tgtgcagtct caccatttgc atcactgagg    3240
atgaaactga cttttgtctt ttggagaaaa aaactgtac tgcttgttca agagggctgt     3300
gattaaaatc tttaagcatt tgttcctgcc aaggtagttt tcttgcattt tgctctccat    3360
tcagcatgtg tgtgggtgtg atgttttata aacaagacta agtctgactt cataagggct    3420
ttctaaaacc atttctgtcc aagagaaaat gacttttgc tttgatatta aaaattcaat     3480
gagtaaaaca aaagctagtc aaatgtgtta gcagcatgca gaacaaaaac tttaaacttt    3540
ctctctcact atacagtata ttgtcatgtg aaagtgtgga atggaagaaa tgtcgatcct    3600
gttgtaactg attgtgaaca ctttttatgag ctttaaaata aagttcatct tatggtgtca    3660
```

```
tttctaaaaa aaaaaaaaaa                                                3680
```

<210> SEQ ID NO 9
<211> LENGTH: 164
<212> TYPE: DNA
<213> ORGANISM: Homo sapiens

<400> SEQUENCE: 9

```
gaaaaccctg tccatccatt ggaattgagt tttatattaa aagatgactg ggaagtgttc    60
atgtgctcat gattttttt tttttttta agtgtgcaat actttcccct ttccccggca     120
tttaaagtta gagaattttc cgtcacagat gcagttcctt ttcc                    164
```

<210> SEQ ID NO 10
<211> LENGTH: 23
<212> TYPE: DNA
<213> ORGANISM: Homo sapiens

<400> SEQUENCE: 10

```
ccctgtccat ccattggaat tga                                            23
```

<210> SEQ ID NO 11
<211> LENGTH: 21
<212> TYPE: DNA
<213> ORGANISM: Homo sapiens

<400> SEQUENCE: 11

```
ggaactgcat ctgtgacgga a                                              21
```

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12

```
cgcgcgcgca agatctacat gtcggtggtg ggg                                 33
```

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13

```
cgcgcgcgca agctttcatg aacactgtaa tgcacatcc                           39
```

<210> SEQ ID NO 14
<211> LENGTH: 21
<212> TYPE: DNA
<213> ORGANISM: Homo sapiens

<400> SEQUENCE: 14

```
ctgcggtaat caagttttta g                                              21
```

<210> SEQ ID NO 15
<211> LENGTH: 22
<212> TYPE: DNA
<213> ORGANISM: Homo sapiens

<400> SEQUENCE: 15

```
aaccattcaa cattttaac cc                                              22
```

```
<210> SEQ ID NO 16
<211> LENGTH: 20
<212> TYPE: DNA
<213> ORGANISM: Homo sapiens

<400> SEQUENCE: 16
gagtcgctgg cacagttcta                                              20

<210> SEQ ID NO 17
<211> LENGTH: 20
<212> TYPE: DNA
<213> ORGANISM: Homo sapiens

<400> SEQUENCE: 17
ctggtcactc gcgtttacaa                                              20

<210> SEQ ID NO 18
<211> LENGTH: 20
<212> TYPE: DNA
<213> ORGANISM: Homo sapiens

<400> SEQUENCE: 18
aaccatgctt gcaaaccact                                              20

<210> SEQ ID NO 19
<211> LENGTH: 20
<212> TYPE: DNA
<213> ORGANISM: Homo sapiens

<400> SEQUENCE: 19
cgataatact agcaatgacc                                              20

<210> SEQ ID NO 20
<211> LENGTH: 20
<212> TYPE: DNA
<213> ORGANISM: Homo sapiens

<400> SEQUENCE: 20
gctgaatttt acctcctgac                                              20

<210> SEQ ID NO 21
<211> LENGTH: 20
<212> TYPE: DNA
<213> ORGANISM: Homo sapiens

<400> SEQUENCE: 21
attgtgccat tgcattccaa                                              20

<210> SEQ ID NO 22
<211> LENGTH: 19
<212> TYPE: DNA
<213> ORGANISM: Homo sapiens

<400> SEQUENCE: 22
taccaggtgg caaagggca                                               19

<210> SEQ ID NO 23
<211> LENGTH: 21
<212> TYPE: DNA
<213> ORGANISM: Homo sapiens

<400> SEQUENCE: 23
tctgcatttt aactatggct c                                            21
```